US011180738B2

(12) United States Patent
Aebi et al.

(10) Patent No.: US 11,180,738 B2
(45) Date of Patent: Nov. 23, 2021

(54) METHOD FOR PRODUCING AN N-METHYLATED (POLY) PEPTIDE

(71) Applicant: ETH ZURICH, Zurich (CH)

(72) Inventors: Markus Aebi, Wettingen (CH); Markus Kunzler, Neuenhof (CH); Jorn Piel, Zurich (CH); Michael Freeman, Feeding Hills, MA (US); Niels Van Der Velden, Houten (NL); Noemi Kalin, Emmenbrucke (CH)

(73) Assignee: ETH ZURICH, Zurich (CH)

( * ) Notice: Subject to any disclaimer, the term of this patent is extended or adjusted under 35 U.S.C. 154(b) by 112 days.

(21) Appl. No.: 16/091,038

(22) PCT Filed: Apr. 7, 2017

(86) PCT No.: PCT/EP2017/058327

§ 371 (c)(1),
(2) Date: Oct. 3, 2018

(87) PCT Pub. No.: WO2017/174760

PCT Pub. Date: Oct. 12, 2017

(65) Prior Publication Data

US 2019/0112583 A1 Apr. 18, 2019

(30) Foreign Application Priority Data

Apr. 7, 2016 (EP) .................................... 16164245

(51) Int. Cl.

| | |
|---|---|
| *C12N 9/10* | (2006.01) |
| *C07K 16/00* | (2006.01) |
| *C07K 14/375* | (2006.01) |
| *C07K 16/40* | (2006.01) |
| *C12P 21/02* | (2006.01) |

(52) U.S. Cl.

CPC .......... *C12N 9/1007* (2013.01); *C07K 14/375* (2013.01); *C07K 16/00* (2013.01); *C07K 16/40* (2013.01); *C12P 21/02* (2013.01); *C12Y 201/01049* (2013.01); *C07K 2319/00* (2013.01); *C07K 2319/21* (2013.01); *C07K 2319/50* (2013.01)

(58) Field of Classification Search

None

See application file for complete search history.

(56) References Cited

U.S. PATENT DOCUMENTS 5,582,981 A 12/1996 Toole et al.

FOREIGN PATENT DOCUMENTS

CA 2418798 11/2002

OTHER PUBLICATIONS

Chica et al. Curr Opin Biotechnol. Aug. 2005;16(4):378-84. (Year: 2005).*

Singh et al. Curr Protein Pept Sci. 2017, 18, 1-11 (Year: 2017).*

Velkov et al. Chemistry & Biology. vol. 18, Issue 4, Apr. 22, 2011, pp. 464-475 (Year: 2011).*

Luo et al. Chem Biol, 21 (2014), pp. 1610-1617 (Year: 2014).*

International Search Report and Written Opinion from PCT/EP2017/058327, dated Jun. 9, 2017.

Arnison PG, et al. (2013), Ribosomally synthesized and post-translationally modified peptide natural products: overview and recommendations for a universal nomenclature, Nat Prod Rep 30, 108-160.

Butterfield, et al., (2012), Chemical Strategies for Controlling Protein Folding and Elucidating the Molecular Mechanisms of Amyloid Formation and Toxicity, J. Mol. Biol. 421, 204-236.

Chatterjee, et al., (2008), N-Methylation of Peptides: A New Perspective in Medicinal Chemistry, Accts Chem Res 41, 1331-1342, Oct. 2008.

Chatterjee, et al., (2013), N-Methylation of Peptides and Proteins: An Important Element for Modulating Biological Functions, Angew Chem Int Ed 52, 254-269.

Floudas, D., et al., (2012), The Paleozoic origin of enzymatic lignin decomposition reconstructed from 31 fungal genomes, Science, vol. 336, No. 6089, pp. 1715-1719, Jun. 29, 2012.

Grunewald, J., et al., (2006), Chemoenzymatic and template-directed systhesis of bioactive macrocyclic peptides, Microbiology and Molecular Biology Reviews, American Society for Microbiology, US., vol. 70, No. 1, pp. 121-146, Mar. 1, 2006.

Hallen, et al. (2007), Gene family encoding the major toxins of lethal, Amanita mushrooms Proc Natl Acad Sci USA 104, 19097-19101, Nov. 27, 2007.

Lawen, (2015), Biosynthesis of cyclosporins and other natural peptidyl prolyl cis/trans isomerase inhibitors, Biochem Biophys Acta 1850 (2015) 2111-2120.

Mayer, Sterner, Etzel, Anke, (1997) Omphalotin, A New Cyclic Peptide With Potent Nematicidal Activity From Omphalotus Olearius II. Isolation And Structure Determination, Nat. Prod. Lett. 10, 33-38.

Meinhardt, Lyndel W., et al., (2014), Genome and secretome analysis of the hemibiotrophic fungal pathogen, moniliophthora roreri, which caused frosty pod rot disease of cacao: mechanisms of the biotrophic and necrotrophic phases, BMC Genomics, Biomed Central Ltd, London UK, vol. 15, No. 1, p. 164, Feb. 27, 2014.

Peel and Scribner, (2015), Semi-synthesis of cyclosporins, Biochem Biophys Acta 1850 (2015) 2121-2144.

(Continued)

*Primary Examiner* — Christian L Fronda

(74) *Attorney, Agent, or Firm* — Bryan D. Zerhusen; Nicholas R. Herrel; Cantor Colburn LLP

(57) ABSTRACT

The present invention is directed to all aspects of novel methyl transferase enzymes that methylate backbone amides of (poly)peptides. The present invention also relates to nucleic acids encoding these enzymes as well as corresponding vectors and host cells comprising these. Moreover, the present invention encompasses the use of said enzymes for modifying (poly)peptides as well as corresponding methods. Also, the present invention pertains to further novel enzymes for modifying (poly)peptides derived from the omphalotin gene cluster of *O. olearius* and the homologous gene clusters from *D. bispora, L. edodes* and *F. mediterranea* as well as related aspects.

15 Claims, 9 Drawing Sheets

Specification includes a Sequence Listing.

(56) References Cited

OTHER PUBLICATIONS

Thern, et al., (2002), Total Synthesis of the Nematicidal Cyclododecapeptide Omphalotin A by Using Racemization-Free Triphosgene-Mediated Couplings in the Solid Phase , Angew Chem Int Ed 41, No. 13, 2307-2309.
Umemura, et al. (2014), Characterization of the biosynthetic gene cluster for the ribosomally synthesized cyclic peptide ustiloxin B in Aspergillus flavus, Fung Gen Biol 68, 23-30.
Velkov, et al., (2011), Characterization of the N-Methyltransferase Activities of the Multifunctional Polypeptide Cyclosporin Synthetase, Chem Biol 18, 464-475, Apr. 22, 2011.
White, et al., (2011), On-resin N-methylation of cyclic peptides for discovery of orally bioavailable scaffolds, (2011) Nat Chem Biol 7(11): 810-817.

* cited by examiner

Fig. 1

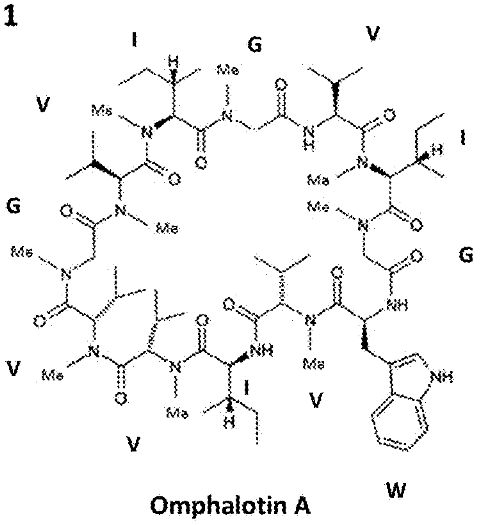

Omphalotin A

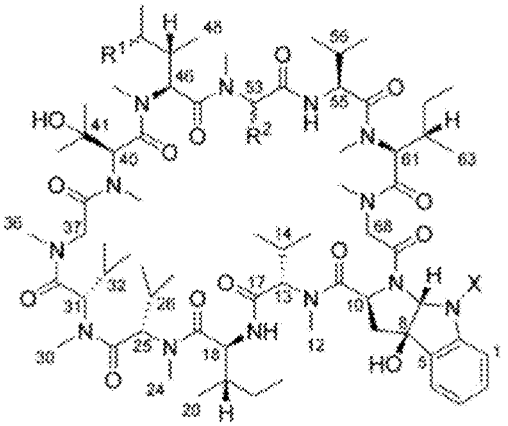

Omphalotin B - I

1 Omphalotin B: $R^1$ = A, $R^2$ = OH
2 Omphalotin C: $R^1$ = A, $R^2$ = OAc
3 Omphalotin D: $R^1$, $R^2$ = OAc
4 Omphalotin E: $R^1$, $R^2$, X = H
5 Omphalotin F: $R^1$, $R^2$ = H, X = OH
6 Omphalotin G: $R^1$ = H, $R^2$, X = OH
7 Omphalotin H: $R^1$, $R^2$ = OAc, X = OH
8 Omphalotin I: $R^1$ = B, $R^2$ = OAc, X= OH A: 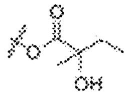 B: 

Fig. 2

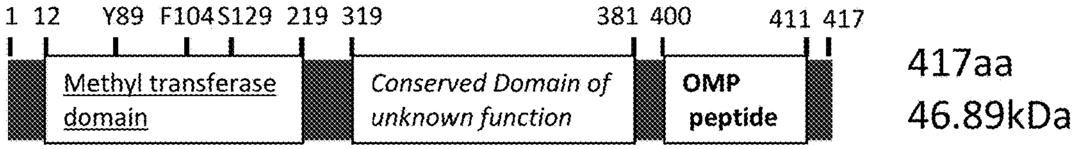

METSTQTKAGSLTIVGTGIESIGQMTLQALSYIEAAAKVFYCVIDPATEAFILTKNKNCVDLYQYYD
NGKSRLNTYTQMSELMVREVRKGLDVVGVFYGHPGVFVNPSHRALAIAKSEGYRARMLPGVS
AEDCLFADLCIDPSNPGCLTYEASDFLIRDRPVSIHSHLVLFQVGCVGIADFNFTGFDNNKFGVLV
DRLEQEYGAEHPVVHYIAAMMPHQDPVTDKYTVAQLREPEIAKRVGGVSTFYIPPKARKASNLD
IIRRLELLPAGQVPDKKARIYPANQWEPDVPEVEPYRPSDQAAIAQLADHAPPEQYQPL*ATSKA*
*MSDVMTKLALDPKALADYKADHRAFAQSVPDLTPQERAALELGDSWAIRCAMKNMPSS*LLDA
ARESGEEASQNGFPWVIVVGVIGVIGSVMSTE
(SEQ ID NO: 15)

Fig. 3B

| Gene | Protein ID* | Scaffold number | Gene start | Gene stop | Gene length | # of introns | Transcript length | Protein length |
|---|---|---|---|---|---|---|---|---|
| *O. olearius* gene cluster | | | | | | | | |
| *ophB1* | 2085 | 169 | 2522 | 4276 | 1161 | 10 | 1755 | 386 |
| *ophC* | 2086 | 169 | 4716 | 5286 | 375 | 3 | 569 | 124 |
| *ophA* | 2087 | 169 | 9536 | 10904 | 1369 | 2 | 1254 | 417 |
| *ophD* | 2088 | 169 | 11859 | 12616 | 758 | 1 | 696 | 231 |
| *ophB2* | 2089 | 169 | 13183 | 15046 | 1497 | 7 | 1864 | 498 |
| *ophP* | 2090 | 169 | 16016 | 19346 | 2172 | 21 | 3331 | 723 |
| *ophE* | 2091 | 169 | 20170 | 21484 | 1251 | 1 | 1315 | 416 |
| *D. bispora ophA* gene cluster | | | | | | | | |
| *dbophB1* | 971518 | 621 | 40768 | 43005 | 2128 | 11 | 1515 | 504 |
| *dbophB2* | 971517 | 621 | 38089 | 40469 | 2313 | 11 | 1629 | 542 |
| *dbophC* | 871170 | 621 | 37262 | 37791 | 570 | 3 | 363 | 120 |
| *dbophD1* | 784138 | 621 | 34955 | 36331 | 1208 | 1 | 1092 | 363 |
| *dbophB3* | 831474 | 621 | 32392 | 34679 | 1864 | 7 | 1497 | 498 |
| *dbophA* | 765759 | 621 | 28937 | 30516 | 1384 | 2 | 1254 | 417 |
| *dbophD2* | 765756 | 621 | 27371 | 28885 | 1232 | 1 | 1113 | 370 |
| *dbophB4* | 765754 | 621 | 25288 | 27217 | 1854 | 6 | 1485 | 542 |
| *dbophP* | 765750 | 621 | 17398 | 24733 | 3500 | 20 | 1830 | 609 |
| *dbophE* | 871164 | 621 | 19236 | 20583 | 1278 | 1 | 1278 | 313 |

Fig. 4

*Fomitiporia mediterranea*

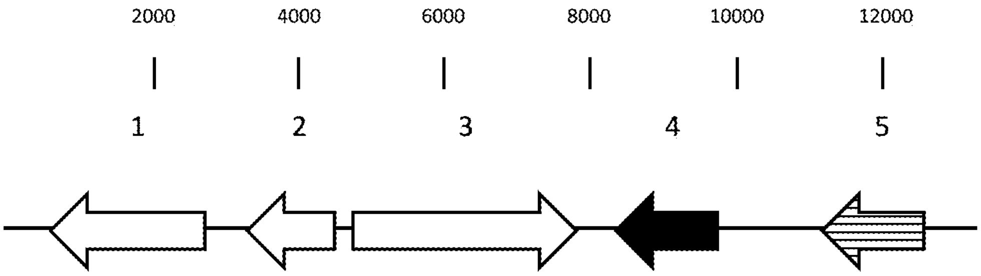

1) 32307 - Serine / threonine kinase
2) 32308 - Nitrilase / cyanide hydratase
3) 32309 - Ubiquitin-dependent protein catabolism
4) 32310 - Methyltransferase
5) 32311 - Aspartic peptidase

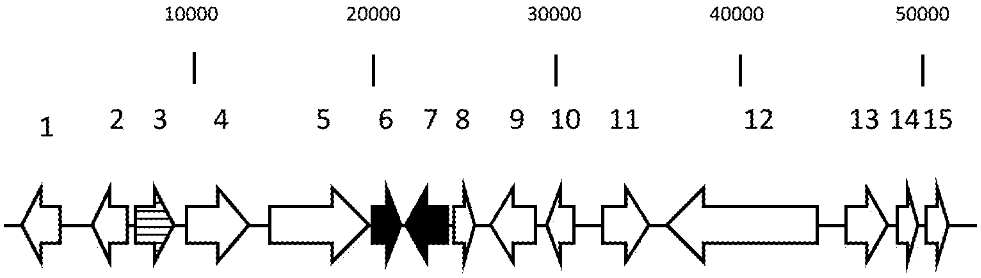

1) 25783 - Unknown
2) 25784 - Unknown
3) 144537 - Prolyl oligopeptidase
4) 25786 - Unknown
5)25787 - Unknown
6) 25788 - Unknown
7) 25789 - Chaperonin
8) 25790 - Phosphatase
9) 25791 - AMP-dependent synthase and ligase
10)25792 - Methyltransferase
11) 25793 - Methyltransferase
12) 25794 - Haem peroxidase
13) 25795 - Unknown
14) 25796 - Unknown
15) 25797 - Unknown

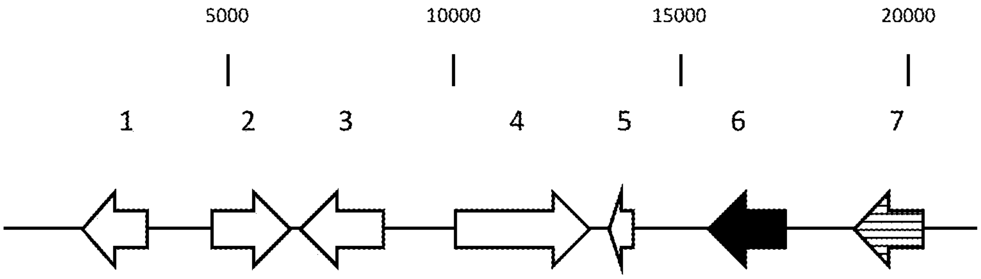

1) 30899 - AMP dependent synthetase and ligase
2) 30900 - Unknown
3) 30901 - Unknown
4) 30902 - AMP dependent synthetase and ligase
5) 30903 - VPS28 protein
6) 30904 - Methyltransferase
7) 30905 - Aspartic peptidase

Fig. 5A (SEQ ID NOs: 15, 17, 27, 23, 25, 19, 21)
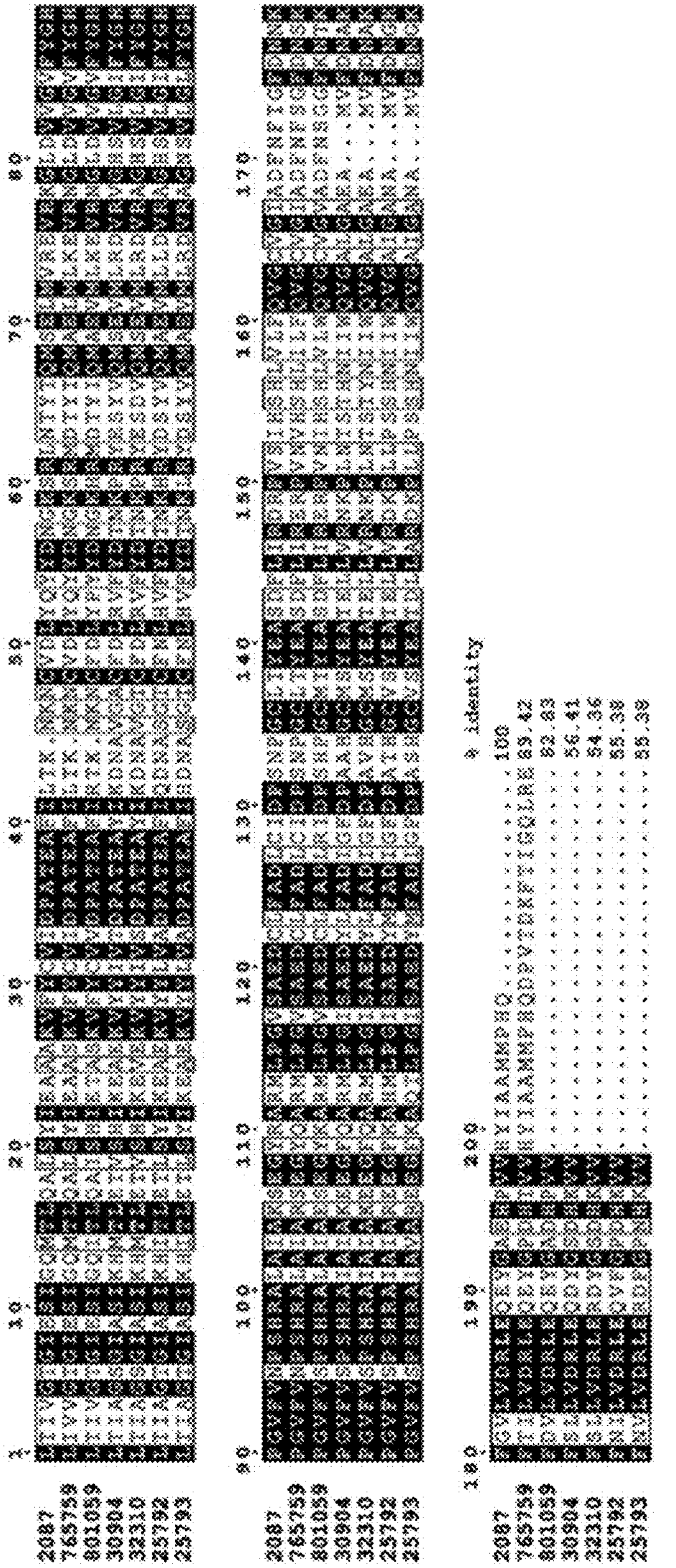
Fig. 5B (SEQ ID NOs: 37, 54)
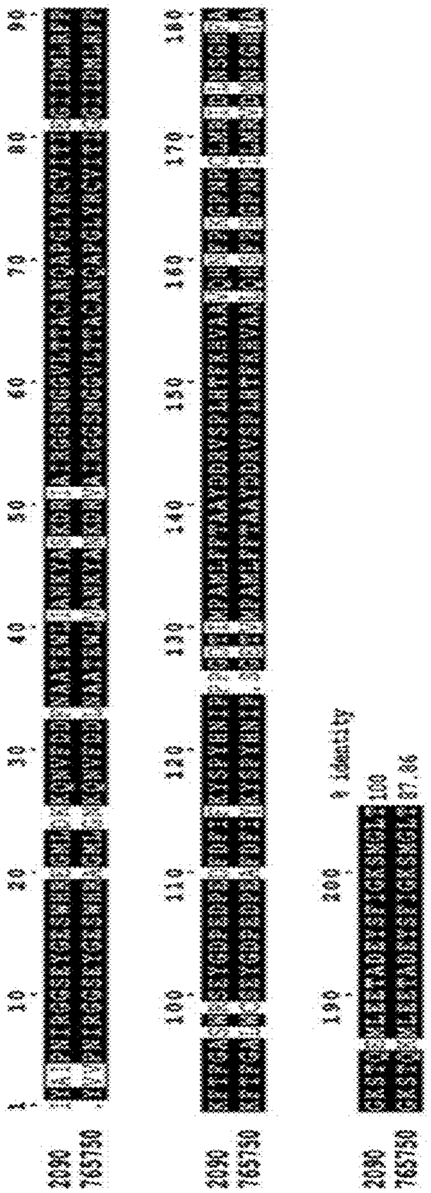

Fig. 8A

Omp SEQ ID NO: 99

| | |
|---|---|
| | ESGEEASQNGFPWVIVVGVIGVIGSVMSTE |
| 5 Day + Trypsin: | ESGEEASQNGFPWVIVVGVIGVIGSVMSTE |
| 1 Day + Trypsin: | *ESGEEASQNGFPWVIVVGVIGVIGSVMSTE* |
| 1 Day + Trypsin: | ESGEEASQNGFPWVIVVGVIGVIGSVMSTE |
| 1 Day + Trypsin: | ESGEEASQNGFPWVIVVGVIGVIGSVMSTE |
| 1 Day + Trypsin: | ESGEEASQNGFPWVIVVGVIGVIGSVMSTE |
| 1 Day + Trypsin: | ESGEEASQNGFPWVIVVGVIGVIGSVMSTE |
| 1 Day + Trypsin: | ESGEEASQNGFPWVIVVGVIGVIGSVMSTE |
| 1 Day + Trypsin: | ESGEEASQNGFPWVIVVGVIGVIGSVMSTE |
| 1 Day + Trypsin: | ESGEEASQNGFPWVIVVGVIGVIGSVMSTE |
| 1 Day + Trypsin: | ESGEEASQNGFPWVIVVGVIGVIGSVMSTE |
| 1 Day + Trypsin: | ESGEEASQNGFPWVIVVGVIGVIGSVMSTE |

Minor components observed

| | |
|---|---|
| 5 Day + Trypsin: | ESGEEASQNGFPWVIVVGVIGVIGSVMSTE |
| 1 Day + Trypsin: | ESGEEASQNGFPWVIVVGVIGVIGSVMSTE |
| | ESGEEASQNGFPWVIVVGVIGVIGSVMSTE |

N = N-Me detected N = expected N-Me *N* = major species observed

Fig. 8B

***D. bispora 765750* (SEQ ID NO: 100)**

1 Day + Trypsin: NMPSSLLEAASQSVEEASMNGFPWVIVTGIVGVIGSVVSSA

Fig. 8C Omp no follower (SEQ ID NO: 101)

ESGEEASQNGFPWVIVVGVIGVIG

5 Day + Trypsin: ESGEEASQNGFPWVIVVGVIGVIG

5 Day + Trypsin: *ESGEEASQNGFPWVIVVGVIGVIG*

Fig. 8D Omp TEV cleavage site (SEQ ID NO:102)

ESGENLYFQGFPWVIVVGVIGVIG

5 Day + Trypsin: *ESGENLYFQGFPWVIVVGVIGVIG*

5 Day + Trypsin: ESGENLYFQGFPWVIVVGVIGVIG

1 Day + Trypsin: ESGENLYFQGFPWVIVVGVIGVIG

1 Day + Trypsin: ESGENLYFQGFPWVIVVGVIGVIG

1 Day + Trypsin: ESGENLYFQGFPWVIVVGVIGVIG

1 Day + Trypsin: ESGENLYFQGFPWVIVVGVIGVIG

1 Day + Trypsin: ESGENLYFQGFPWVIVVGVIGVIG

1 Day + Trypsin: ESGENLYFQGFPWVIVVGVIGVIG

1 Day + Trypsin: ESGENLYFQGFPWVIVVGVIGVIG

Minor component observed

[ESGENLYFQGFPWVIVVGVIGVIG]

N = N-Me detected

N = expected N-Me

*N* = major species observed

Fig. 9

| | cyclosporin A | dictyonamide A | |
|---|---|---|---|
| (1) | R2, *, LVLAALLVT-VG, R1 | ATTVVVVVIVG-Abz | |
| | (SEQ ID NO: 103) | (SEQ ID NO: 104) | |
| (2) | 1Me ***LV***LAALLVIVG | 1Me 1Me ***AT***TVVVVVI***VG*** | 1Me 2Me 1Me ***ATTVV***VVVI***VG*** |
| (3) | LVLAALLVIVG | 1Me 1Me A***TV***VVVVI***VG*** | 1Me 1Me 1Me ***AT***T***VVV***VVI***VG*** |
| (4) | LVLAALLVIVG | 1Me ATTVVVVVI***VG*** | ATTVVVVVIVG |
| (5) | LVLAALLVIVG | 1Me1Me 1Me A***TVVV***VVI***VG*** | ATTVVVVVIVG |
| (6) | LVLAALLVIVG | ATTVVVVVIVG | ATTVVVVVIVG |

| | R1 | kendarimide A |
|---|---|---|
| (7) | VFAEFLPLFSKFGSRMHILK | R3-FIAVVVVAVVcc-R4 |
| | (SEQ ID NO: 105) | (SEQ ID NO: 106) |
| (8) | VFAEFLPLFSKFGSRMHILK | QFIAVVVVAVVccF |
| (9) | VFAEFLPLFSKFGSRMHILK | QFIAVVVVAVVccF |
| (10) | | 6Me/5Me/4Me/3Me **QFIAVVVVAVVccF** |

N = N-Me detected
*N* = N-Me detected position not defined

* = D-alanine
R1= butenyl-methyl
R2= L-alpha-aminobutyric acid
Abz= anthranilic acid R3= L-pyroMeGlu
R4=L-Phenylalaninol
cc= disulphide bridge between two cysteines

METHOD FOR PRODUCING AN N-METHYLATED (POLY) PEPTIDE

RELATED APPLICATION

This application is a National Stage of PCT/EP2017/058327, filed: 7 Apr. 2017, titled: NOVEL MULTIPLY BACKBONE N-METHYL TRANSFERASES AND USES THEREOF, published as International Patent Application No. WO 2017/174760 A1, which claims the benefit and priority to European Patent Application No. 16164245.9, filed on 7 Apr. 2016, all of which are incorporated by reference in their entirety for all purposes.

INCORPORATION BY REFERENCE

In compliance with 37 C.F.R. § 1.52(e)(5), the sequence information contained in electronic file name: 50508PCT_Sequence_Listing_ST25.txt; size 210 KB; created on: 7 Apr. 2017; using Patent-In 3.5 is hereby incorporated herein by reference in its entirety.

FIELD OF THE INVENTION

The present invention is directed to all aspects of novel methyl transferase enzymes that methylate backbone amides of (poly)peptides. The present invention also relates to nucleic acids encoding these enzymes as well as corresponding vectors and host cells comprising these. Moreover, the present invention encompasses the use of said enzymes for modifying (poly)peptides as well as corresponding methods. Also, the present invention pertains to further novel enzymes for modifying (poly)peptides derived from the omphalotin gene cluster of *O. olearius* and the homologous clusters from *D. bispora, L. edodes* and *F. mediterranea* as well as related aspects.

BACKGROUND

Multiple backbone N-methylated (macrocyclic) peptides have interesting pharmacodynamic properties, e.g. increased bioavailability due to increased permeability for oral and intestinal epithelial membranes, increased half-life in vivo due to increased stability towards proteinases, reduced structural flexibility and the ability to disassemble aggregates and fibrils of their corresponding native non-methylated sequences (Chatterjee et al., (2008) Accts Chem Res 41:1331-1342, Chatterjee et al., (2013) Angew Chem Int Ed 52:254-269, Butterfield et al., (2012) J. Mol. Biol. 421:204-236). The chemical synthesis of such peptides is complicated and therefore very expensive (White et al., (2011) Nat Chem Biol 7:810-817). Multiply backbone N-methylated peptides like cyclosporin A are produced by architecturally highly complex non-ribosomal peptide synthetases (NRPSs) and N-methylated during elongation of the peptide by a built-in methyl transferase domain of the respective NRPS (Velkov et al., (2011) Chem Biol 18:464-475). Such a biosynthetic pathway is difficult to modify e.g. for the production of slightly altered versions, with regard e.g. to the peptide sequence or the N-methylation pattern, of the respective peptide or the production of peptide libraries because one has to reengineer the NRPS machinery which is very challenging (Thern et al., (2002) Angew Chem Int Ed 41:2307-2309, Lawen (2015) Biochem Biophys Acta 1850: 2111-2120, Peel and Scribner, (2015) Biochem Biophys Acta 1850:2121-2144).

Large-scale production of backbone N-methylated (cyclic) peptides requires either fermentation followed by purification from the respective naturally occurring microbes (bacteria or fungi) or from recombinant bacteria carrying the respective NRPSs. The only other currently available alternative to provide such compounds is complicated chemical synthesis. The methods can also be combined e.g. by chemical or enzymatic modification of the fermentation product (Peel and Scribner (2015) Biochem Biophys Acta 1850: 2121-2144).

Ribosomally synthesized and post-translationally modified peptides, so-called RiPPs, also known as ribosomal peptide natural products, are a diverse class of natural products of ribosomal origin consisting of more than 20 subclasses that are produced by a variety of organisms, including prokaryotes, eukaryotes and archaea (Arnison P G et al., (2013) Nat Prod Rep 30:108-160). Ribosomally synthesized peptides have the advantage that they can be modified easily by simply changing the template/coding region of the peptide-encoding gene. So far, only two fungal RiPPs have been described, the ama/phallotoxins (Hallen et al., (2007) Proc Natl Acad Sci USA 104:19097-19101) and the ustiloxins (Umemura et al., (2014) Fung Gen Biol 68:23-30), and none of them are backbone N-methylated.

Omphalotin A was isolated in 1997 from the basidiomycete *Omphalotus olearius* (*O. olearius*) in order to find an active compound against the root-knot nematode *Meloidogyne incognita* (Mayer, (1997) Nat. Prod. Lett. 10:33-38). The omphalotins are highly backbone N-methylated, cyclic peptides consisting of 12 amino acids (FIG. 1, *Atta*-ur-Rahman (2015). "Studies in Natural Products Chemistry", Vol. 44 Chapter 3: 93-110). Due to the high degree of posttranslational modifications in the omphalotins (e.g. cyclization, hydroxylation's, O-acylation and backbone N-methylation) they are presently thought to belong to the class of non-ribosomally synthesized fungal peptides.

In view of the above, it is the objective technical problem underlying the present invention to provide new methylated (poly)peptides, preferably N-methylated (poly) peptides, more preferably backbone N-methylated (poly)peptides, and novel enzymatic tools for producing these as well as corresponding methods and uses of these enzymatic tools.

It is a further objective underlying the present invention to provide new enzyme tools for modifying (poly)peptides, in particular methylated (poly)peptides, preferably novel proteases, oxygenases, O-acyl transferases, and oxidoreductases with broad substrate specificity, to manufacture these enzymatic tools economically, and to provide corresponding (poly)peptide-modifying uses and methods.

BRIEF SUMMARY OF THE INVENTION

The above objectives are solved in a first aspect by a preferably isolated and purified nucleic acid, comprising a nucleic acid sequence selected from the group consisting of:

(i) a nucleic acid sequence selected from the group consisting of nucleic acid sequences listed in SEQ ID NOs: 1 to 14 and 108 to 111, preferably SEQ ID NOs: 2, 4, 6, 8, 10, 12, 14, and 108 (MT domains), more preferably SEQ ID NOs: 1 and 2;

(ii) a nucleic acid sequence of at least 60 or 70% identity, 80 or 90% identity, preferably at least 95% identity, more preferred at least 98% identity with the nucleic acid sequence listed in SEQ ID NO 1 to 14 or 108 to 111, preferably over the whole sequence;

(iii) a nucleic acid sequence that hybridizes to a nucleic acid sequence of (i) or (ii) under stringent conditions;

(iv) a fragment of any of the nucleic acid sequences of (i) to (iii), that hybridizes to a nucleic acid sequence of (i) or (ii) under stringent conditions; and (v) a nucleic acid sequence, wherein said nucleic acid sequence is derivable by substitution, addition and/or deletion of one of the nucleic acids of (i) to (iv) that hybridizes to a nucleic acid sequence of (i) or (ii) under stringent conditions, wherein the nucleic acid sequence encodes a polypeptide having N-methyl transferase activity.

It was surprisingly found that the above nucleic acids encode the first enzymes to N-methylate the backbone of (poly)peptides/ribosomally synthesized (poly)peptides. The encoded enzymes define a new natural product (RiPP) class involved in the biosynthesis of the nematotoxin Omphalotin A.

It was found that the genome of *O. olearius* encompasses a gene containing a nucleic acid sequence that encodes the 12 amino acids of the omphalotin core peptide, followed by an additional six amino acids at the C-terminus and an N-terminal domain displaying homology to methyltransferases (hereinafter the methyl transferase and omphalotin core peptide gene is referred to as the omphalotin precursor gene, see FIG. 2). The omphalotin precursor gene is part of a gene cluster encoding a prolyl oligopeptidase (2090, SEQ ID NOs: 29, 30, 36 and 37), which cleaves and cyclizes the omphalotin peptide. In addition, two P450 monooxygenases (2085, SEQ ID NOs: 31 and 38; and 2089, SEQ ID NOs: 33, 34, 40 and 41), an O-acyl transferase (2088, SEQ ID NOs: 32 and 39) and an oxidoreductase (2091, SEQ ID NOs: 35 and 42) reside in the same gene cluster, which contribute to the further modifications found in omphalotin variants B-I (see FIGS. 1 and 3). Similar gene clusters encoding methyl transferase genes were also identified in other fungi, e.g. *D. bispora, L. edodes* and *F. mediterranea* (FIGS. 3 and 4).

The term "% (percent) identity" as known to the skilled artisan and used herein in the context of nucleic acids indicates the degree of relatedness among two or more nucleic acid molecules that is determined by agreement among the sequences. The percentage of "identity" is the result of the percentage of identical regions in two or more sequences while taking into consideration the gaps and other sequence peculiarities.

The identity of related nucleic acid molecules can be determined with the assistance of known methods. In general, special computer programs are employed that use algorithms adapted to accommodate the specific needs of this task. Preferred methods for determining identity begin with the generation of the largest degree of identity among the sequences to be compared. Preferred computer programs for determining the identity among two nucleic acid sequences comprise, but are not limited to, BLASTN (Altschul et al., (1990) J. Mol. Biol., 215:403-410) and LALIGN (Huang and Miller, (1991) Adv. Appl. Math., 12:337-357). The BLAST programs can be obtained from the National Center for Biotechnology Information (NCBI) and from other sources (BLAST handbook, Altschul et al., NCB NLM NIH Bethesda, Md. 20894).

The nucleic acid molecules according to the invention may be prepared synthetically by methods well-known to the skilled person, but also may be isolated from suitable DNA libraries and other publicly available sources of nucleic acids and subsequently may optionally be mutated. The preparation of such libraries or mutations is well-known to the person skilled in the art.

In a preferred embodiment, the nucleic acid molecules of the invention are cDNA, genomic DNA, synthetic DNA, RNA or PNA, either double-stranded or single-stranded (i.e. either a sense or an anti-sense strand). The nucleic acid molecules and fragments thereof, which are encompassed within the scope of the invention, may be produced by, for example, polymerase chain reaction (PCR) or generated synthetically using DNA synthesis or by reverse transcription using mRNA from *O. olearius, D. bispora, L. edodes* or *F. mediterranea*.

In some instances, the present invention also provides novel nucleic acids encoding the (poly)peptides of the present invention characterized in that they have the ability to hybridize to a specifically referenced nucleic acid sequence, preferably under stringent conditions. Next to common and/or standard protocols in the prior art for determining the ability to hybridize to a specifically referenced nucleic acid sequence under stringent conditions (e.g. Sambrook and Russell, (2001) Molecular cloning: A laboratory manual (3 volumes)), it is preferred to analyze and determine the ability to hybridize to a specifically referenced nucleic acid sequence under stringent conditions by comparing the nucleotide sequences, which may be found in gene databases with alignment tools, such as e.g. the above-mentioned BLASTN (Altschul et al., (1990) J. Mol. Biol., 215:403-410), LALIGN alignment tools and multiple alignment tools such as e.g. CLUSTALW (Sievers F et al., (2011) Mol. Sys. Bio. 7: 539), MUSCLE (Edgar, (2004) Nucl. Acids Res. 32:1792-7) or T-COFFEE (Notredame et al., (2000) J of Mol. Bio 302 1: 205-17).

Most preferably, the ability of a nucleic acid of the present invention to hybridize to a nucleic acid, e.g. those listed in any of SEQ ID NOs 1 to 14 or 108 to 111, is confirmed in a Southern blot assay under the following conditions: 6× sodium chloride/sodium citrate (SSC) at 45° C. followed by a wash in 0.2×SSC, 0.1% SDS at 65° C. Further preferred stringent conditions are selected from the group consisting of (a) 0.15 M NaCl/0.0015 M sodium citrate/0.1% SDS at 50° C. for washing, (b) 50% (vol/vol) formamide with 0.1% bovine serum albumin/0.1% Ficoll/0.1% polyvinylpyrrolidone/50 mM sodium phosphate buffer at pH 6.5 with 750 mM NaCl and 75 mM sodium citrate at 42° C. during hybridization, and (c) hybridization in 50% formamide, 5×SSC, 5×Denhardt's solution, 50 g/mL sonicated salmon perm DNA, 0.1% SDS, and 10% dextran sulfate at 42° C., with washes at 42° C. in 0.2×SSC and 0.1% SDS.

The nucleic acid of the present invention preferably encodes a polypeptide having N-methyl transferase activity for methylating peptidic backbone amides, preferably for multiply methylating peptidic backbone amides, more preferably for multiply methylating peptidic backbone amides of hydrophobic residues, in particular residues valine, glycine, and isoleucine (VGI). A method for confirming N-methyl transferase activity for methylating peptidic backbone amides is described further below.

The term "nucleic acid encoding a polypeptide" as used in the context of the present invention is meant to include allelic variations and redundancies in the genetic code.

In a preferred embodiment, reflecting the current US patent practice with regard to the patentability of products by nature, the nucleic acids of the present invention do not encode a naturally occurring methyl transferase, preferably do not encode a methyl transferase encoded by an omphalotin gene cluster selected from the group consisting of omphalotin gene clusters from *O. olearius, D. bispora, L. edodes* and *F. mediterranea*. More preferably, the claimed nucleic acids exclude any nucleic acid sequence selected from the group consisting of nucleic acid sequences SEQ ID NOs: 1 to 14 and 108 to 111, preferably SEQ ID NOs: 1, 3, 5, 7, 9, 11 and 13.

In a most preferred embodiment, the nucleic acid of the present invention further comprises a nucleic acid sequence encoding a (poly)peptide for N-methylation by the N-methyl transferase encoded by the nucleic acid of the invention. It is preferred that the nucleic acid of the present invention encodes a fusion protein with the methyl transferase domain at the N-terminus and the (poly)peptide for N-methylation at the C-terminus, optionally together with further amino acids at the C- and/or N-terminus and/or bridging the methyl transferase and the (poly)peptide for N-methylation. Preferred examples for fusion proteins comprising a methyl transferase domain according to the present invention and varying (poly)peptides for N-methylation are provided below. For example, the omphalotin peptide sequence (i.e. the sequence of the precursor peptide that is subject to N-methylation) can be exchanged for an omphalotin peptide sequence without follower sequence, for an omphalotin peptide sequence with an upstream TEV cleavage site or for a CycA, KenA, R1 and/or DicA peptide sequence. Specific experimental data for the aforementioned fusion proteins are provided in Example 6 and FIGS. 8 and 9. Said data demonstrate the robustness and versatility of the fusion proteins having methyl transferase activity according to the present invention and show that (i) the substrate for the methyl transferase can be varied largely in size and amino acid composition, (ii) a cleavage site, e.g. a TEV cleavage site, for separating the fusion proteins after methylation can be introduced into the fusion protein without hampering the methyl transferase efficacy, and (iii) that peptides can be methylated without a follower sequence.

The term "(poly)peptide for N-methylation" as used herein encompasses oligopeptides featuring 2 to 10 amino acids as well as polypeptides featuring more than 10 amino acids. The (poly)peptides for N-methylation for practicing the present invention preferably have 4 to 24, 6 to 20, or 8 to 16, more preferably 10 to 14, most preferably about 12 amino acids.

The nucleic acid of the present invention is preferably operably linked to a promoter that governs expression in suitable vectors and/or host cells producing the polypeptides of the present invention in vitro or in vivo.

Suitable promoters for operable linkage to the isolated and purified nucleic acid are known in the art. In a preferred embodiment the nucleic acid of the present invention is one that is operably linked to a promoter selected from the group consisting of the *Pichia pastoris* AOX1 promoter (see for example *Pichia* Expression Kit Instruction Manual, Invitrogen Corporation, Carlsbad, Calif.), the *Saccharomyces cerevisiae* GAL1, ADH1, GAP, ADH2, MET25, GPD, CUP1 or TEF promoter (see for example Methods in Enzymology, 350, 248, 2002), the Baculovirus polyhedrin p10 or ie1 promoter (see for example Bac-to-Bac Expression Kit Handbook, Invitrogen Corporation, Carlsbad, Calif., and Novagen Insect Cell Expression Manual, Merck Chemicals Ltd., Nottingham, UK), the Lentivirus CMV, UbC, EF1α, or MSCV promoter (see for example System Biosciences, Mountain View, Calif., USA), the Adenovirus CMV promoter (see for example ViraPower Adenoviral Expression System, Life Technologies, Carlsbad, Calif., USA), the *E. coli* T7, araBAD, rhaP BAD, tetA, lac, trc, tac or pL promoter (see Applied Microbiology and Biotechnology, 72, 211, 2006), the *B. subtilis*, vegI, vegII, $\sigma_A$, $P_{grac}$, $P_{glv}$, manP or P43 promoter (see Applied Microbiology and Biotechnology, 72, 211, 2006), the plant CaMV35S, ocs, nos, Adh-1, Tet promoters (see e.g. Lau and Sun, Biotechnol Adv. 2009, 27, 1015-22) or inducible promoters for mammalian cells as described in Sambrook and Russell (2001).

Preferably, the isolated and purified nucleic acid is in the form of a recombinant vector, such as an episomal or viral vector. The selection of a suitable vector and expression control sequences as well as vector construction are within the ordinary skill in the art. Preferably, the viral vector is a lentivirus vector (see for example System Biosciences, Mountain View, Calif., USA), adenovirus vector (see for example ViraPower Adenoviral Expression System, Life Technologies, Carlsbad, Calif., USA), baculovirus vector (see for example Bac-to-Bac Expression Kit Handbook, Invitrogen Corporation, Carlsbad, Calif.), bacterial vector (see for example Novagen, Darmstadt, Germany)) or yeast vector (see for example ATCC Manassas, Va.). Vector construction, including the operable linkage of a coding sequence with a promoter and other expression control sequences, is within the ordinary skill in the art.

Hence and in a further aspect, the present invention relates to a recombinant vector, comprising one or more nucleic acids of the invention.

A further aspect of the present invention is directed to a host cell comprising a nucleic acid and/or a vector of the invention and preferably producing polypeptides of the invention. Preferred host cells for producing the polypeptide of the invention are selected from the group consisting of yeast cells, preferably *Saccharomyces cerevisiae* (see for example Methods in Enzmology, 350, 248, 2002), *Pichia pastoris* cells (see for example *Pichia* Expression Kit Instruction Manual, Invitrogen Corporation, Carlsbad, Calif.)], bacterial cells preferably *E. coli* cells (BL21(DE3), K-12 and derivatives) (see for example Applied Microbiology and Biotechnology, 72, 211, 2006) or *B. subtilis* cells (1012 wild type, 168 Marburg or WB800N)(see for example Westers et al., (2004) Mol. Cell. Res. Volume 1694, Issues 1-3 P: 299-310), plant cells, preferably *Nicotiana tabacum* or *Physcomitrella patens* (see e.g. Lau and Sun, Biotechnol Adv. 2009 May 18. [electronic publication ahead of print]), NIH-3T3 mammalian cells (see for example Sambrook and Russell, 2001) and insect cells, preferably sf9 insect cells (see for example Bac-to-Bac Expression Kit Handbook, Invitrogen Corporation, Carlsbad, Calif.).

Another important aspect of the present invention is directed to a preferably isolated and purified polypeptide selected from the group consisting of:

(a) polypeptides having an amino acid sequence selected from the group consisting of SEQ ID NOs: 15-28 and 112 to 115, preferably SEQ ID NO: 16, 18, 20, 22, 24, 26, 28 and 112, more preferably SEQ ID NOs: 15 and 16.

(b) polypeptides encoded by a nucleic acid of the present invention, (c) polypeptides having an amino acid sequence identity of at least 50, preferably at least 54, 60, 65, 70, 75, 80 or 85%, preferably at least 90, 91, 92, 93, 94 or 95% with the polypeptides of (a) and/or (b), (d) a functional fragment and/or functional derivative of (a), (b) or (c), wherein the polypeptide has N-methyl transferase activity.

The polypeptide of the present invention preferably has N-methyl transferase activity for methylating peptidic backbone amides, preferably for multiply methylating peptidic backbone amides, more preferably multiply methylating peptide backbone amides of hydrophobic residues, in particular residues valine, glycine, and isoleucine (VGI).

The N-methyl transferase activity can be easily assayed and confirmed, e.g. by contacting the polypeptide suspected of N-methyl transferase activity with a suitable substrate (poly)peptide for N-methylation, e.g. WVIVVGVIGVIG (SEQ ID NO: 63), under suitable conditions. Identifying N-methylation, preferably in the backbone of the (poly) peptide substrate, e.g. by mass spectroscopy, NMR spectroscopy, etc. confirms enzymatic activity. For example, suitable conditions are presented in Example 6 below.

The identity of related amino acid molecules can be determined with the assistance of known methods. In general, special computer programs are employed that use algorithms adapted to accommodate the specific needs of this task. Preferred methods for determining identity begin with the generation of the largest degree of identity among the sequences to be compared. Preferred computer programs for determining the identity among two amino acid sequences comprise, but are not limited to, TBLASTN, BLASTP, BLASTX, TBLASTX (Altschul et al., (1990) J. Mol. Biol., 215, 403-410), ClustalW (Larkin M A et al., Bioinformatics, 23, 2947-2948, 2007) or PHYRE2 (Kelley L A et al., (2015) Nature Protocols 10, 845-858). The BLAST programs can be obtained from the National Center for Biotechnology Information (NCBI) and from other sources (BLAST handbook, Altschul et al., NCB NLM NIH Bethesda, Md. 20894). The ClustalW program can be obtained from clustal.org and the PHYRE2 program.

The term “functional derivative” of a polypeptide of the present invention is meant to include any polypeptide or fragment thereof that has been chemically or genetically modified in its amino acid sequence, e.g. by addition, substitution and/or deletion of amino acid residue(s) and/or has been chemically modified in at least one of its atoms and/or functional chemical groups, e.g. by additions, deletions, rearrangement, oxidation, reduction, etc. as long as the derivative still has at least some methyl transferase activity to a measurable extent, e.g. of at least about 1 to 10% methyl transferase activity of the original unmodified polypeptide of the invention, e.g. SEQ ID NOs: 15 to 28 or 112 to 115.

In this context a “functional fragment” of the invention is one that forms part of a polypeptide or derivative of the invention and still has at least some methyl transferase activity to a measurable extent, e.g. of at least about 1 to 10% methyl transferase activity of the original unmodified polypeptide of the invention, e.g. SEQ ID NOs: 15 to 28 or 112 to 115.

The term “isolated and purified polypeptide” as used herein refers to a polypeptide or a peptide fragment which either has no naturally-occurring counterpart (e.g., a peptide mimetic), or has been separated or purified from components which naturally accompany it, e.g. in *O. olearius, D. bispora, L. edodes, F. mediterranea* or a fraction thereof. Preferably, a polypeptide is considered “isolated and purified” when it makes up for at least 60% (w/w) of a dry preparation, thus being free from most naturally-occurring polypeptides and/or organic molecules with which it is naturally associated. Preferably, a polypeptide of the invention makes up for at least 80%, more preferably at least 90%, and most preferably at least 99% (w/w) of a dry preparation. More preferred are polypeptides according to the invention that make up for at least at least 80%, more preferably at least 90%, and most preferably at least 99% (w/w) of a dry polypeptide preparation. Chemically synthesized polypeptides are by nature “isolated and purified” within the above context.

An isolated polypeptide of the invention may be obtained, for example, by extraction from *O. olearius, D. bispora, L. edodes* or *F. mediterranea*; by expression of a recombinant nucleic acid encoding the polypeptide in a host, preferably a heterologous host; or by chemical synthesis. A polypeptide that is produced in a cellular system being different from the source from which it naturally originates is “isolated and purified”, because it is separated from components which naturally accompany it. The extent of isolation and/or purity can be measured by any appropriate method, e.g. column chromatography, polyacrylamide gel electrophoresis, HPLC analysis, NMR spectroscopy, gas liquid chromatography, or mass spectrometry.

In a preferred embodiment, reflecting the current US patent practice with regard to the patentability of products of nature, the polypeptides of the present invention are not a naturally occurring methyl transferase, preferably are not a methyl transferase encoded by an omphalotin gene cluster selected from the group consisting of omphalotin gene clusters from *O. olearius, D. bispora, L. edodes* and *F. mediterranea*. More preferably the polypeptide does not consist of an amino acid sequence selected from the group consisting of amino acid sequences of SEQ ID NOs: SEQ ID NOs: 15 to 28 and 112 to 115, preferably 15, 17, 19, 21, 23, 25 and 27.

The methyl transferase of the present invention can, and preferably is present, e.g. expressed, together with the substrate (poly)peptide for N-methylation. Hence, the enzyme and its substrate form a fusion polypeptide, wherein the enzyme and its substrate may be separated by further bridging amino acids and the fusion protein may also comprise further amino acids at the C-terminus or N-terminus.

In a preferred embodiment, the present invention is also directed to a fusion polypeptide comprising a first polypeptide sequence encoding a methyl transferase according to the invention, and at least a second (poly)peptide sequence as substrate for N-methylation by the N-methyl transferase activity of the first polypeptide sequence.

Of course, the methyl transferase or a corresponding methyl transferase fusion protein of the present invention can also methylate (poly)peptide substrates without being fused to them, e.g. by contacting the enzyme and the substrate under typical physiological conditions allowing for enzyme activity.

Furthermore, in one aspect the present invention relates to antibodies, functional fragments and functional derivatives thereof or antibody-like binding proteins that specifically bind a polypeptide of the invention. As used herein, the term antibody is meant to include whole antibodies, functional fragments and functional derivatives thereof that specifically bind a polypeptide of the invention. These are routinely available by hybridoma technology (Kohler and Milstein, Nature 256, 495-497, 1975), antibody phage display (Winter et al., (1994) Annu. Rev. Immunol. 12, 433-455), ribosome display (Schaffitzel et al., (1999) J. Immunol. Methods, 231, 119-135) and iterative colony filter screening (Giovannoni et al., (2001) Nucleic Acids Res. 29, E27) once the target antigen is available. Typical proteases for fragmenting antibodies into functional products are well-known. Other fragmentation techniques can be used as well as long as the resulting fragment has a specific high affinity and, preferably a dissociation constant in the micromolar to picomolar range.

A very convenient antibody fragment for targeting applications is the single-chain Fv fragment, in which a variable heavy and a variable light domain are joined together by a polypeptide linker. Other antibody fragments for identifying the polypeptide of the present invention include Fab fragments, $Fab_2$ fragments, miniantibodies (also called small immune proteins), tandem scFv-scFv fusions as well as scFv fusions with suitable domains (e.g. with the Fc portion of an immuneglobulin). For a review on certain antibody formats, see Holliger P, Hudson P J; Engineered antibody fragments and the rise of single domains. Nat Biotechnol. 2005 Sep., 23(9):1126-36).

The term "functional derivative" of an antibody for use in the present invention is meant to include any antibody or fragment thereof that has been chemically or genetically modified in its amino acid sequence, e.g. by addition, substitution and/or deletion of amino acid residue(s) and/or has been chemically modified in at least one of its atoms and/or functional chemical groups, e.g. by additions, deletions, rearrangement, oxidation, reduction, etc. as long as the derivative has substantially the same binding affinity as to its original antigen and, preferably, has a dissociation constant in the micro-, nano- or picomolar range.

In a preferred embodiment, the antibody, fragment or functional derivative thereof for use in the invention is one that is selected from the group consisting of polyclonal antibodies, monoclonal antibodies, chimeric antibodies, humanized antibodies, CDR-grafted antibodies, Fv-fragments, Fab-fragments and $Fab_2$-fragments and antibody-like binding proteins, e.g. affilines, anticalines and aptamers.

For a review of antibody-like binding proteins see Binz et al. on engineering binding proteins from non-immunoglobulin domains in Nature Biotechnology, Vol. 23, No. 10, October 2005, Ser. No. 12/571,268. The term "aptamer" describes nucleic acids that bind to a polypeptide with high affinity. Aptamers can be isolated from a large pool of different single-stranded RNA molecules by selection methods such as SELEX (see, e.g., Jayasena, Clin. Chem., 45, p. 1628-1650, (1999); Klug and Famulok, M. Mol. Biol. Rep., 20, p. 97-107 (1994); U.S. Pat. No. 5,582,981). Aptamers can also be synthesized and selected in their mirror form, for example, as the L-ribonucleotide (Nolte et al., (1996) Nat. Biotechnol., 14, pp. 1116-1119; Klussmann et al., (1996) Nat. Biotechnol. 14, p. 1112-1115). Forms isolated in this way have the advantage that they are not degraded by naturally occurring ribonucleases and, therefore, have a greater stability.

Another antibody-like binding protein and alternative to classical antibodies are the so-called "protein scaffolds", for example, anticalines, that are based on lipocaline (Beste et al., (1999) Proc. Natl. Acad. Sci. USA, 96, p. 1898-1903). The natural ligand binding sites of lipocalines, for example, of the retinol-binding protein or bilin-binding protein, can be changed, for example, by employing a "combinatorial protein design" approach, and in such a way that they bind selected haptens (Skerra, (2000) Biochem. Biophys. Acta, 1482, pp. 337-350). For other protein scaffolds it is also known that they are alternatives for antibodies (Skerra, (2000) J. Mol. Recognit, 13, pp. 167-287; Hey, (2005) Trends in Biotechnology, 23, pp. 514-522).

In summary, the term functional antibody derivative is meant to include the above protein-derived alternatives for antibodies, i.e. antibody-like binding proteins, e.g. affilines, anticalines and aptamers that specifically recognize a polypeptide, fragment or derivative thereof.

A further aspect relates to a hybridoma cell line, expressing a monoclonal antibody according to the invention.

The nucleic acids, vectors, host cells, polypeptides and antibodies of the present invention have a number of new applications.

In a further aspect, the present invention is directed to the use of a vector, a host cell and/or a polypeptide according to the invention for producing an N-methylated, preferably a backbone N-methylated (poly)peptide.

In another aspect, the present invention relates to a method for producing an N-methylated (poly)peptide, preferably a backbone N-methylated (poly)peptide, more preferably a multiply backbone N-methylated (poly)peptide, most preferably a multiply N-methylated (poly)peptide backbone of hydrophobic residues (VGI) comprising the steps of:

(a) providing a polypeptide having methyl transferase activity according to the present invention (termed hereinafter "MT"),
(b) providing a (poly)peptide for N-methylation (termed hereinafter "substrate"),
(c) contacting the polypeptide having methyl transferase activity (MT) of (a) and the (poly)peptide for N-methylation (substrate) of (b) under conditions that allow for N-methylation,
(d) optionally cyclisation of the methylated peptide,
(e) optionally further modifying the N-methylated (poly) peptide,
(f) optionally cleaving the methylated peptide from the precursor,
(g) optionally at least partially purifying the N-methylated (poly)peptide.

In a preferred embodiment, the MT of step (a) and/or the substrate of step (b) are provided by a vector and/or a host cell according to the present invention.

In a further preferred embodiment, the MT of step (a) and the substrate of step (b) are provided as a single fusion protein according to the present invention or as separate entities, preferably as a single fusion protein.

In yet another preferred embodiment, the conditions in step (c) allow for in vivo or in vitro N-methylation.

Preferably, the MT and the substrate are contacted intracellularly, more preferably expressed as a fusion protein or co-expressed in the same host cell, and the substrate is methylated within the host cell, preferably within *E. coli* or *S. cerevisiae.*

There are many further enzymes suited for modifying (poly)peptide substrates that can be used to further modify a substrate for use in the present invention before or after the N-methylation step.

In a very preferred embodiment the method according to the present invention is one, wherein in steps (d) and/or (e) at least one further enzyme and/or protein is added for further modifying the N-methylated (poly)peptide, preferably further enzymes and proteins selected from the group consisting of prolyl oligopeptidase (POP), monooxygenase, preferably P450 monooxygenase, O-acyl transferase, oxidoreductase, aldo/keto reductase, aspartic peptidase, and serine-type peptidase, more preferably enzymes having an amino acid sequence according to any one of SEQ ID NOs: 36 to 42, and 53 to 58 or functional fragments or functional derivatives thereof.

The method of the present invention can also be varied by modifying the substrate prior to N-methylation by the polypeptide of the invention, e.g. by the above referenced enzymes.

Preferably, in step (g) the at least partially purifying of the N-methylated (poly)peptide is accomplished using ammonium sulfate precipitation or general chromatography procedures such as anionic and cationic affinity chromatography, hydrophobic interaction chromatography or size-exclusion chromatography (e.g. see: Protein and peptide purification Technique selection guide (GE Healthcare, UK) or Sterner et al., (1997) Nat. Prod. Let. Volume 10, issue 1).

The peptide can also be purified exploiting genetically introduced peptide or protein tags using affinity chromatography. Preferred affinity chromatography methods are metal affinity chromatography, strep-tag-strepta-vidin affinity chromatography, glutathione-GST affinity chromatography, maltose-MBP affinity chromatography or FLAG-antiFLAG affinity chromatography (e.g. see: Affinity Chromatography Principles and Methods (GE Healthcare, UK) or Terpe et al., (2003) Appl. Microbiol. Biotechnol 60:523-533).

The omphalotin A gene cluster is the first example of a ribosomally synthesized multiply backbone N-methylated (cyclic) peptide and founds a novel class of ribosmally synthesized and post-translationally modified peptides, so-called RiPPs (Arnison P G et al., (2013) Nat Prod Rep 30:108-160). The structural gene coding for omphalotin A is unique in that the leader peptide is the MT domain that is responsible for the N-methylation of the backbone amides of the core peptide. MT is the first example of an enzyme that reliably N-methylates amides of existing peptide bonds in a ribosomally synthesized peptide or protein.

The proteins and methods of the present invention for N-methylating substrates have utility in (poly)peptide drug discovery, research and development in that they can be easily and economically used for modifying the properties of potentially medically active substrates or to disassemble aggregates and fibrils of their corresponding native non-methylated sequences. Next to designing new (poly)peptide-based drugs the methyl transferase enzymes can modify or attach a methylated peptide to known (poly)peptide-based drugs and lead to improved target-specificity, efficacy, stability, improved pharmacokinetics and/or improved oral and intestinal membrane permeability.

The substrates for use in the present invention are not limited to specific amino acid sequences and can be varied widely. All they require is the presence of at least one amide bond in a (poly)peptide or (poly)peptide-like compound, e.g. a depsipeptide.

On the nucleic acid level, preferably forming part of the methyl transferase enzyme as a fusion protein, the substrate can be easily, preferably randomly varied to provide a whole library of potentially suitable substrates that can be screened for medical utility. Hence, the nucleic acids, polypeptides, vectors and/or host cells can form part of a screening assay for identifying medically active (poly)peptides.

In addition, it is a further objective of the present invention to provide new, alternative and/or improved enzymatic tools for modifying (poly)peptides.

In a further independent aspect, the above objective technical problem is solved by the provision of new fungal enzymes and proteins, preferably selected from the group consisting of prolyl oligopeptidase (POP), monooxygenase, preferably P450 monooxygenase, O-acyl transferase, oxidoreductase, aspartic peptidase and serine type peptidase.

The enzymes and/or proteins of the present invention are preferably derived from *O. olearius, D. bispora, L. edodes* or *F. mediterranea*. More preferably, these enzymes and/or proteins relate to a prolyl oligopeptidase (POP) derived from *O. olearius, D. bispora, L. edodes* or *F. mediterranea.*

In a first alternative aspect, the present invention relates to a preferably isolated and purified nucleic acid, comprising a nucleic acid sequence selected from the group consisting of:

(i) a nucleic acid sequence selected from the group consisting of nucleic acid sequences listed in SEQ ID NOs: 29, 43, 45 and 47 (2090, 765750, 144537, 801057 (complete POP genes);

(ii) a nucleic acid sequence of at least 60 or 70, 80 or 90% identity, preferably at least 95% identity, more preferred at least 98% identity with a nucleic acid sequence listed in SEQ ID 29, 30, 43-48, preferably SEQ ID NOs: 30, 44, 46 and 48, more preferably SEQ ID NOs: 29 and 30, preferably over the whole sequence;

(iii) a nucleic acid sequence that hybridizes to a nucleic acid sequence of (i) or (ii) under stringent conditions;

(iv) a fragment of any of the nucleic acid sequences of (i) to (iii), that hybridizes to a nucleic acid sequence of (i) or (ii) under stringent conditions; and (v) a nucleic acid sequence, wherein said nucleic acid sequence is derivable by substitution, addition and/or deletion of one of the nucleic acids of (i) to (iv) that hybridizes to a nucleic acid sequence of (i) or (ii) under stringent conditions, wherein the nucleic acid sequence encodes a prolyl oligopeptidase (POP).

In a preferred embodiment, the nucleic acid encoding POP is a DNA, RNA or PNA, preferably DNA or PNA, more preferably DNA.

In a further preferred embodiment, the above nucleic acid encodes a polypeptide having peptidase and/or cyclase activity for polypeptides, preferably N-methylated (poly) peptides, more preferably for backbone N-methylated peptides, most preferably for multiply backbone N-methylated (poly)peptides.

In a preferred embodiment, reflecting the current US patent practice with regard to the patentability of products by nature, the nucleic acids of the present invention do not encode a naturally occurring prolyl oligopeptidase, preferably do not encode a prolyl oligopeptidase encoded by an omphalotin gene cluster selected from the group consisting of omphalotin gene clusters from *O. olearius, D. bispora, L. edodes* and *F. mediterranea*. More preferably, the nucleic acid does not consist of a nucleic acid sequence selected from the group consisting of nucleic acid sequences SEQ ID NOs: 29, 30, 43-48, preferably 29, 43, 45 and 47.

In a further preferred embodiment, the present invention is directed to a recombinant vector comprising a nucleic acid encoding POP, preferably a viral or episomal vector, preferably a baculovirus vector, lentivirus vector, adenovirus vector, yeast or bacterial episomal vector.

In a further preferred embodiment, the present invention relates to a host cell comprising a nucleic acid encoding POP, or a vector of the present invention, preferably a host cell selected from the group consisting of yeast cells, preferably *Saccharomyces cerevisiae, Pichia pastoris* cells, *E. coli* cells, *B. subtilis* cells, plant cells, preferably *Nicotiana tabacum* or *Physcomitrella patens* cells, NIH-3T3 mammalian cells and insect cells, preferably sf9 insect cells.

In a further alternative aspect, the present invention is directed to a preferably isolated and purified polypeptide selected from the group consisting of:

(a) polypeptides having an amino acid sequence selected from the group consisting of SEQ ID NOs: 36, 37 and 53-58, preferably SEQ ID NOs: 37, 54, 56 and 58, more preferably 36 and 37, (b) POP polypeptides encoded by a nucleic acid of the present invention, (c) polypeptides having an amino acid sequence identity of at least 50 or 60%, at least 70 or 80%, preferably at least 90 or 95% with the polypeptides of (a) and/or (b), (d) a functional fragment and/or functional derivative of (a), (b) or (c), wherein the polypeptide has prolyl oligopeptidase activity.

In a preferred embodiment, the POP polypeptide has peptidase and/or cyclase activity for (poly)peptides, preferably N-methylated (poly)peptides, more preferably for backbone N-methylated peptides, most preferably for multiply backbone N-methylated (poly)peptides.

In a further preferred embodiment, the POP polypeptide is not a naturally occurring prolyl oligopeptidase, preferably is not a prolyl oligopeptidase encoded by an omphalotin gene cluster selected from the group consisting of omphalotin gene clusters from *O. olearius, D. bispora, L. edodes* and *F. mediterranea*. More preferably, the polypeptide does not consist of an amino acid sequence selected from the group consisting of amino acid sequences SEQ ID NOs: 36, 37 and 53 to 58, preferably 36, 53, 55 and 57.

In a further alternative aspect, the present invention provides an antibody, preferably a monoclonal antibody, a functional fragment or functional derivative thereof or an antibody-like binding compound that specifically binds a POP polypeptide of the present invention.

In yet another alternative aspect, the present invention relates to a hybridoma cell line, expressing a monoclonal antibody that specifically binds a POP polypeptide according to the present invention.

Also, the present invention is directed to the use of a vector, a host cell and/or a POP polypeptide according to the present invention for producing a cleaved and/or cyclized (poly)peptide.

In another alternative aspect, the present invention teaches a method for producing a cleaved and/or cyclized (poly)peptide, comprising the steps of:

(a) providing a polypeptide having prolyl oligopeptidase activity according to the present invention (termed hereinafter "POP"),
(b) providing a (poly)peptide for peptide cleavage and/or cyclization (termed hereinafter "POP substrate"),
(c) contacting the polypeptide having prolyl oligopeptidase activity of (a) and the (poly)peptide for peptide cleavage and/or cyclization of (b) under conditions that allow for cleavage and/or cyclization,
(d) optionally further modifying the cleaved and/or cyclized (poly)peptide,
(e) optionally at least partially purifying the cleaved and/or cyclized (poly)peptide.

Preferably, the POP of step (a) and/or the POP substrate of step (b) are provided by a vector and/or a host cell of the invention.

Preferably, in step (c), the conditions allow for intra- or extracellular cleavage and/or cyclization.

In a preferred embodiment the invention relates to a method, wherein in step (d) at least one further enzyme and/or protein is added for further modifying the cleaved and/or cyclized (poly)peptide, preferably further enzymes and proteins selected from the group consisting of methyl transferase (MT), preferably N-methyl transferase, more preferably backbone N-methyl transferase, monooxygenase, preferably P450 monooxygenase, O-acyl transferase, oxidoreductase, aldo/keto reductase, more preferably one or more enzymes having an amino acid sequence according to any one of SEQ ID Nos: 15 to 28, 112 to 115 and 38 to 42 or functional fragments or derivatives thereof.

In step (e), the at least partially purifying of the cleaved and/or cyclized (poly)peptide preferably comprises the same procedures identified above for at least partially purifying methyl transferase products.

In another aspect, the present invention is also directed to the (poly)peptide-modifying enzymes having nucleic acid and amino acid sequences listed in SEQ ID NOs: 31 to 35 and 38 to 42, respectively.

In a preferred embodiment, this aspect relates to a preferably isolated and purified nucleic acid, comprising a nucleic acid sequence selected from the group consisting of:

(i) a nucleic acid sequence selected from the group consisting of nucleic acid sequences listed in SEQ ID NOs: 31 to 35;
(ii) a nucleic acid sequence of at least 60 or 70, at least 80 or 90% identity, preferably at least 95% identity, more preferred at least 98% identity with a nucleic acid sequence listed in SEQ ID NO 31 to 35, preferably over the whole sequence;
(iii) a nucleic acid sequence that hybridizes to a nucleic acid sequence of (i) or (ii) under stringent conditions;
(iv) a fragment of any of the nucleic acid sequences of (i) to (iii), that hybridizes to a nucleic acid sequence of (i) or (ii) under stringent conditions; and
(v) a nucleic acid sequence, wherein said nucleic acid sequence is derivable by substitution, addition and/or deletion of one of the nucleic acids of (i) to (iv) that hybridizes to a nucleic acid sequence of (i) or (ii) under stringent conditions, wherein the nucleic acid sequence encodes a polypeptide having monooxygenase (SEQ ID NO: 31), O-acyl transferase (SEQ ID NO: 32), monoxygenase (SEQ ID NO: 33, 34), or oxidoreductase (SEQ ID NO: 35) activity.

In a second preferred embodiment, the present invention relates to an isolated and purified polypeptide selected from the group consisting of:

(a) polypeptides having an amino acid sequence selected from the group consisting of SEQ ID NOs: 38 to 42,
(b) polypeptides encoded by a nucleic acid of any of claims 1 to 5,
(c) polypeptides having an amino acid sequence identity of at least 50 or 60%, at least 70 or 80%, preferably at least 90 or 95% with the polypeptides of (a) and/or (b),
(d) a functional fragment and/or functional derivative of (a), (b) or (c), wherein the polypeptide has monooxygenase (SEQ ID NO: 38), O-acyl transferase (SEQ ID NO: 39), monoxygenase (SEQ ID NO: 40, 41), or oxidoreductase (SEQ ID NO: 42) activity.

Preferably, reflecting the current US patent practice with regard to the patentability of products by nature, the nucleic acids and amino acids of the present invention do not encode a naturally occurring (poly)peptide-modifying enzyme and/or protein, preferably do not encode an enzyme encoded by an omphalotin gene cluster selected from the group consisting of omphalotin gene clusters from *O. olearius, D. bispora, L. edodes* and *F. mediterranea*. More preferably, the nucleic and amino acid does not consist of a nucleic acid or amino acid sequence selected from the group consisting of nucleic acid and amino acid sequences SEQ ID NOs: 31-35 and 38-42.

The here-described novel monooxygenase (SEQ ID NO: 31), O-acyl transferase (SEQ ID NO: 32), monoxygenase (SEQ ID NO: 33, 34), and oxidoreductase (SEQ ID NO: 35) and their nucleic and amino acid derivatives can form part of a recombinant vector, a host cell, a fusion protein or have utility in methods as described above for the inventive MT and POP enzymes for modifying (poly)peptides, preferably for modifying methylated and/or cyclized (poly)peptide substrates.

In this regard, it is noted that the definitions provided in the context of the methyl transferase (MT) enzymes above and generally relating to the nature of nucleic acids, polypeptides and (poly)peptides, antibodies, hybridoma cells, vectors, host cells, nucleic acid and amino acid sequence identity, hybridization conditions, etc. are also valid for the prolyl oligopeptidase (POP) enzymes, the monooxygenase, O-acyl transferase, monoxygenase, and oxidoreductase enzymes. Moreover, the promoters, vectors, host cells, method parameters, etc. mentioned as preferred embodiments in the context of MT enzymes also form preferred embodiments for practicing the present invention with regard to the other enzymes.

In the following, the invention is illustrated by figures and specific examples, none of which are to be interpreted as limiting the scope of the invention as taught in the appended claims.

BRIEF DESCRIPTION OF DRAWINGS

FIG. 1 is a schematic overview of the natural N-methylation pattern of the nematicidal cyclic peptide omphalotin A (left) and its omphalotin variants B to I (right) (adapted from Büchel et al., (1998) Tetrahedron 54:5345-5352).

FIG. 2 shows a schematic bar (top) and corresponding sequence listing (below) illustrating the amino acid sequence of the omphalotin precursor according to SEQ ID NO: 15. The amino acids of the methyl transferase domain (underlined) show homology towards the tetrapyrrole (Corrin/Porphyrin) methylases (pfam: 00590), the amino acids in italic letters show weak homology towards the conserved domains of unknown function TrbG and YabN (PRK13885 and COG3956) and the amino acids in bold letters form omphalotin. Bold and underlined residues are involved in S-Adenosyl methionine (SAM) binding and compromise methylation when mutated to an alanine. For the protein sequence, see SEQ ID NO 15 and protein ID number: 2087 on the JGI website.

FIG. 3B is a tabular overview of the details of genes located in the *O. olearius* and *D. bispora* borosin gene clusters. The asterisk denotes that the protein sequences corresponding to the respective protein ID numbers can be found on the JGI website.

FIG. 4 is a comparative schematic overview of the OmpA gene cluster of *O. olearius* with further fungal homologous omphalotin gene clusters in *F. mediterranea*. The protein sequences corresponding to the respective protein ID numbers can be found on the JGI website.

FIG. 5A shows an alignment of the methyltransferase domain of the omphalotin precursor with other fungal homologues. Residues in black boxes highlight conserved residues and residues with similar properties are high-lighted in bolt. Sequence identity with the omphalotin precursor (2087) ranges from 89.42% (765759) to 54.36% (32310). Sequences of all homologues are according to SEQ ID NO: 15, 17, 19, 21, 23, 25 and 27 (aa MT only). FIG. 5B shows an alignment of the peptidase domain of the omphalotin prolyl oligopeptidase with the prolyl oligopeptidase of *D. bispora*. Sequence identity of the prolyl oliopeptidase from omphalotin with the peptidase from *D. bispora* is 87.86%. Sequences according to SEQ ID NOs: 37 and 54 (aa protease domains only). Alignment created with clustal Omega (Sievers F et al., (2011) Mol. Sys. Bio. 7: 539) and visualized using ESPript 3 (Robert X et al., (2014) Nucl. Acids Res. 42(W1):W320-W324).

FIGS. 8A, 8B, 8C and 8D lists methylated fragments of different variants of the omphalotin precursor (SEQ ID NOs: 99, 101 and 102) and the ten times methylated fragment of the *D. bispora* 765750 homologue (SEQ ID NO 100) observed by MS/MS data after different expression times in *E. coli* BL21. The omphalotin precursor was expressed for 1 or 5 days in *E. coli* BL21. The purified protein was digested by trypsin and subjected to LC-MS/MS. The MS-identified trypsin fragments containing the omphalotin core peptide are listed. The top fragment shows where methylations (underlined) are expected in the peptide (bold) of the naturally isolated omphalotins. The fragments below were found experimentally, the third fragment (italic letters) was the most abundant after 1 day of expression. Underlining means that this amino acid was found to be methylated according to the MS/MS data.

FIG. 9 shows the N-methylation pattern of therapeutic peptides produced with the methyltransferase of *O. olearius*. The top line (1) illustrates the natural N-methylation pattern of the cyclic non-ribosomal immunosuppressant cyclosporine A, and the natural N-methylation pattern of the cyclin-dependent kinase 4 inhibitor dictyonamide A. Line (7) shows the natural N-methylated synthetic antimalarial R1 peptide and kendarimide which reverses P-glycoprotein-mediated multidrug resistance in tumor cells. The following bottom columns (2) to (6) and (8) to (10) show the patterns of N-methylation observed after 5 days of in vivo *E. coli* expression at 16° C. when the omphalotin encoding peptide in the precursor was exchanged with the peptide sequences that resembled cyclosporin A (line (1) left, SEQ ID NO: 103), dictyanomide A (line (1) middle, SEQ ID NO: 104), R1 (line (7) left, SEQ ID NO: 105) or kendarimide, (line (7) right, SEQ ID NOs: 106) thus demonstrating general substrate applicability for methylation by the methyl transferase.

DETAILED DESCRIPTION OF THE INVENTION

EXAMPLES

Figure 3A:
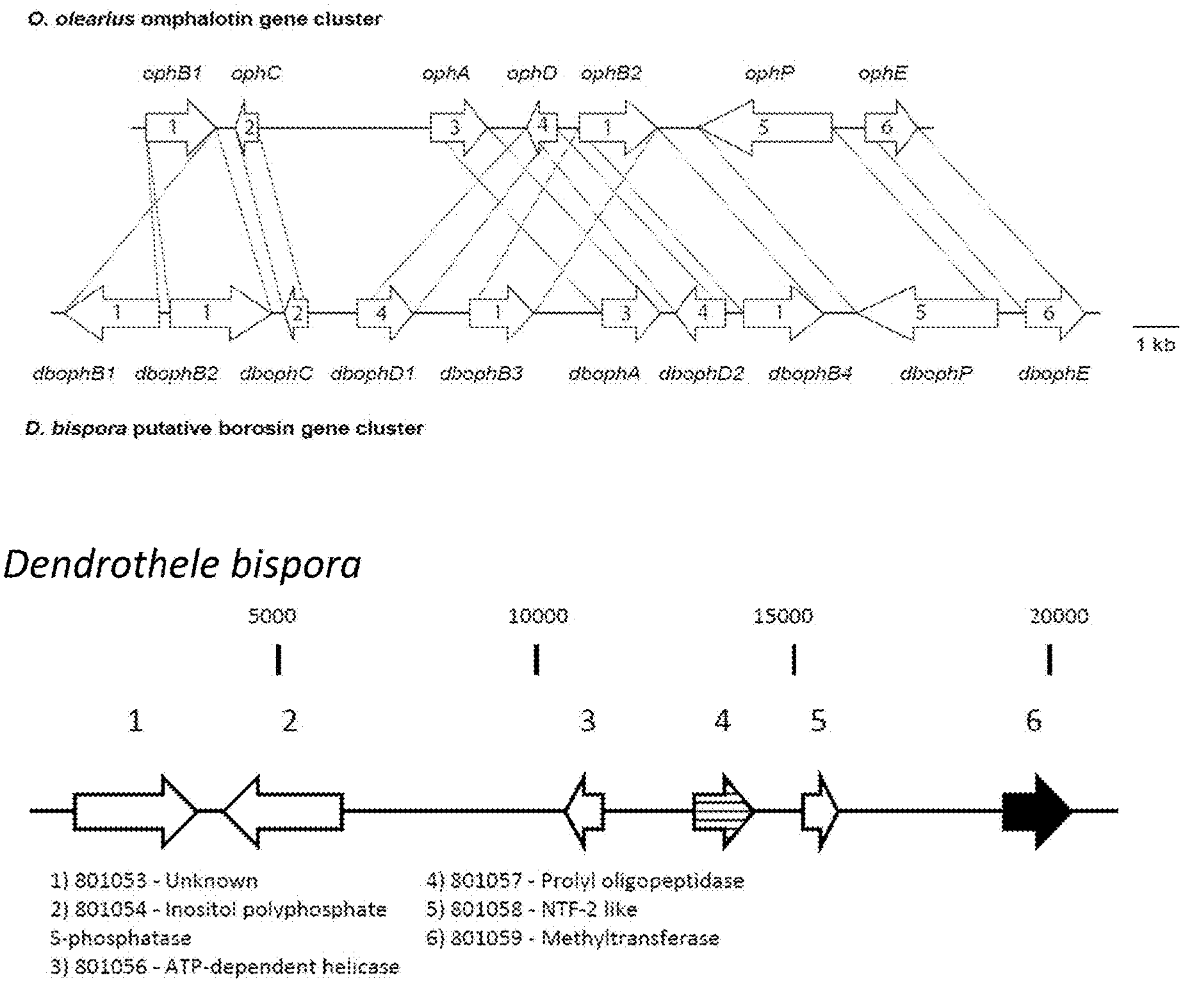
FIG. 3A is a comparative schematic overview of the OmpA gene cluster of *O. olearius* with further fungal homologous omphalotin gene clusters in *D. bispora*. The gene cluster of *O. olearius* consists of (i) the methyltransferase (MT) encoding the omphalotin peptide (2087, SEQ ID NOs: 1 and 15), the prolyl oligopeptidase (POP) (2090, SEQ ID NO: 29 and 36), which is involved in cleavage of the omphalotin peptide from the precursor and the cyclisation reaction. In addition, two monooxygenases (2085, SEQ ID NOs: 31, 38; and 2089, SEQ ID NOs: 33, 40; and 2089Late start, SEQ ID NOs: 34, 41), an O-acyl transferase (2088, SEQ ID NOs: 32, 39), and an oxidoreductase (2091, SEQ ID NOs: 35, 42) are shown that are involved in the modifications of omphalotin variants B to I. The protein sequence of the OmpA gene cluster with the respective protein ID numbers can be found on the JGI website.
Figure 6:
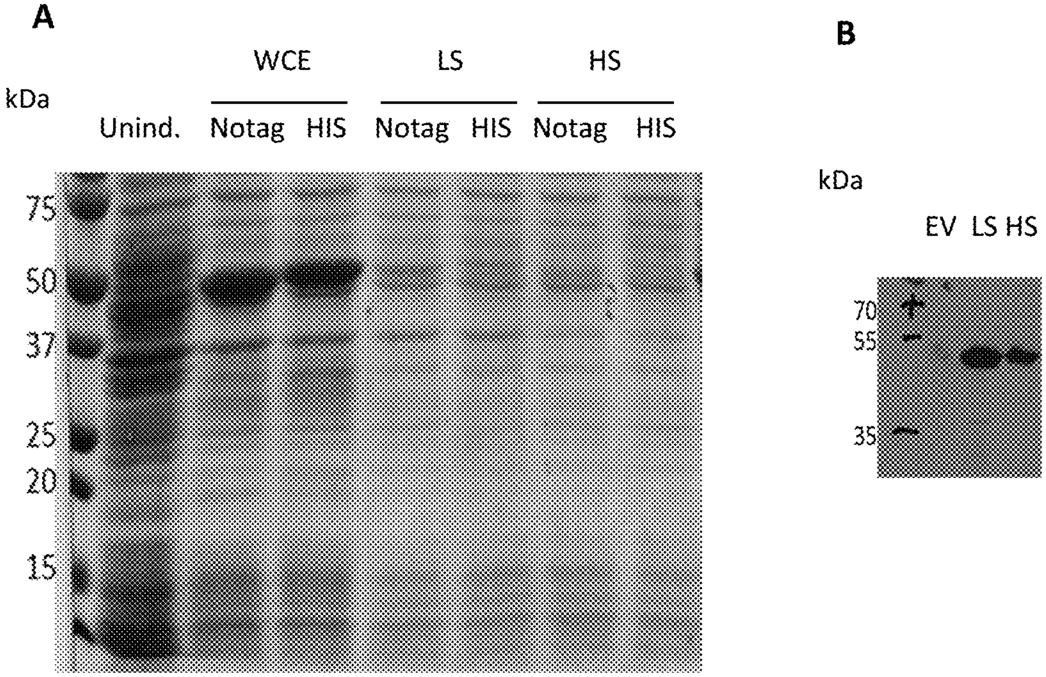
FIG. 6 shows SDS-PAGE gels and immuno detections for confirming the expression and solubility of the omphalotin precursor in *E. coli* BL21. Gel A shows a whole cell extract (WCE) of *E. coli* BL21 that was not induced (lane 1), expressing the non-tagged omphalotin precursor (lanes 2, 4 and 6), or the N-terminally HIS-tagged omphalotin precursor (lanes 3, 5 and 7), when separated on a 12% SDS PAGE gel. Lanes 2 and 3 show the WCE before centrifugation, lane 4 and 5 the WCE after low spin (LS) centrifugation (5000×g 5 min) and lanes 6 and 7 after high spin (HS) centrifugation (15000×g 30 min). Gel B shows immuno-detection of the omphalotin precursor with an anti-HIS antibody (Qiagen, Switzerland). A WCE of *E. coli* BL21 expressing an empty vector (EV) was used as a control. Lane 2 shows the WCE after low spin centrifugation and lane 3 after high spin centrifugation. *E. coli* BL21 was induced for 24 hr with 0.2 mM IPTG at 16° C.
Figure 7:
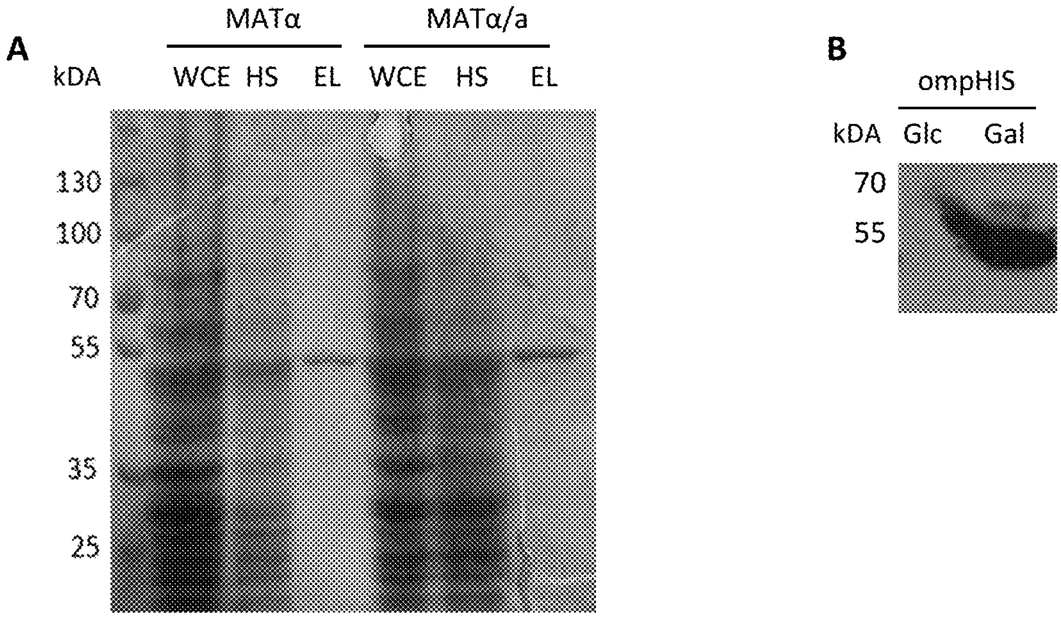
FIG. 7 shows SDS-PAGE gels and immuno detections for confirming the expression and solubility of the omphalotin precursor in *S. cerevisiae*. Gel A shows WCEs of *S. cerevisiae* W303 MATα (lane 1-3) or MATα/a (lane 3-6) grown for 3 hrs on YP galactose to induce expression of the N-terminally HIS-tagged omphalotin precursor. Lanes 1 and 4 show the WCE before centrifugation, lanes 2 and 5 the WCE after high spin centrifugation (16000 g for 30 min) and lanes 3 and 6 the purified protein after HIS tag purification. Gel B shows the immuno-detection of the omphalotin precursor with an anti-HIS tag antibody on a WCE of *S. cerevisiae* W303 MATα/a grown for 24 hr on galactose at 25° C. (lane 2). *S. cerevisiae* W303 MATα/a grown on glucose was used as a control (lane 1).

Example 1—cDNA Synthesis and Cloning of the Omphalotin Precursor

*O. olearius* strain DSM3398 (DSMZ, Germany) was used for RNA extraction and cDNA synthesis. *O. olearius* mycelium was grown on cellophane disks (Celloclair, Switzerland) on 1.5% (w/v) agar plates containing yeast maltose agar (0.4% (w/v) yeast extract (Oxoid AG, England), 1% (w/v) malt extract (Oxoid AG, England), 0.4% (w/v) glucose) for 5 days at 28° C. in the dark. To extract RNA, 8.2 mg of lyophilized mycelium was lysed with 8 mg of 0.5 mm glass beads in three FastPrep steps of 45 s at 4.5, 5.5 and 6.5, cooling the sample for 5 min on ice between each step. RNA was extracted with 1 ml Qiazol (Qiagen, Germany) and 0.2 ml chloroform. After a centrifugation at 12000×g and 4° C. for 15 min, RNA was recovered in the aqueous phase, washed on-column using the RNeasy Lipid Tissue Mini Kit (Qiagen, Germany) and eluted in RNase-free water. cDNA was synthesized from 1 μg of extracted RNA using the Transcriptor-first strand cDNA synthesis kit (Roche Applied Science, Germany) following the instructions of the manufacturer. The coding sequence of the omphalotin precursor was amplified from cDNA by PCR using Phusion high-fidelity DNA polymerase using standard protocols (Sambrook J, Russell D, 2001, Molecular cloning 3$^{rd}$ edition) using primers:

```
Forward primer:
                                     (SEQ ID NO: 64)
5'-ATGGAGACTTCCACTCAGAC-3'

Reverse primer:
                                     (SEQ ID NO: 65)
5'-TTATTCCGTGCTCATGACTG-3'.
```

An A-tailing reaction was performed on the PCR product after which it was cloned into the pGEM-T-easy vector (Promega, USA) and transformed to *E. coli* DH5α. A PCR on a plasmid containing the right cDNA sequence was performed using primers:

```
Forward primer:
                                     (SEQ ID NO: 66)
5'-GGGGGGCATATGGAGACTTCCACTCAGAC-3'

Forward primer:
                                     (SEQ ID NO: 67)
5'-TTTTTTCATATGGAGCATCATCATCATCATCATCATACT
TCCACTCAGACCAAAGCTGGCTCA-3'

Reverse primer:
                                     (SEQ ID NO: 68)
5'-CCCCCCGCGGCCGCTTATTCCGTGCTCATGACT-3'
```

after which the PCR products were cloned into pET24 (Novagen, Germany) using the restriction sites Ndel and Notl (Thermo Scientific, USA) and transformed to *E. coli* BL21 or cloned into the *S. cerevisiae* expression vector pRS426 (Sikorski R. S. el al., (1989) *Genetics* 122: 19-27S) using the restriction sites Spel and EcoRI.

Example 2 Cloning of the CycD, DicA, KenA and No Follower Omphalotin Variants An adapter ligation was performed to introduce a Bsal restriction site in the omphalotin precursor gene using primers:

```
Forward primer:
                                     (SEQ ID NO: 69)
5'-CATGAGACCTAGTCATGAGCACGGAATAAGC-3'

Reverse primer:
                                     (SEQ ID NO: 70)
5'-GGCCGCTTATTCCGTGCTCATGACTAGGTCT-3'
```

10 μl of each primer (100 μM) was added to 80 μl of 10 mM Tris pH 7.5. Primer annealing was performed with the following program: 5 min at 98° C. with cooling rate at 4° C./s, 30 seconds at 80° C. with cooling rate 0.01° C./s and 30 seconds at 40° C. with cooling rate 0.02° C./s. The annealed primers were phosphorylated and ligated into a pET24 vector containing the omphalotin precursor restricted with Ncol and Notl (Thermo Scientific, USA) at a vector-to-insert molar ratio of 1:7. To introduce the sequence encoding for CycD, DicA, KenA and to remove the follower an adapter ligation was performed with the following primers:

```
CycD forward primer:
                                     (SEQ ID NO: 71)
5'-AGGTCTCACCCACTGGTGCTGGCTGCACTGCTCGTCATCGTTGGTTC
AGTCATGAGCACGGAATAAGCGGCCGCA-3'

CycD reverse primer:
                                     (SEQ ID NO: 72)
5'-TGCGGCCGCTTATTCCGTGCTCATGACTGAACCAACGATGACGAGCA
GTGCAGCCAGCACCAGTGGGTGAGACCT-3'

DicA forward primer:
                                     (SEQ ID NO: 73)
5'-AGGTCTCACCCAGCAACGACCGTAGTAGTTGTTGTTATTGTGGGTTA
AGCGGCCGCA-3'

DicA reverse primer:
                                     (SEQ ID NO: 74)
5'-TGCGGCCGCTTAACCCACAATAACAACAACTACTACGGTCGTTGCTG
GGTGAGACCT-3'

Ken A forward primer:
                                     (SEQ ID NO: 75)
5'-AGGTCTCACCCACAGTTCATTGCCGTTGTAGTTGTGGCAGTCGTGTG
CTGTTTCTAAGCGGCCGCA-3'

Ken A reverse primer:
                                     (SEQ ID NO: 76)
5'-TGCGGCCGCTTAGAAACAGCACACGACTGCCACAACTACAACGGCAA
TGAACTGTGGGTGAGACCT-3'

No follower forward primer:
                                     (SEQ ID NO: 77)
5'-AGGTCTCACCCATGGGTCATCGTCGTTGGTGTTATCGGTGTCATCGG
ATAAGCGGCCGCA-3'

No follower reverse primer:
                                     (SEQ ID NO: 78)
5'-TGCGGCCGCTTATCCGATGACACCGATAACACCAACGACGATGACCC
ATGGGTGAGACCT-3'
```

Primer annealing was performed as described above, restricted using BsaI and NotI, purified using a Nucleospin gel and PCR cleanup kit (Macherey Nagel, Switzerland) and ligated in pET24 containing the omphalotin precursor that was restricted with BsaI.

Example 3 Cloning of OMP TEV, R1 and 765759

For replacement of the omphalotin peptide with that of R1 and to introduce a TEV cleavage site the following sequences were synthesized by Genscript (USA):

```
OMP TEV
                                        (SEQ ID NO 79)
5'-GGATCCCAAGGCACTCGCCGACTACAAAGCTGATCACCGCGCCTTTG
CTCAATCTGTCCCCGACTTGACGCCTCAGGAGCGTGCGGCTTTGGAGCTC
GGTGATTCGTGGGCTATTCGTTGCGCGATGAAGAATATGCCCTCGTCGCT
CTTGGACGCTGCTCGTGAATCCGGCGAAAACTTGTACTTCCAAGGTTTCC
CATGGGTCATCGTCGTTGGTGTTATCGGTGTCATCGGATAAGAATTC-
3'
OMP R1
                                        (SEQ ID NO 80)
5'-GGATCCCAAGGCACTCGCCGACTACAAAGCTGATCACCGCGCCTTTG
CTCAATCTGTCCCCGACTTGACGCCTCAGGAGCGTGCGGCTTTGGAGCTC
GGTGATTCGTGGGCTATTCGTTGCGCGATGAAGAATATGCCCTCGTCGCT
CTTGGACGCTGCTCGTGAATCCGGCGAAGAGGCATCCCAAAACGGTTTCC
CAGTCTTTGCAGAATTTCTGCCTCTGTTCAGCAAATTCGGTTCGCGGATG
CACATTCTGAAATAAGCGGCCGC-3'
```

The synthesized sequences were restricted with BamHI and EcoRI for OMP TEV and BamHI and NotI for R1, purified using a Nucleospin gel and PCR cleanup kit (Macherey Nagel, Switzerland) and ligated into pET24 containing the omphalotin precursor.

The sequence of 765759 from *D. bispora* was codon optimized for expression in *E. coli* and synthesized by Genscript (USA) SEQ ID NO 107. The synthesized sequence was restricted with HindIII and NdeI, purified using a Nucleospin gel and PCR cleanup kit (Macherey Nagel, Switzerland) and ligated into pET24 containing the omphalotin precursor.

Example 4—Expression and Purification of the Omphalotin Precursor and Variants from *E. coli* BL21

The omphalotin precursor, the different variants and the N-terminal HIS-tagged precursor were expressed in *E. coli* BL21 in TB medium (2.4% (w/v) yeast extract (Oxoid AG, England), 1.2% (w/v) tryptone (Oxoid AG, England), 0.4% (w/v) glycerol, 0.17 M $KH_2PO_4$ and 0.72 M $K_2HPO_4$) containing 50 μg/ml kanamycin. For protein purification of the HIS-tagged precursor cultures were grown at 37° C. to an $OD_{600}$ nm between 1.5-2 after which cultures where cooled down on ice for 30 min and 0.2 mM IPTG was added. Further incubation was performed at 16° C. for the indicated expression times. Bacterial cell pellets were resuspended in ice-cold buffer (50 mM HEPES pH8, 0.1% triton X-100, 10% glycerol) containing 20 mM Imidazole and lysed using a French press. Cell debris was removed by centrifugation at 16000 g for 30 min. For protein purification the supernatant was incubated with Ni-NTA beads (Thermo Scientific, USA) at 4° C. for 1 h and the protein was finally eluted in buffer containing 400 mM Imidazole. Purified protein was concentrated on an Amicon Ultra-4 centrifugal filter device (Millipore, USA) with a molecular weight cut off of 30 kDa, desalted using a PD-10 column (Amersham Biosciences, UK) and flash frozen with liquid nitrogen before storage at −20° C. Protein concentrations were measured using the Pierce BCA protein assay (Thermo Scientific, USA) using a standard curve derived from bovine albumin.

Example 5—Expression and Purification of the Omphalotin Precursor from *S. cerevisiae*

*S. cerevisiae* W303 MATα and W303 MATα/a containing the omphalotin precursor or the N-terminal HIS-tagged precursor were grown at 30° C. in synthetic dropout (SD) media containing raffinose and without histidine to the exponential phase. Cells were harvested and washed once with YP containing galactose and diluted to $OD_{600}$=0.2. Cells were grown till OD=1, washed with ice-cold buffer (50 mM HEPES pH8, 0.1% triton X-100, 10% glycerol) and lysed using glass beads. Cell debris was removed by centrifugation at 16000×g for 30 min, Ni-NTA beads (Thermo Scientific, USA) were added and the protein was purified according to the instructions of the manufacturer. Proteins were desalted and stored as described in example 4.

Example 6—Confirmation of Backbone N-Methylation of Omphalotin Peptide and Variants by LC-MS/MS An Amicon ultra column (30 kDa cutoff) was washed 2 times with $ddH_2O$. 100 μg protein and $ddH_2O$ to a final volume of 400 μL was added. The sample was centrifuged (11000×g for 5 min) and washed with 500 μl of $ddH_2O$. 50 mM $NH_4HCO_3$ pH 8 was added and the sample was concentrated to 4 μg/l. 25 μl was transferred to a glass vial, trypsin (Promega, USA) was added to a molar ratio of 1:70 and the sample incubated for 3 h at 37° C. 3 μl of each sample was used for mass spectrometry analysis. Electrospray ionization-LC-MS data was recorded on a Thermo Scientific Q Exactive mass spectrometer equipped with a Dionex Ultimate 3000 UHPLC system using a Phenomenex Kinetex 2.6 μm C18 100 Å (150×4.6 mm) column heated at 50° C. Elution was performed with a linear gradient using water with 0.1% (v/v) formic acid (solvent A) and acetonitrile with 0.1% (v/v) formic acid (solvent B) at a flow rate of 0.8 mL/min. The column was equilibrated with 5% solvent B for 2 min followed by a linear increase of solvent B to 85% over 15 min and a final elution step with 98% solvent B for 5 min. Mass spectra were acquired in positive ion mode with the following settings; spray voltage 3500V, capillary temperature at 268.75° C., probe heater at 437.5° C. and an S-lens level at 50. Full MS was done at a resolution of 35000 (AGC target 1e6, maximum IT 100 ms, range between 500-1800 m/z) and data-dependent MSMS was performed at a resolution of 17500 (AGC target at 2e5, maximum IT of 300 ms isolation window 1.2) using a stepped NCE of 16, 20 and 24. The inclusion list contained the mass of the trypsin fragment encoding for the omphalotin peptide (or one of the variants) and its different methylation states.

Example 7—In Vitro Methylation of the Omphalotin Precursor and Variants

Omphalotin precursor and variants were purified from *E. coli* induced for only 4 hours to obtain non-methylated protein. To 5 M of protein 1 M S-adenosyl methionine (Sigma-Aldrich, USA) was added and samples were incubated overnight at room temperature. Reactions were performed in 50 μl of 50 mM HEPES pH8, 0.1% triton X-100 and 10% glycerol. Methylation of the omphalotin precursor or variants were asses by LC-MS as described in example 6.

Example 8—In Vitro Methylation of Omphalotin Peptide with and without Follower The syntheses of peptides were performed by automated Fmoc solid-phase peptide synthesis using the following conditions. Fmoc deprotections were performed using 20% piperidine in DMF for 8 min, repeated another cycle to ensure complete removal. For each coupling, Fmoc-amino acid (4.0 equiv), HCTU (3.9 equiv), and NMM (8.0 equiv) in DMF were coupled to free amine on-resin for 45 min. After coupling, resin was treated with 20% acetic anhydride in DMF and NMM (1 equiv to acetic anhydride) for 10 min to cap any unreacted free amine. Synthesis of omphalotin A: Due to the highly hydrophobic sequence of omphalotin A, the synthesis was performed on ChemMatrix Rink amide resin using hexa-arginine tag with a base labile linker at the C-terminal. The first arginine coupling was performed manually on ChemMatrix Rink amide resin (0.1 mmole scale). Afterwards, five subsequent arginine residues and the basic-labile linker (4-hydroxymethyl-benzoic acid, HMBA) were coupled on synthesizer to form the $Arg_6$ tag (SEQ ID NO: 108) to enhance the solubility. The C-terminal residue ($Glu^{18}$ or $Gly^{12}$) was introduced by pre-formed symmetrical anhydride of the corresponding Fmoc-amino acid (5.0 equiv) in the presence of DMAP (0.1 equiv) for 6 hours. The rest of the sequence was introduced by standard automated Fmoc SPPS protocol resulting in the following peptides:

With follower, 1a:

SEQ ID NO: 83

$WVIVVGVVGV^{10}IGSVMSTE^{18}$-HMBA-RRRRRR

Without follower, 1b:

SEQ ID NO: 84

$WVIVVGVVGV^{10}IG^{12}$-HMBA-RRRRRR

Upon the completion of synthesis, the full peptide on-resin with the final Fmoc was cleaved by treatment with a mixture of 94:2:2:2 TFA/TIPS/DODT/$H_2O$ for 1a and 95:2.5:2.5 TFA/TIPS/$H_2O$ for 1b respectively for 2.5 hours. The solid support was filtered off and the filtrate was evaporated under vacuum. The residue was triturated with $Et_2O$ and centrifuged to obtain the crude peptides. The crude peptides were purified by reverse phase HPLC (RP-HPLC) using a gradient of 40% $CH_3CN$ to 90% $CH_3CN$ over 30 min. The fractions containing the product was pooled and lyophilized. The final Fmoc was removed by treatment the peptides with 5% diethylamine in DMSO (2 mM) for 5 min. The solution was neutralized with equal volume of cold TFA (10% in 1:1 $CH_3CN/H_2O$) and the resulting mixture was purified by RP-HPLC and lyophilized to obtain N-terminal free amine of 1a and 1b. For the final removal of the $Arg_6$ tag, 1a and 1b were dissolved in DMSO/$H_2O$ (9:1) to the concentration of 10 mM and treated with one-tenth volume of 1.0 M $NaOH_{(aq)}$ for 90 min. The reaction mixture was cooled in an ice bath, neutralized with TFA, purified by RP-HPLC, and lyophilized to afford the final products:

Omphalotin A (with follower):

SEQ ID NO: 85

$WVIVVGVVGV^{10}IGSVMSTE^{18}$

Omphalotin A (without follower):

SEQ ID NO: 86

$WVIVVGVVGV^{10}IG^{12}$

5 μM of omphalotin precursor, 1 μM S-adenosyl methionine (Sigma-Aldrich, USA) and 1 mM peptide was added to 200 μl of 50 mM HEPES pH8, 0.1% triton X-100 and 10% glycerol. Samples were incubated overnight at room temperature after which they were run over an Amicon ultra column (30 kDa cutoff). The supernatant was collected and methylation of the peptide was assessed by LC-MS as described in example 6.

Example 9 In Vitro Cleavage of Omphalotin Precursor by TEV Protease

TEV protease (Sigma-Aldrich, USA) was added to purified omphalotin precursor containing a TEV cleavage site at a molar ratio of 1:100 and incubated overnight at 4° C. Cleavage of the precursor was assessed by LC-MS/MS as described in example 6.

Example 10 In Vitro Proteolysis and Cyclisation of the Omphalotin Precursor by the Prolyl Oligopeptidase Proteolysis of the peptide from the omphalotin precursor and cyclisation reactions were performed as described by Luo et al., (2014) Chemistry and Biology 21, 1610-1617. In short, 2 μg of omphalotin precursor together with 10 μg of POP was dissolved in 50 mM Tris-HCl (pH7.5) in a reaction volume of 50 and incubated at 37° C. for 4 hr. For POP activity on peptides, 1 mM of omphalotin peptide with or without follower (see above) were dissolved in 50 mM Tris-HCl (pH7.5) containing 1 mM dithiothreitol, or 0.1% trifluoroacetic acid and incubated together with 2 μg of POP. After the incubation reactions were quenched with 50 μl of methanol and the samples were centrifuged for 5 min. The supernatant was analyzed by HPLC (see Luo et al., (2014) Chemistry and Biology 21:1610-1617) or LC-MS as described in example 6.

Example 11 In Vivo Proteolysis and Cyclisation of the Omphalotin Precursor by the Prolyl Oligopeptidase STREP-tagged POP and HIS-tagged OMP where co-expressed in *E. coli* BL21 using the pCDFDUET-1 vector (Merck Millipore, Germany) and brought to expression as described in Example 4. For analysis of proteolysis of the omphalotin precursor protein was purified as described in Example 4 and send for analysis by whole protein LC/TOF-MS by the Functional Genomics Center (University Zurich). To assess cyclisation and cleavage the supernatant of the whole cell extract after high spin centrifugation was run over an Amicon Ultra-4 centrifugal filter device (Millipore, USA) with a molecular weight cut off of 10 kDa. The supernatant was analyzed by HPLC (see Luo et al., (2014) Chemistry and Biology 21:1610-1617) or LC-MS as described in example 6.

The invention claimed is:

1. A method for producing an N-methylated (poly)peptide comprising the steps of:

(A) providing a modified polypeptide having methyl transferase activity, wherein the polypeptide is selected from:

(a) a polypeptide having an amino acid sequence of SEQ ID NO: 15, (b) a polypeptide encoded by a nucleic acid selected from:

(i) a nucleic acid sequence of SEQ ID NO: 1;

(ii) a nucleic acid sequence of at least 80% identity with a nucleic acid sequence of SEQ ID NO: 1; and (iii) a nucleic acid sequence that hybridizes to the nucleic acid sequence of (i) or (ii) under stringent conditions comprising 6× sodium chloride/sodium citrate buffer at 45° C. and washing with 0.2× sodium chloride/sodium citrate buffer, 0.1% SDS at 65° C.;

wherein the nucleic acid sequence encodes a polypeptide having N-methyl transferase activity, (c) a polypeptide having an amino acid sequence identity of at least 80% with the polypeptides of (a) or (b), wherein the polypeptide has N-methyl transferase activity, and the modification is a histidine tag, (B) providing a (poly)peptide for N-methylation, (C) contacting the polypeptide having methyl transferase activity of (A) and the (poly)peptide for N-methylation of (B) under conditions that allow for N-methylation, (D) optionally cyclisation of the methylated peptide, (E) optionally further modifying the N-methylated (poly) peptide, (F) optionally cleaving the methylated peptide from the precursor, and (G) optionally at least partially purifying the N-methylated (poly)peptide.

2. The method according to claim 1, wherein the polypeptide having methyl transferase activity of step (A) and/or the (poly)peptide for N-methylation of step (B) are provided by at least one of:

a recombinant vector comprising a nucleic acid sequence selected from the group consisting of:

(i) a nucleic acid sequence of SEQ ID NO: 1;

(ii) a nucleic acid sequence of at least 80% identity with a nucleic acid sequence of SEQ ID NO: 1; and (iii) a nucleic acid sequence that hybridizes to the nucleic acid sequence of (i) or (ii) under stringent conditions comprising 6× sodium chloride/sodium citrate buffer at 45° C. and washing with 0.2× sodium chloride/sodium citrate buffer, 0.1% SDS at 65° C.;

(iv) a fragment of any of the nucleic acid sequences of (i) to (iii), that hybridizes to the nucleic acid sequence of (i) or (ii) under stringent conditions comprising 6× sodium chloride/sodium citrate buffer at 45° C. and washing with 0.2× sodium chloride/sodium citrate buffer, 0.1% SDS at 65° C.; and (v) a nucleic acid sequence, wherein said nucleic acid sequence is derivable by at least one of substitution, addition, deletion, or a combination thereof of one of the nucleic acids of (i) to (iv) that hybridizes to the nucleic acid sequence of (i) or (ii) under stringent conditions comprising 6× sodium chloride/sodium citrate buffer at 45° C. and washing with 0.2× sodium chloride/sodium citrate buffer, 0.1% SDS at 65° C., wherein the nucleic acid sequence encodes a polypeptide having N-methyl transferase activity;

a host cell including the nucleic acid or the recombinant vector; or a combination thereof.

3. The method according to claim 1, wherein the polypeptide having methyl transferase activity of step (A) and the (poly)peptide for N-methylation of step (B) are provided as a single fusion protein comprising:

a first polypeptide sequence selected from the group consisting of:

(a) polypeptides having an amino acid sequence of SEQ ID NO: 15, (b) polypeptides encoded by a nucleic acid sequence selected from the group consisting of:

(i) a nucleic acid sequence of SEQ ID NO: 1;

(ii) a nucleic acid sequence of at least 80% identity with a nucleic acid sequence of SEQ ID NO: 1; and (iii) a nucleic acid sequence that hybridizes to the nucleic acid sequence of (i) or (ii) under stringent conditions comprising 6× sodium chloride/sodium citrate buffer at 45° C. and washing with 0.2× sodium chloride/sodium citrate buffer, 0.1% SDS at 65° C.;

(iv) a fragment of any of the nucleic acid sequences of (i) to (iii), that hybridizes to the nucleic acid sequence of (i) or (ii) under stringent conditions comprising 6× sodium chloride/sodium citrate buffer at 45° C. and washing with 0.2× sodium chloride/sodium citrate buffer, 0.1% SDS at 65° C.; and (v) a nucleic acid sequence, wherein said nucleic acid sequence is derivable by at least one of substitution, addition, deletion, or a combination thereof of one of the nucleic acids of (i) to (iv) that hybridizes to the nucleic acid sequence of (i) or (ii) under stringent conditions comprising 6× sodium chloride/sodium citrate buffer at 45° C. and washing with 0.2× sodium chloride/sodium citrate buffer, 0.1% SDS at 65° C., wherein the nucleic acid sequence encodes a polypeptide having N-methyl transferase activity (c) polypeptides having an amino acid sequence identity of at least 80% with the polypeptides of (a) or (b), wherein the polypeptide has N-methyl transferase activity; and at least a second polypeptide sequence for N-methylation by the N-methyl transferase activity of the first polypeptide sequence.

4. The method according to claim 1, wherein at least one further enzyme, protein, or combination thereof is added in step (D), step (E), or a combination thereof, to further modify the N-methylated (poly)peptide.

5. The method according to claim 4, wherein the further enzyme or protein is selected from the group consisting of prolyl oligopeptidase (POP), monooxygenase, O-acyl transferase, and oxidoreductase.

6. The method according to claim 1, wherein the nucleic acid sequence has at least 90% identity with the nucleic acid sequence of SEQ ID NO: 1.

7. The method according to claim 2, wherein the host cell selected from the group consisting of a yeast cell, *E. coli, B. subtilis*, plant cell, NIH-3T3 mammalian cell, and insect cell.

8. The method according to claim 2, wherein the recombinant vector is a viral vector or plasmid derived vector.

9. The method according to claim 2, wherein the recombinant vector is selected from a baculovirus vector, lentivirus vector, adenovirus vector, yeast vector or bacterial vector.

10. The method of claim 1, wherein the N-methylated (poly)peptide is a backbone N-methylated (poly)peptide.

11. The method of claim 5, wherein the further enzyme or protein is P450 monooxygenase.

12. The method according to claim 1, wherein said nucleic acid is a DNA, RNA or PNA.

13. The method according to claim 1, wherein said nucleic acid encodes a polypeptide having N-methyl transferase activity for methylating peptidic backbone amides.

14. The method according to claim 1, wherein the nucleic acid further comprises a nucleic acid sequence encoding a (poly)peptide for N-methylation by the N-methyl transferase encoded by the nucleic acid.

15. The method according to claim 1, wherein said polypeptide has N-methyl transferase activity for methylating peptidic backbone amides.

* * * * *

SEQUENCE LISTING

<160> NUMBER OF SEQ ID NOS: 115

<210> SEQ ID NO 1
<211> LENGTH: 1254
<212> TYPE: DNA
<213> ORGANISM: Omphalotus olearius

<400> SEQUENCE: 1
atggagactt ccactcagac caaagctggc tcactcacca tcgtcggtac cggtatcgag 60
agtatcggac aaatgacgct tcaggcgttg tcctacatcg aagccgccgc gaaggttttc 120
tactgcgtca tcgaccccgc cactgaggca ttcatcctca ccaagaacaa gaactgcgtt 180
gacttgtatc agtattacga caatggcaag tccagattga acacttacac ccaaatgtca 240
gagctcatgg tcagggaagt ccgcaagggc ctcgatgtcg tgggcgtctt ctacggccac 300
ccaggagtgt tcgtgaaccc gtctcaccga gctctggcta tcgccaagag tgaaggctac 360
cgagcgagga tgcttccagg cgtgtctgcg gaagattgtc tcttcgcgga cttgtgcatt 420
gatccttcga acccgggttg cctgacctac gaggcatcgg atttcctgat cagggatcgc 480
ccggtcagca tccacagtca cttggtcctg ttccaagtcg gatgcgtcgg tatcgccgac 540
ttcaacttca ctggattcga caacaacaaa ttcggcgttc tcgtcgaccg tctcgagcaa 600
gaatacggcg ccgagcaccc tgtcgtccat tacatcgcag ctatgatgcc acaccaagac 660
ccagtcaccg ataaatacac cgtcgcgcag ctccgtgagc ccgagatcgc gaagcgtgtt 720
ggcggtgtct cgactttcta catccctccc aaggccagga aagcatcgaa cttggacatc 780
ataaggcgcc tagagctctt gcctgctggg caagttcccg acaagaaagc gcgtatttac 840
ccggccaacc agtgggagcc cgatgttccc gaagtcgaac cctacagacc atctgaccag 900
gctgccatcg ctcagttggc tgaccacgct cctcctgagc aatatcaacc tcttgctact 960
tcgaaagcca tgtctgatgt tatgacgaag ttggctttgg atcccaaggc actcgccgac 1020
tacaaagctg atcaccgcgc ctttgctcaa tctgtccccg acttgacgcc tcaggagcgt 1080
gcggctttgg agctcggtga ttcgtgggct attcgttgcg cgatgaagaa tatgccctcg 1140
tcgctcttgg acgctgctcg tgaatccggc gaagaggcat cccaaaacgg tttcccatgg 1200
gtcatcgtcg ttggtgttat cggtgtcatc ggatcagtca tgagcacgga ataa 1254

<210> SEQ ID NO 2
<211> LENGTH: 624
<212> TYPE: DNA
<213> ORGANISM: Omphalotus olearius

<400> SEQUENCE: 2
ctcaccatcg tcggtaccgg tatcgagagt atcggacaaa tgacgcttca ggcgttgtcc 60
tacatcgaag ccgccgcgaa ggttttctac tgcgtcatcg accccgccac tgaggcattc 120
atcctcacca agaacaagaa ctgcgttgac ttgtatcagt attacgacaa tggcaagtcc 180
agattgaaca cttacaccca aatgtcagag ctcatggtca gggaagtccg caagggcctc 240
gatgtcgtgg gcgtcttcta cggccaccca ggagtgttcg tgaacccgtc tcaccgagct 300
ctggctatcg ccaagagtga aggctaccga gcgaggatgc ttccaggcgt gtctgcggaa 360
gattgtctct tcgcggactt gtgcattgat ccttcgaacc cgggttgcct gacctacgag 420
gcatcggatt tcctgatcag ggatcgcccg gtcagcatcc acagtcactt ggtcctgttc 480
caagtcggat gcgtcggtat cgccgacttc aacttcactg gattcgacaa caacaaattc 540
ggcgttctcg tcgaccgtct cgagcaagaa tacggcgccg agcaccctgt cgtccattac 600
atcgcagcta tgatgccaca ccaa 624

<210> SEQ ID NO 3
<211> LENGTH: 1254
<212> TYPE: DNA
<213> ORGANISM: Dendrothele bispora

<400> SEQUENCE: 3
atggaatctt ctactcaaac caaacccggt tcgctcatcg tcgtcggtac aggcatcgag 60
agcatcggtc aaatgacgct ccaagcctta tcgtacattg aagctgcttc caaagtcttc 120
tattgtgtca tcgaccctgc gacagaggct tttatcctca ccaagaacaa gaattgtgtc 180
gacttgtatc agtactacga caatggcaag tctagaatgg atacttacac ccaaatggct 240
gagctcatgc tcaaggaagt ccgcaatggc ctcgacgttg tcggggtatt ctatggccat 300
ccgggcgtgt tcgtgaaccc ttctcacagg gcattggcta tcgccagaag cgagggatac 360
caagctcgta tgcttccagg agtatctgca gaggactgcc tctttgccga cttatgcatc 420
gacccctcga accccggctg cttgacctac gaagcatccg atttcctcat cagagagaga 480
ccagtgaacg ttcacagtca cctcattctt ttccaagttg gatgcgtcgg tatcgcagac 540
ttcaatttca gcggattcga caattcgaaa tttaccattc tggttgaccg tctcgagcaa 600
gaatacggcc cagaccatac cgtcgtgcat tatatcgcag ctatgatgcc tcaccaagat 660
cccgtcaccg acaagttcac gatcggacaa ctccgtgaac ccgaaatcgc caaacgagta 720
ggtggtgttt cgacttttta catccctcca aaggccagaa aggatatcaa caccgatatc 780
atccgactct tggaattcct acctgctggt aaagttcccg acaaacacac ccaaatctac 840
ccacctaatc aatgggaacc cgacgtgcct actctacctc cctatggaca aaacgaacag 900
gctgctatca ctagattgga agctcacgct ccccccgaag agtatcagcc tctggccact 960
tccaaagcta tgactgacgt catgaccaaa ctagctttgg atcccaaggc gctcgccgag 1020
tataaggctg atcatcgagc cttcgctcag tctgttcctg acttgacgcc tcaagagaga 1080
gcagctttgg agctaggaga ttcatgggct attcggtgcg ccatgaagaa catgccgtcc 1140
tctctcttgg aagccgctag ccagtccgtc gaagaggcat ccatgaacgg tttcccatgg 1200
gtcatcgtca cgggtatcgt tggggtcatc ggatcggttg tgagcagtgc ttga 1254

<210> SEQ ID NO 4
<211> LENGTH: 666
<212> TYPE: DNA
<213> ORGANISM: Dendrothele bispora

<400> SEQUENCE: 4
ctcatcgtcg tcggtacagg catcgagagc atcggtcaaa tgacgctcca agccttatcg 60
tacattgaag ctgcttccaa agtcttctat tgtgtcatcg accctgcgac agaggctttt 120
atcctcacca agaacaagaa ttgtgtcgac ttgtatcagt actacgacaa tggcaagtct 180
agaatggata cttacaccca aatggctgag ctcatgctca aggaagtccg caatggcctc 240
gacgttgtcg gggtattcta tggccatccg ggcgtgttcg tgaacccttc tcacagggca 300
ttggctatcg ccagaagcga gggataccaa gctcgtatgc ttccaggagt atctgcagag 360
gactgcctct ttgccgactt atgcatcgac ccctcgaacc ccggctgctt gacctacgaa 420
gcatccgatt tcctcatcag agagagacca gtgaacgttc acagtcacct cattcttttc 480
caagttggat gcgtcggtat cgcagacttc aatttcagcg gattcgacaa ttcgaaattt 540

-continued

```
accattctgg ttgaccgtct cgagcaagaa tacggcccag accataccgt cgtgcattat    600

atcgcagcta tgatgcctca ccaagatccc gtcaccgaca agttcacgat cggacaactc    660

cgtgaa                                                               666


<210> SEQ ID NO 5
<211> LENGTH: 1236
<212> TYPE: DNA
<213> ORGANISM: Fomitiporia mediterranea

<400> SEQUENCE: 5

atggctacct ctactgagac tacagagaaa aagggctcgc tgactattgc tggcaccggt     60

attgccagta tcaaacacat cacactcgag acactgtcct atatcaaaga ggctgaaaag    120

gtctattacc ttgtcgctga cccagcgacg gaagcgttca ttcaggataa tgccagcgga    180

acgtgcttca atttacacgt tttctacgat acaaacaagc atcgctatga ttcatacgtt    240

cagatggccg aggtcatgtt gctcgacgtg agagccgggc actccgtcct tggaattttc    300

tatggccacc cgggcgtttt tgtgtcgcct tcccataggg ccattgctat agcacgagag    360

gaaggcttca aggctcacat gctccccgga atatcggcag aggattacat gtttgccgac    420

attggatttg atcccgccac acatggatgt gtgtcatacg aagcgaccga gcttttggtc    480

cgagacaagc cgttgcttcc atcgtcccac aatatcatct ggcaggttgg agctattggt    540

gctaacgcaa tggtgttcga taatggcaaa tttaatatcc ttgttgaccg cctcgaacaa    600

gtctttggtc cagaccataa ggttgtgcac tatattggtg ctgtcctccc gcaatcgacg    660

tcgacgatcg aagcatacac catctctgat ctccgtaagg gcgacgttgt ggagaaattt    720

tcaacgactt caacacttta cgtgcctcca tccgttgaag ccagactcag cggaataatg    780

gttcgggagc taggacttga ggattcagga ttccacacaa agagcagtca gtcacgaacg    840

ttgtgggccg gaccagttac tagctcagca ccggcatatg gccctcagga gcgcattgtt    900

attgcacaga tagacaagga cgttattcct gacagccacc agatccttca ggcttccgat    960

gcaatgaaga aaacgatggc taaccttgca ctaaacccga aattgtcgga ggagtactat   1020

gcaagcccat caactgtcgt tgaaaaagtg actgggcttt ctgaacaaga gaagaaggca   1080

cttatacttt gttctgctgg cgcaattcat atggtaatgg cggcaacgca aaccaacatc   1140

gctcaaggac atcagtggtc tgctgaggag cttgaggctg caggaactcc tcatcctgca   1200

ctagctcttc tagttgttat aatatgcctt atatag                             1236


<210> SEQ ID NO 6
<211> LENGTH: 588
<212> TYPE: DNA
<213> ORGANISM: Fomitiporia mediterranea

<400> SEQUENCE: 6

ctgactattg ctggcaccgg tattgccagt atcaaacaca tcacactcga gacactgtcc     60

tatatcaaag aggctgaaaa ggtctattac cttgtcgctg acccagcgac ggaagcgttc    120

attcaggata atgccagcgg aacgtgcttc aatttacacg ttttctacga tacaaacaag    180

catcgctatg attcatacgt tcagatggcc gaggtcatgt tgctcgacgt gagagccggg    240

cactccgtcc ttggaatttt ctatggccac ccgggcgttt ttgtgtcgcc ttcccatagg    300

gccattgcta tagcacgaga ggaaggcttc aaggctcaca tgctccccgg aatatcggca    360

gaggattaca tgtttgccga cattggattt gatcccgcca cacatggatg tgtgtcatac    420

gaagcgaccg agcttttggt ccgagacaag ccgttgcttc catcgtccca caatatcatc    480
```

```
tggcaggttg gagctattgg tgctaacgca atggtgttcg ataatggcaa atttaatatc    540

cttgttgacc gcctcgaaca agtctttggt ccagaccata aggttgtg                 588


<210> SEQ ID NO 7
<211> LENGTH: 1608
<212> TYPE: DNA
<213> ORGANISM: Fomitiporia mediterranea

<400> SEQUENCE: 7

atggctacct ccactgagac tgcacagaaa aagggctcgc tgactattgc tggcaccggt     60

atcgccagta tcaaacacat caccctcgag acactgtcct atatcaaaga ggctgaaaag    120

gtctattatc ttgtcgccga tccagcgacg gaagcgttca tccatgataa tgctagcgga    180

acgtgcttca atttacacgt tttctacgat acaaacaagc ttcgctatga ttcatatgtc    240

cagatggccg aggtcatgct acgcgacgtg agagcaggga attctgtcct tggactattt    300

tatggacatc cgggagtgtt tgtgtcgcct tcccacaggg ccattgccgt agcacgggag    360

gaaggcttca aggctcaaac gctccccgga atatcggcag aagattacat gttcgccgac    420

attggatttg atcccgccag tcatggatgt gtgtcatacg aagcgaccga ccttttggcc    480

agagacaaac cattgcttcc atcgtcccat aatatcatct ggcaggttgg agctattggt    540

gctaatgcaa tggtgtttga taatggcaaa tttaatgtcc ttgtcgaccg cctcgagaga    600

gactttggtc ctaaccataa agttgtgcac tatattggtg ctgttctccc tcaatcgacg    660

tcgaaggtcg aacagtacac cgttgcagat ctacgtaagg attacgttgt taagacattt    720

accacaacct caacactcta cgtgcctcct tgcgttgacg ctgggatcag caatataatg    780

gcaagggagc taggactcga ggattcaaca ggattacgta cgaggggcaa ccaaccatta    840

ccattgaaga ctggaccagc cattagtcta gcgtcggtat atggctctca cgagcgtact    900

accattgctc agatagacaa gggtgttacc cctgacacgc tacagatcct tcaggcgtcc    960

gatgcgatga agaaactgat ggccgacctt gcgctgaagc caaaactatt ggagaaatac   1020

cgtggaaacc catcagtagt cattgacgag gtgactggac ttgccccaca agagaaggct   1080

gcccttacac tttgttctgc tggagcaatt tatatggtaa tggcagcaag ccaaattgat   1140

attgctaaag ggcttgtatt agtcaaacgg attgaagaag tcttgctcaa gaacaatata   1200

tcatccggtc gcgggcaact aattactgcg ggtgcaatct accattcttc tctcgccagg   1260

ctcgtctggg gcgcccaagt tgccccagca gagattgaac aagtcctact ctcgcatcct   1320

gaaggactcg tcatcgacgc accgttgcag gagttccggg tcctacagaa cgtgacgaac   1380

gcgttcttcg aatgtgagag tggaggtgtg aagagtttgg atggtcgggt tcgtgaaagt   1440

ttgagtcggt gtaagtggtt gacgggaggg atcgctgtcg tgcatgagat actgaagaac   1500

ccgattggga tggtgttgag acggatgctt gttgatgagt atgtgaagaa gaaggcggtt   1560

agagaactac ccgagaagac tttggtactc cgtctcccag aagactga                1608


<210> SEQ ID NO 8
<211> LENGTH: 588
<212> TYPE: DNA
<213> ORGANISM: Fomitiporia mediterranea

<400> SEQUENCE: 8

ctgactattg ctggcaccgg tatcgccagt atcaaacaca tcaccctcga gacactgtcc     60

tatatcaaag aggctgaaaa ggtctattat cttgtcgccg atccagcgac ggaagcgttc    120
```

```
atccatgata atgctagcgg aacgtgcttc aatttacacg ttttctacga tacaaacaag    180

cttcgctatg attcatatgt ccagatggcc gaggtcatgc tacgcgacgt gagagcaggg    240

aattctgtcc ttggactatt ttatggacat ccgggagtgt ttgtgtcgcc ttcccacagg    300

gccattgccg tagcacggga ggaaggcttc aaggctcaaa cgctccccgg aatatcggca    360

gaagattaca tgttcgccga cattggattt gatcccgcca gtcatggatg tgtgtcatac    420

gaagcgaccg accttttggc cagagacaaa ccattgcttc catcgtccca taatatcatc    480

tggcaggttg gagctattgg tgctaatgca atggtgtttg ataatggcaa atttaatgtc    540

cttgtcgacc gcctcgagag agactttggt cctaaccata aagttgtg                 588
```

<210> SEQ ID NO 9
<211> LENGTH: 1299
<212> TYPE: DNA
<213> ORGANISM: Fomitiporia mediterranea

<400> SEQUENCE: 9

```
atggctgcta ctactgagac tatgaagaaa ggctctctga ccattgctgg atcaggcatt     60

gccagtatca agcatatgac tcttgagacg gtgtcccaca tcaaagaggc cgagaaggtc    120

tactacatcg tcaccgaccc tgcgacggag gcgtacatca aggataatgc tgtcggagca    180

tgcttcgact tgcgcgtctt ctacgatacg aacaagcctc gttatgaatc atatgtccag    240

atgtccgagg tcatgctgcg agacgtgaga gtgggccatt cggtccttgg gatcttctac    300

ggccacccag gtgtctttgt atcgccctct cacagagcta tcgctatagc gaaagaggag    360

ggtttccagg ctcgaatgct cccaggtatc tcggccgagg actacctgtt cgccgacatt    420

ggattcgacc ctgccgctca tggttgcatg tcatacgaag ccactgaact tttagtccga    480

aacaagccat tgaacacttc cacgcataac atcatctggc aagttggagc ccttggtgct    540

gaagcaatgg tatttgataa tgccaagttc agtttgcttg tcgaccgtct tgagcaagac    600

tatggttccg accataaggt cgtgcattac attggcgcta tcctccccca ggcggatcca    660

actgtcgagg cgtatatcgt tgccgacctt cgcaaggagg acgtcgtgaa gcagttcaac    720

gcgatatcta cgctgtacat ccctccgcgt gtcgctggca agttcttgga tgacatggct    780

aagaaactcg gaatcgccga ttctgcagcc tatctgaaga atcactatcc acaagcaccg    840

tacactggac ccgagtttgc cactgatccc gcttacggac ctcgcgagaa ggctgtcatc    900

gaccagattg acaaccatgc tgcgccagag ggacacacgg tcctccatgc ttcggatgca    960

ctgaagaaac tgaatactga ccttgcgcta tctccaaaat tcctggagga gtacaaggaa   1020

aacccgatgc cgatccttga agcgatggat ggtctcacca acgaagagaa agccgcactt   1080

atgcaaaacc cgcttggcgc gactcatgag ttaatgtggg caaccccaga tgagatagcc   1140

aacggacgcg cgcttcctgt cgttaacttt atggcgtacg gtggctatgg gggatactat   1200

ggaggaggat gcaggccctg cccctgctgc gtcgtcacgg atcgatggtc ttcaggaggg   1260

tcaaacaaat gcaatatggt gaacaattta aatgtctga                          1299
```

<210> SEQ ID NO 10
<211> LENGTH: 588
<212> TYPE: DNA
<213> ORGANISM: Fomitiporia mediterranea

<400> SEQUENCE: 10

```
ctgaccattg ctggatcagg cattgccagt atcaagcata tgactcttga gacggtgtcc     60

cacatcaaag aggccgagaa ggtctactac atcgtcaccg accctgcgac ggaggcgtac    120
```

```
atcaaggata atgctgtcgg agcatgcttc gacttgcgcg tcttctacga tacgaacaag    180

cctcgttatg aatcatatgt ccagatgtcc gaggtcatgc tgcgagacgt gagagtgggc    240

cattcggtcc ttgggatctt ctacggccac ccaggtgtct ttgtatcgcc ctctcacaga    300

gctatcgcta tagcgaaaga ggagggtttc caggctcgaa tgctcccagg tatctcggcc    360

gaggactacc tgttcgccga cattggattc gaccctgccg ctcatggttg catgtcatac    420

gaagccactg aacttttagt ccgaaacaag ccattgaaca cttccacgca taacatcatc    480

tggcaagttg gagcccttgg tgctgaagca atggtatttg ataatgccaa gttcagtttg    540

cttgtcgacc gtcttgagca agactatggt tccgaccata aggtcgtg                 588
```

<210> SEQ ID NO 11
<211> LENGTH: 1266
<212> TYPE: DNA
<213> ORGANISM: Fomitiporia mediterranea

<400> SEQUENCE: 11

```
atggctgcta ctactgagac taccaagaaa ggatctctga ccattgctgg atctggcatt     60

gccagtatca agcatatgac tcttgagacg gtgtcccaca tcaaagaggt cgagaaggtc    120

tactacatcg tctccgaccc tgcgacggag gcatacatca aggataatgc tgtcggaaca    180

tgcttcgact tgcgcgtctt ctacgataca aataaacctc gttatgaatc agatgtccag    240

atgtccgagg tcatgctgcg agacgtcaga gctggccatt cggtccttgg gatcttctac    300

ggccacccag gtgtctttgt atcgccctct catagggcca tcgctatagc gaaggaggag    360

ggattccagg ctcgaatgct cccaggtatc tcggccgagg actacctgtt tgccgatatt    420

ggattcgatc ctgccgttca tggttgcatg tcatacgagg ctactgaact tttggtccgg    480

aacaaaccat tgaacacttc cacgtataac attatctggc aagtcggagc ccttggtgcg    540

gaagcgatgg tgtttgataa tgccaagttc agtctgcttg tcgaccgtct tgagcgagac    600

tatggatccg accataaggt cgtgcattac attggtgcca tactccctca ggccgattcg    660

accatcgaag cgcacacagt ttctgacctc cgtaaggagg acatcgtaaa gcagttcaac    720

gcgatatcta cgctctatat ccctccgcgt gtcgctggca agttcttgga tgacatggtc    780

gagaaactcg gaatcgccga tcctgcaacc tttctgaaga atcactacac tcaaccgcca    840

tacagtggac cggagtttgc cactgatccc gcttacggac ctcgcgagaa ggctgtcatc    900

gaccagatcg acaaccatgc tgcgccagag ggacatacag tccttcacgc aacagatgcg    960

ttgaagaaac tgaacactga ccttgcgcta tctccgaaat tcctgaagga gtacaaggaa   1020

aacccgatgc cgatccttga agcgatggat ggtctcaccg atgaagagca agccgcgctt   1080

atgcaaaacc cgcttggcgc gactcatgag ctaatgtggg caaccccaga tgagatagcc   1140

aacggacgtg tgcttcctgt cgttaacttt tgttttctcg gcggcaatag gagaggctat   1200

aggagaggct atcaagcagt gaactacgga gggagttata acacatacat catcaacaat   1260

ttctaa                                                              1266
```

<210> SEQ ID NO 12
<211> LENGTH: 588
<212> TYPE: DNA
<213> ORGANISM: Fomitiporia mediterranea

<400> SEQUENCE: 12

```
ctgaccattg ctggatctgg cattgccagt atcaagcata tgactcttga gacggtgtcc     60
```

-continued

```
cacatcaaag aggtcgagaa ggtctactac atcgtctccg accctgcgac ggaggcatac    120

atcaaggata atgctgtcgg aacatgcttc gacttgcgcg tcttctacga tacaaataaa    180

cctcgttatg aatcagatgt ccagatgtcc gaggtcatgc tgcgagacgt cagagctggc    240

cattcggtcc ttgggatctt ctacggccac ccaggtgtct ttgtatcgcc ctctcatagg    300

gccatcgcta tagcgaagga ggagggattc caggctcgaa tgctcccagg tatctcggcc    360

gaggactacc tgtttgccga tattggattc gatcctgccg ttcatggttg catgtcatac    420

gaggctactg aacttttggt ccggaacaaa ccattgaaca cttccacgta taacattatc    480

tggcaagtcg gagcccttgg tgcggaagcg atggtgtttg ataatgccaa gttcagtctg    540

cttgtcgacc gtcttgagcg agactatgga tccgaccata aggtcgtg                 588
```

<210> SEQ ID NO 13
<211> LENGTH: 1254
<212> TYPE: DNA
<213> ORGANISM: Dendrothele bispora

<400> SEQUENCE: 13

```
atgccagtgc gaattccctc cccccagaaa gaagctggct cactcaccat tgttggtact     60

ggaatcgaga gtatcggcca gatcactctc caggccatat ctcatatcga aactgcctcc    120

aaggtctttt actgcgttgt agaccctgcg actgaggcgt tcatccgcac taagaacaag    180

aactgtttcg atctctatcc atactacgac aatggcaagc acagaatgga tacctatatc    240

caaatggctg aggtaatgct caaggaagtc cgcaatgggc tcgatgttgt tggcgtattc    300

tatggtcatc ccggtgtatt tgtaagccct tctcaccggg cccttgccat tgccgaaagc    360

gagggctata aggcaaggat gctcccgggt gtatctgcgg aggactgtct ctttgctgac    420

ttgcgaattg acccctctca ccccggttgc atgacctacg aggcatccga cttccttatt    480

agggagaggc cagtgaacat ccacagtcac ctagttcttt ggcaggtcgg atgtgtcggt    540

gtcgcggact ttaactctgg cggttttaag aatacgaaat tcgatgtact tgttgaccgg    600

ctcgagcagg aatacggtgc cgaccatccg gtcgtgcact atatggcctc cattttgcct    660

tacgaggatc ccgttactga caaattcaca gttagccaat tccgtgatcc tcagattgcc    720

aagcgcattt gcggcatatc gacattctat atccctccaa aggaaacgaa ggactcgaac    780

gtggaagcta tgcatcgtct tcaacttttg ccttctggaa aaggcgtgct aaaggaaaca    840

ggtcgttatc cgtccaacaa atgggcaccc tcaggctcct tccacgatgt tgatccttat    900

ggaccacgag agctcgccgc tgtcaccaag ctgaagagtc acactattcc ggagcattac    960

cagcctcttg ctacttccaa agccatgaca gacgtcatga cgaaactggc tttggatccc   1020

agggtgctca gcgagtacaa ggctagccga caggactttg ttcactccgt gccaggtttg   1080

actccaaacg agaaaaacgc cttggttaaa ggagaaatcg cggcaattcg ctgcggtatg   1140

aagaacattc ccatctcaga gaagcagtgg gagttgagag atggtctggt tactaagttt   1200

attgttgtcc ctatatgggt atcgattgac gatactactg gtaacctcga gtga         1254
```

<210> SEQ ID NO 14
<211> LENGTH: 594
<212> TYPE: DNA
<213> ORGANISM: Dendrothele bispora

<400> SEQUENCE: 14

```
ctcaccattg ttggtactgg aatcgagagt atcggccaga tcactctcca ggccatatct     60

catatcgaaa ctgcctccaa ggtcttttac tgcgttgtag accctgcgac tgaggcgttc    120
```

```
atccgcacta agaacaagaa ctgtttcgat ctctatccat actacgacaa tggcaagcac    180

agaatggata cctatatcca aatggctgag gtaatgctca aggaagtccg caatgggctc    240

gatgttgttg gcgtattcta tggtcatccc ggtgtatttg taagcccttc tcaccgggcc    300

cttgccattg ccgaaagcga gggctataag gcaaggatgc tcccgggtgt atctgcggag    360

gactgtctct ttgctgactt gcgaattgac ccctctcacc ccggttgcat gacctacgag    420

gcatccgact tccttattag ggagaggcca gtgaacatcc acagtcacct agttctttgg    480

caggtcggat gtgtcggtgt cgcggacttt aactctggcg gttttaagaa tacgaaattc    540

gatgtacttg ttgaccggct cgagcaggaa tacggtgccg accatccggt cgtg           594
```

```
<210> SEQ ID NO 15
<211> LENGTH: 417
<212> TYPE: PRT
<213> ORGANISM: Omphalotus olearius

<400> SEQUENCE: 15

Met Glu Thr Ser Thr Gln Thr Lys Ala Gly Ser Leu Thr Ile Val Gly
1               5                   10                  15

Thr Gly Ile Glu Ser Ile Gly Gln Met Thr Leu Gln Ala Leu Ser Tyr
            20                  25                  30

Ile Glu Ala Ala Ala Lys Val Phe Tyr Cys Val Ile Asp Pro Ala Thr
        35                  40                  45

Glu Ala Phe Ile Leu Thr Lys Asn Lys Asn Cys Val Asp Leu Tyr Gln
    50                  55                  60

Tyr Tyr Asp Asn Gly Lys Ser Arg Leu Asn Thr Tyr Thr Gln Met Ser
65                  70                  75                  80

Glu Leu Met Val Arg Glu Val Arg Lys Gly Leu Asp Val Val Gly Val
                85                  90                  95

Phe Tyr Gly His Pro Gly Val Phe Val Asn Pro Ser His Arg Ala Leu
            100                 105                 110

Ala Ile Ala Lys Ser Glu Gly Tyr Arg Ala Arg Met Leu Pro Gly Val
        115                 120                 125

Ser Ala Glu Asp Cys Leu Phe Ala Asp Leu Cys Ile Asp Pro Ser Asn
    130                 135                 140

Pro Gly Cys Leu Thr Tyr Glu Ala Ser Asp Phe Leu Ile Arg Asp Arg
145                 150                 155                 160

Pro Val Ser Ile His Ser His Leu Val Leu Phe Gln Val Gly Cys Val
                165                 170                 175

Gly Ile Ala Asp Phe Asn Phe Thr Gly Phe Asp Asn Asn Lys Phe Gly
            180                 185                 190

Val Leu Val Asp Arg Leu Glu Gln Glu Tyr Gly Ala Glu His Pro Val
        195                 200                 205

Val His Tyr Ile Ala Ala Met Met Pro His Gln Asp Pro Val Thr Asp
    210                 215                 220

Lys Tyr Thr Val Ala Gln Leu Arg Glu Pro Glu Ile Ala Lys Arg Val
225                 230                 235                 240

Gly Gly Val Ser Thr Phe Tyr Ile Pro Pro Lys Ala Arg Lys Ala Ser
                245                 250                 255

Asn Leu Asp Ile Ile Arg Arg Leu Glu Leu Leu Pro Ala Gly Gln Val
            260                 265                 270

Pro Asp Lys Lys Ala Arg Ile Tyr Pro Ala Asn Gln Trp Glu Pro Asp
        275                 280                 285
```

Val Pro Glu Val Glu Pro Tyr Arg Pro Ser Asp Gln Ala Ala Ile Ala
290 295 300

Gln Leu Ala Asp His Ala Pro Pro Glu Gln Tyr Gln Pro Leu Ala Thr
305 310 315 320

Ser Lys Ala Met Ser Asp Val Met Thr Lys Leu Ala Leu Asp Pro Lys
325 330 335

Ala Leu Ala Asp Tyr Lys Ala Asp His Arg Ala Phe Ala Gln Ser Val
340 345 350

Pro Asp Leu Thr Pro Gln Glu Arg Ala Ala Leu Glu Leu Gly Asp Ser
355 360 365

Trp Ala Ile Arg Cys Ala Met Lys Asn Met Pro Ser Ser Leu Leu Asp
370 375 380

Ala Ala Arg Glu Ser Gly Glu Glu Ala Ser Gln Asn Gly Phe Pro Trp
385 390 395 400

Val Ile Val Val Gly Val Ile Gly Val Ile Gly Ser Val Met Ser Thr
405 410 415

Glu

<210> SEQ ID NO 16
<211> LENGTH: 208
<212> TYPE: PRT
<213> ORGANISM: Omphalotus olearius

<400> SEQUENCE: 16

Leu Thr Ile Val Gly Thr Gly Ile Glu Ser Ile Gly Gln Met Thr Leu
1 5 10 15

Gln Ala Leu Ser Tyr Ile Glu Ala Ala Ala Lys Val Phe Tyr Cys Val
20 25 30

Ile Asp Pro Ala Thr Glu Ala Phe Ile Leu Thr Lys Asn Lys Asn Cys
35 40 45

Val Asp Leu Tyr Gln Tyr Tyr Asp Asn Gly Lys Ser Arg Leu Asn Thr
50 55 60

Tyr Thr Gln Met Ser Glu Leu Met Val Arg Glu Val Arg Lys Gly Leu
65 70 75 80

Asp Val Val Gly Val Phe Tyr Gly His Pro Gly Val Phe Val Asn Pro
85 90 95

Ser His Arg Ala Leu Ala Ile Ala Lys Ser Glu Gly Tyr Arg Ala Arg
100 105 110

Met Leu Pro Gly Val Ser Ala Glu Asp Cys Leu Phe Ala Asp Leu Cys
115 120 125

Ile Asp Pro Ser Asn Pro Gly Cys Leu Thr Tyr Glu Ala Ser Asp Phe
130 135 140

Leu Ile Arg Asp Arg Pro Val Ser Ile His Ser His Leu Val Leu Phe
145 150 155 160

Gln Val Gly Cys Val Gly Ile Ala Asp Phe Asn Phe Thr Gly Phe Asp
165 170 175

Asn Asn Lys Phe Gly Val Leu Val Asp Arg Leu Glu Gln Glu Tyr Gly
180 185 190

Ala Glu His Pro Val Val His Tyr Ile Ala Ala Met Met Pro His Gln
195 200 205

<210> SEQ ID NO 17
<211> LENGTH: 417
<212> TYPE: PRT
<213> ORGANISM: Dendrothele bispora

<400> SEQUENCE: 17

```
Met Glu Ser Ser Thr Gln Thr Lys Pro Gly Ser Leu Ile Val Val Gly
1               5                   10                  15

Thr Gly Ile Glu Ser Ile Gly Gln Met Thr Leu Gln Ala Leu Ser Tyr
            20                  25                  30

Ile Glu Ala Ala Ser Lys Val Phe Tyr Cys Val Ile Asp Pro Ala Thr
        35                  40                  45

Glu Ala Phe Ile Leu Thr Lys Asn Lys Asn Cys Val Asp Leu Tyr Gln
    50                  55                  60

Tyr Tyr Asp Asn Gly Lys Ser Arg Met Asp Thr Tyr Thr Gln Met Ala
65                  70                  75                  80

Glu Leu Met Leu Lys Glu Val Arg Asn Gly Leu Asp Val Val Gly Val
                85                  90                  95

Phe Tyr Gly His Pro Gly Val Phe Val Asn Pro Ser His Arg Ala Leu
            100                 105                 110

Ala Ile Ala Arg Ser Glu Gly Tyr Gln Ala Arg Met Leu Pro Gly Val
        115                 120                 125

Ser Ala Glu Asp Cys Leu Phe Ala Asp Leu Cys Ile Asp Pro Ser Asn
    130                 135                 140

Pro Gly Cys Leu Thr Tyr Glu Ala Ser Asp Phe Leu Ile Arg Glu Arg
145                 150                 155                 160

Pro Val Asn Val His Ser His Leu Ile Leu Phe Gln Val Gly Cys Val
                165                 170                 175

Gly Ile Ala Asp Phe Asn Phe Ser Gly Phe Asp Asn Ser Lys Phe Thr
            180                 185                 190

Ile Leu Val Asp Arg Leu Glu Gln Glu Tyr Gly Pro Asp His Thr Val
        195                 200                 205

Val His Tyr Ile Ala Ala Met Met Pro His Gln Asp Pro Val Thr Asp
    210                 215                 220

Lys Phe Thr Ile Gly Gln Leu Arg Glu Pro Glu Ile Ala Lys Arg Val
225                 230                 235                 240

Gly Gly Val Ser Thr Phe Tyr Ile Pro Pro Lys Ala Arg Lys Asp Ile
                245                 250                 255

Asn Thr Asp Ile Ile Arg Leu Leu Glu Phe Leu Pro Ala Gly Lys Val
            260                 265                 270

Pro Asp Lys His Thr Gln Ile Tyr Pro Pro Asn Gln Trp Glu Pro Asp
        275                 280                 285

Val Pro Thr Leu Pro Pro Tyr Gly Gln Asn Glu Gln Ala Ala Ile Thr
    290                 295                 300

Arg Leu Glu Ala His Ala Pro Pro Glu Glu Tyr Gln Pro Leu Ala Thr
305                 310                 315                 320

Ser Lys Ala Met Thr Asp Val Met Thr Lys Leu Ala Leu Asp Pro Lys
                325                 330                 335

Ala Leu Ala Glu Tyr Lys Ala Asp His Arg Ala Phe Ala Gln Ser Val
            340                 345                 350

Pro Asp Leu Thr Pro Gln Glu Arg Ala Ala Leu Glu Leu Gly Asp Ser
        355                 360                 365

Trp Ala Ile Arg Cys Ala Met Lys Asn Met Pro Ser Ser Leu Leu Glu
    370                 375                 380

Ala Ala Ser Gln Ser Val Glu Glu Ala Ser Met Asn Gly Phe Pro Trp
385                 390                 395                 400

Val Ile Val Thr Gly Ile Val Gly Val Ile Gly Ser Val Val Ser Ser
                405                 410                 415
```

Ala

<210> SEQ ID NO 18
<211> LENGTH: 222
<212> TYPE: PRT
<213> ORGANISM: Dendrothele bispora

<400> SEQUENCE: 18

Leu Ile Val Val Gly Thr Gly Ile Glu Ser Ile Gly Gln Met Thr Leu
1 5 10 15

Gln Ala Leu Ser Tyr Ile Glu Ala Ala Ser Lys Val Phe Tyr Cys Val
20 25 30

Ile Asp Pro Ala Thr Glu Ala Phe Ile Leu Thr Lys Asn Lys Asn Cys
35 40 45

Val Asp Leu Tyr Gln Tyr Tyr Asp Asn Gly Lys Ser Arg Met Asp Thr
50 55 60

Tyr Thr Gln Met Ala Glu Leu Met Leu Lys Glu Val Arg Asn Gly Leu
65 70 75 80

Asp Val Val Gly Val Phe Tyr Gly His Pro Gly Val Phe Val Asn Pro
85 90 95

Ser His Arg Ala Leu Ala Ile Ala Arg Ser Glu Gly Tyr Gln Ala Arg
100 105 110

Met Leu Pro Gly Val Ser Ala Glu Asp Cys Leu Phe Ala Asp Leu Cys
115 120 125

Ile Asp Pro Ser Asn Pro Gly Cys Leu Thr Tyr Glu Ala Ser Asp Phe
130 135 140

Leu Ile Arg Glu Arg Pro Val Asn Val His Ser His Leu Ile Leu Phe
145 150 155 160

Gln Val Gly Cys Val Gly Ile Ala Asp Phe Asn Phe Ser Gly Phe Asp
165 170 175

Asn Ser Lys Phe Thr Ile Leu Val Asp Arg Leu Glu Gln Glu Tyr Gly
180 185 190

Pro Asp His Thr Val Val His Tyr Ile Ala Ala Met Met Pro His Gln
195 200 205

Asp Pro Val Thr Asp Lys Phe Thr Ile Gly Gln Leu Arg Glu
210 215 220

<210> SEQ ID NO 19
<211> LENGTH: 411
<212> TYPE: PRT
<213> ORGANISM: Fomitiporia mediterranea

<400> SEQUENCE: 19

Met Ala Thr Ser Thr Glu Thr Thr Glu Lys Lys Gly Ser Leu Thr Ile
1 5 10 15

Ala Gly Thr Gly Ile Ala Ser Ile Lys His Ile Thr Leu Glu Thr Leu
20 25 30

Ser Tyr Ile Lys Glu Ala Glu Lys Val Tyr Tyr Leu Val Ala Asp Pro
35 40 45

Ala Thr Glu Ala Phe Ile Gln Asp Asn Ala Ser Gly Thr Cys Phe Asn
50 55 60

Leu His Val Phe Tyr Asp Thr Asn Lys His Arg Tyr Asp Ser Tyr Val
65 70 75 80

Gln Met Ala Glu Val Met Leu Leu Asp Val Arg Ala Gly His Ser Val
85 90 95

-continued

```
Leu Gly Ile Phe Tyr Gly His Pro Gly Val Phe Val Ser Pro Ser His
            100                 105                 110

Arg Ala Ile Ala Ile Ala Arg Glu Glu Gly Phe Lys Ala His Met Leu
        115                 120                 125

Pro Gly Ile Ser Ala Glu Asp Tyr Met Phe Ala Asp Ile Gly Phe Asp
    130                 135                 140

Pro Ala Thr His Gly Cys Val Ser Tyr Glu Ala Thr Glu Leu Leu Val
145                 150                 155                 160

Arg Asp Lys Pro Leu Leu Pro Ser Ser His Asn Ile Ile Trp Gln Val
                165                 170                 175

Gly Ala Ile Gly Ala Asn Ala Met Val Phe Asp Asn Gly Lys Phe Asn
            180                 185                 190

Ile Leu Val Asp Arg Leu Glu Gln Val Phe Gly Pro Asp His Lys Val
        195                 200                 205

Val His Tyr Ile Gly Ala Val Leu Pro Gln Ser Thr Ser Thr Ile Glu
    210                 215                 220

Ala Tyr Thr Ile Ser Asp Leu Arg Lys Gly Asp Val Val Glu Lys Phe
225                 230                 235                 240

Ser Thr Thr Ser Thr Leu Tyr Val Pro Pro Ser Val Glu Ala Arg Leu
                245                 250                 255

Ser Gly Ile Met Val Arg Glu Leu Gly Leu Glu Asp Ser Gly Phe His
            260                 265                 270

Thr Lys Ser Ser Gln Ser Arg Thr Leu Trp Ala Gly Pro Val Thr Ser
        275                 280                 285

Ser Ala Pro Ala Tyr Gly Pro Gln Glu Arg Ile Val Ile Ala Gln Ile
    290                 295                 300

Asp Lys Asp Val Ile Pro Asp Ser His Gln Ile Leu Gln Ala Ser Asp
305                 310                 315                 320

Ala Met Lys Lys Thr Met Ala Asn Leu Ala Leu Asn Pro Lys Leu Ser
                325                 330                 335

Glu Glu Tyr Tyr Ala Ser Pro Ser Thr Val Val Glu Lys Val Thr Gly
            340                 345                 350

Leu Ser Glu Gln Glu Lys Lys Ala Leu Ile Leu Cys Ser Ala Gly Ala
        355                 360                 365

Ile His Met Val Met Ala Ala Thr Gln Thr Asn Ile Ala Gln Gly His
    370                 375                 380

Gln Trp Ser Ala Glu Glu Leu Glu Ala Ala Gly Thr Pro His Pro Ala
385                 390                 395                 400

Leu Ala Leu Leu Val Val Ile Ile Cys Leu Ile
                405                 410
```

<210> SEQ ID NO 20
<211> LENGTH: 196
<212> TYPE: PRT
<213> ORGANISM: Fomitiporia mediterranea

<400> SEQUENCE: 20

```
Leu Thr Ile Ala Gly Thr Gly Ile Ala Ser Ile Lys His Ile Thr Leu
1               5                   10                  15

Glu Thr Leu Ser Tyr Ile Lys Glu Ala Glu Lys Val Tyr Tyr Leu Val
            20                  25                  30

Ala Asp Pro Ala Thr Glu Ala Phe Ile Gln Asp Asn Ala Ser Gly Thr
        35                  40                  45

Cys Phe Asn Leu His Val Phe Tyr Asp Thr Asn Lys His Arg Tyr Asp
    50                  55                  60
```

Ser Tyr Val Gln Met Ala Glu Val Met Leu Leu Asp Val Arg Ala Gly
65 70 75 80

His Ser Val Leu Gly Ile Phe Tyr Gly His Pro Gly Val Phe Val Ser
85 90 95

Pro Ser His Arg Ala Ile Ala Ile Ala Arg Glu Glu Gly Phe Lys Ala
100 105 110

His Met Leu Pro Gly Ile Ser Ala Glu Asp Tyr Met Phe Ala Asp Ile
115 120 125

Gly Phe Asp Pro Ala Thr His Gly Cys Val Ser Tyr Glu Ala Thr Glu
130 135 140

Leu Leu Val Arg Asp Lys Pro Leu Leu Pro Ser Ser His Asn Ile Ile
145 150 155 160

Trp Gln Val Gly Ala Ile Gly Ala Asn Ala Met Val Phe Asp Asn Gly
165 170 175

Lys Phe Asn Ile Leu Val Asp Arg Leu Glu Gln Val Phe Gly Pro Asp
180 185 190

His Lys Val Val
195

<210> SEQ ID NO 21
<211> LENGTH: 535
<212> TYPE: PRT
<213> ORGANISM: Fomitiporia mediterranea

<400> SEQUENCE: 21

Met Ala Thr Ser Thr Glu Thr Ala Gln Lys Lys Gly Ser Leu Thr Ile
1 5 10 15

Ala Gly Thr Gly Ile Ala Ser Ile Lys His Ile Thr Leu Glu Thr Leu
20 25 30

Ser Tyr Ile Lys Glu Ala Glu Lys Val Tyr Tyr Leu Val Ala Asp Pro
35 40 45

Ala Thr Glu Ala Phe Ile His Asp Asn Ala Ser Gly Thr Cys Phe Asn
50 55 60

Leu His Val Phe Tyr Asp Thr Asn Lys Leu Arg Tyr Asp Ser Tyr Val
65 70 75 80

Gln Met Ala Glu Val Met Leu Arg Asp Val Arg Ala Gly Asn Ser Val
85 90 95

Leu Gly Leu Phe Tyr Gly His Pro Gly Val Phe Val Ser Pro Ser His
100 105 110

Arg Ala Ile Ala Val Ala Arg Glu Glu Gly Phe Lys Ala Gln Thr Leu
115 120 125

Pro Gly Ile Ser Ala Glu Asp Tyr Met Phe Ala Asp Ile Gly Phe Asp
130 135 140

Pro Ala Ser His Gly Cys Val Ser Tyr Glu Ala Thr Asp Leu Leu Ala
145 150 155 160

Arg Asp Lys Pro Leu Leu Pro Ser Ser His Asn Ile Ile Trp Gln Val
165 170 175

Gly Ala Ile Gly Ala Asn Ala Met Val Phe Asp Asn Gly Lys Phe Asn
180 185 190

Val Leu Val Asp Arg Leu Glu Arg Asp Phe Gly Pro Asn His Lys Val
195 200 205

Val His Tyr Ile Gly Ala Val Leu Pro Gln Ser Thr Ser Lys Val Glu
210 215 220

Gln Tyr Thr Val Ala Asp Leu Arg Lys Asp Tyr Val Val Lys Thr Phe

-continued

```
225                 230                 235                 240

Thr Thr Thr Ser Thr Leu Tyr Val Pro Pro Cys Val Asp Ala Gly Ile
                245                 250                 255

Ser Asn Ile Met Ala Arg Glu Leu Gly Leu Glu Asp Ser Thr Gly Leu
            260                 265                 270

Arg Thr Arg Gly Asn Gln Pro Leu Pro Leu Lys Thr Gly Pro Ala Ile
        275                 280                 285

Ser Leu Ala Ser Val Tyr Gly Ser His Glu Arg Thr Thr Ile Ala Gln
    290                 295                 300

Ile Asp Lys Gly Val Thr Pro Asp Thr Leu Gln Ile Leu Gln Ala Ser
305                 310                 315                 320

Asp Ala Met Lys Lys Leu Met Ala Asp Leu Ala Leu Lys Pro Lys Leu
                325                 330                 335

Leu Glu Lys Tyr Arg Gly Asn Pro Ser Val Val Ile Asp Glu Val Thr
            340                 345                 350

Gly Leu Ala Pro Gln Glu Lys Ala Ala Leu Thr Leu Cys Ser Ala Gly
        355                 360                 365

Ala Ile Tyr Met Val Met Ala Ala Ser Gln Ile Asp Ile Ala Lys Gly
    370                 375                 380

Leu Val Leu Val Lys Arg Ile Glu Glu Val Leu Leu Lys Asn Asn Ile
385                 390                 395                 400

Ser Ser Gly Arg Gly Gln Leu Ile Thr Ala Gly Ala Ile Tyr His Ser
                405                 410                 415

Ser Leu Ala Arg Leu Val Trp Gly Ala Gln Val Ala Pro Ala Glu Ile
            420                 425                 430

Glu Gln Val Leu Leu Ser His Pro Glu Gly Leu Val Ile Asp Ala Pro
        435                 440                 445

Leu Gln Glu Phe Arg Val Leu Gln Asn Val Thr Asn Ala Phe Phe Glu
    450                 455                 460

Cys Glu Ser Gly Gly Val Lys Ser Leu Asp Gly Arg Val Arg Glu Ser
465                 470                 475                 480

Leu Ser Arg Cys Lys Trp Leu Thr Gly Gly Ile Ala Val Val His Glu
                485                 490                 495

Ile Leu Lys Asn Pro Ile Gly Met Val Leu Arg Arg Met Leu Val Asp
            500                 505                 510

Glu Tyr Val Lys Lys Lys Ala Val Arg Glu Leu Pro Glu Lys Thr Leu
        515                 520                 525

Val Leu Arg Leu Pro Glu Asp
    530                 535
```

<210> SEQ ID NO 22
<211> LENGTH: 196
<212> TYPE: PRT
<213> ORGANISM: Fomitiporia mediterranea

<400> SEQUENCE: 22

```
Leu Thr Ile Ala Gly Thr Gly Ile Ala Ser Ile Lys His Ile Thr Leu
1               5                   10                  15

Glu Thr Leu Ser Tyr Ile Lys Glu Ala Glu Lys Val Tyr Tyr Leu Val
            20                  25                  30

Ala Asp Pro Ala Thr Glu Ala Phe Ile His Asp Asn Ala Ser Gly Thr
        35                  40                  45

Cys Phe Asn Leu His Val Phe Tyr Asp Thr Asn Lys Leu Arg Tyr Asp
    50                  55                  60
```

-continued

Ser Tyr Val Gln Met Ala Glu Val Met Leu Arg Asp Val Arg Ala Gly
65 70 75 80

Asn Ser Val Leu Gly Leu Phe Tyr Gly His Pro Gly Val Phe Val Ser
85 90 95

Pro Ser His Arg Ala Ile Ala Val Ala Arg Glu Glu Gly Phe Lys Ala
100 105 110

Gln Thr Leu Pro Gly Ile Ser Ala Glu Asp Tyr Met Phe Ala Asp Ile
115 120 125

Gly Phe Asp Pro Ala Ser His Gly Cys Val Ser Tyr Glu Ala Thr Asp
130 135 140

Leu Leu Ala Arg Asp Lys Pro Leu Leu Pro Ser Ser His Asn Ile Ile
145 150 155 160

Trp Gln Val Gly Ala Ile Gly Ala Asn Ala Met Val Phe Asp Asn Gly
165 170 175

Lys Phe Asn Val Leu Val Asp Arg Leu Glu Arg Asp Phe Gly Pro Asn
180 185 190

His Lys Val Val
195

<210> SEQ ID NO 23
<211> LENGTH: 432
<212> TYPE: PRT
<213> ORGANISM: Fomitiporia mediterranea

<400> SEQUENCE: 23

Met Ala Ala Thr Thr Glu Thr Met Lys Lys Gly Ser Leu Thr Ile Ala
1 5 10 15

Gly Ser Gly Ile Ala Ser Ile Lys His Met Thr Leu Glu Thr Val Ser
20 25 30

His Ile Lys Glu Ala Glu Lys Val Tyr Tyr Ile Val Thr Asp Pro Ala
35 40 45

Thr Glu Ala Tyr Ile Lys Asp Asn Ala Val Gly Ala Cys Phe Asp Leu
50 55 60

Arg Val Phe Tyr Asp Thr Asn Lys Pro Arg Tyr Glu Ser Tyr Val Gln
65 70 75 80

Met Ser Glu Val Met Leu Arg Asp Val Arg Val Gly His Ser Val Leu
85 90 95

Gly Ile Phe Tyr Gly His Pro Gly Val Phe Val Ser Pro Ser His Arg
100 105 110

Ala Ile Ala Ile Ala Lys Glu Glu Gly Phe Gln Ala Arg Met Leu Pro
115 120 125

Gly Ile Ser Ala Glu Asp Tyr Leu Phe Ala Asp Ile Gly Phe Asp Pro
130 135 140

Ala Ala His Gly Cys Met Ser Tyr Glu Ala Thr Glu Leu Leu Val Arg
145 150 155 160

Asn Lys Pro Leu Asn Thr Ser Thr His Asn Ile Ile Trp Gln Val Gly
165 170 175

Ala Leu Gly Ala Glu Ala Met Val Phe Asp Asn Ala Lys Phe Ser Leu
180 185 190

Leu Val Asp Arg Leu Glu Gln Asp Tyr Gly Ser Asp His Lys Val Val
195 200 205

His Tyr Ile Gly Ala Ile Leu Pro Gln Ala Asp Pro Thr Val Glu Ala
210 215 220

Tyr Ile Val Ala Asp Leu Arg Lys Glu Asp Val Val Lys Gln Phe Asn
225 230 235 240

Ala Ile Ser Thr Leu Tyr Ile Pro Pro Arg Val Ala Gly Lys Phe Leu
245 250 255

Asp Asp Met Ala Lys Lys Leu Gly Ile Ala Asp Ser Ala Ala Tyr Leu
260 265 270

Lys Asn His Tyr Pro Gln Ala Pro Tyr Thr Gly Pro Glu Phe Ala Thr
275 280 285

Asp Pro Ala Tyr Gly Pro Arg Glu Lys Ala Val Ile Asp Gln Ile Asp
290 295 300

Asn His Ala Ala Pro Glu Gly His Thr Val Leu His Ala Ser Asp Ala
305 310 315 320

Leu Lys Lys Leu Asn Thr Asp Leu Ala Leu Ser Pro Lys Phe Leu Glu
325 330 335

Glu Tyr Lys Glu Asn Pro Met Pro Ile Leu Glu Ala Met Asp Gly Leu
340 345 350

Thr Asn Glu Glu Lys Ala Ala Leu Met Gln Asn Pro Leu Gly Ala Thr
355 360 365

His Glu Leu Met Trp Ala Thr Pro Asp Glu Ile Ala Asn Gly Arg Ala
370 375 380

Leu Pro Val Val Asn Phe Met Ala Tyr Gly Gly Tyr Gly Gly Tyr Tyr
385 390 395 400

Gly Gly Gly Cys Arg Pro Cys Pro Cys Cys Val Val Thr Asp Arg Trp
405 410 415

Ser Ser Gly Gly Ser Asn Lys Cys Asn Met Val Asn Asn Leu Asn Val
420 425 430

<210> SEQ ID NO 24
<211> LENGTH: 196
<212> TYPE: PRT
<213> ORGANISM: Fomitiporia mediterranea

<400> SEQUENCE: 24

Leu Thr Ile Ala Gly Ser Gly Ile Ala Ser Ile Lys His Met Thr Leu
1 5 10 15

Glu Thr Val Ser His Ile Lys Glu Ala Glu Lys Val Tyr Tyr Ile Val
20 25 30

Thr Asp Pro Ala Thr Glu Ala Tyr Ile Lys Asp Asn Ala Val Gly Ala
35 40 45

Cys Phe Asp Leu Arg Val Phe Tyr Asp Thr Asn Lys Pro Arg Tyr Glu
50 55 60

Ser Tyr Val Gln Met Ser Glu Val Met Leu Arg Asp Val Arg Val Gly
65 70 75 80

His Ser Val Leu Gly Ile Phe Tyr Gly His Pro Gly Val Phe Val Ser
85 90 95

Pro Ser His Arg Ala Ile Ala Ile Ala Lys Glu Glu Gly Phe Gln Ala
100 105 110

Arg Met Leu Pro Gly Ile Ser Ala Glu Asp Tyr Leu Phe Ala Asp Ile
115 120 125

Gly Phe Asp Pro Ala Ala His Gly Cys Met Ser Tyr Glu Ala Thr Glu
130 135 140

Leu Leu Val Arg Asn Lys Pro Leu Asn Thr Ser Thr His Asn Ile Ile
145 150 155 160

Trp Gln Val Gly Ala Leu Gly Ala Glu Ala Met Val Phe Asp Asn Ala
165 170 175

Lys Phe Ser Leu Leu Val Asp Arg Leu Glu Gln Asp Tyr Gly Ser Asp

```
            180                 185                 190

His Lys Val Val
        195


<210> SEQ ID NO 25
<211> LENGTH: 421
<212> TYPE: PRT
<213> ORGANISM: Fomitiporia mediterranea

<400> SEQUENCE: 25

Met Ala Ala Thr Thr Glu Thr Thr Lys Lys Gly Ser Leu Thr Ile Ala
1               5                   10                  15

Gly Ser Gly Ile Ala Ser Ile Lys His Met Thr Leu Glu Thr Val Ser
            20                  25                  30

His Ile Lys Glu Val Glu Lys Val Tyr Tyr Ile Val Ser Asp Pro Ala
        35                  40                  45

Thr Glu Ala Tyr Ile Lys Asp Asn Ala Val Gly Thr Cys Phe Asp Leu
    50                  55                  60

Arg Val Phe Tyr Asp Thr Asn Lys Pro Arg Tyr Glu Ser Asp Val Gln
65                  70                  75                  80

Met Ser Glu Val Met Leu Arg Asp Val Arg Ala Gly His Ser Val Leu
                85                  90                  95

Gly Ile Phe Tyr Gly His Pro Gly Val Phe Val Ser Pro Ser His Arg
            100                 105                 110

Ala Ile Ala Ile Ala Lys Glu Glu Gly Phe Gln Ala Arg Met Leu Pro
        115                 120                 125

Gly Ile Ser Ala Glu Asp Tyr Leu Phe Ala Asp Ile Gly Phe Asp Pro
    130                 135                 140

Ala Val His Gly Cys Met Ser Tyr Glu Ala Thr Glu Leu Leu Val Arg
145                 150                 155                 160

Asn Lys Pro Leu Asn Thr Ser Thr Tyr Asn Ile Ile Trp Gln Val Gly
                165                 170                 175

Ala Leu Gly Ala Glu Ala Met Val Phe Asp Asn Ala Lys Phe Ser Leu
            180                 185                 190

Leu Val Asp Arg Leu Glu Arg Asp Tyr Gly Ser Asp His Lys Val Val
        195                 200                 205

His Tyr Ile Gly Ala Ile Leu Pro Gln Ala Asp Ser Thr Ile Glu Ala
    210                 215                 220

His Thr Val Ser Asp Leu Arg Lys Glu Asp Ile Val Lys Gln Phe Asn
225                 230                 235                 240

Ala Ile Ser Thr Leu Tyr Ile Pro Pro Arg Val Ala Gly Lys Phe Leu
                245                 250                 255

Asp Asp Met Val Glu Lys Leu Gly Ile Ala Asp Pro Ala Thr Phe Leu
            260                 265                 270

Lys Asn His Tyr Thr Gln Pro Pro Tyr Ser Gly Pro Glu Phe Ala Thr
        275                 280                 285

Asp Pro Ala Tyr Gly Pro Arg Glu Lys Ala Val Ile Asp Gln Ile Asp
    290                 295                 300

Asn His Ala Ala Pro Glu Gly His Thr Val Leu His Ala Thr Asp Ala
305                 310                 315                 320

Leu Lys Lys Leu Asn Thr Asp Leu Ala Leu Ser Pro Lys Phe Leu Lys
                325                 330                 335

Glu Tyr Lys Glu Asn Pro Met Pro Ile Leu Glu Ala Met Asp Gly Leu
            340                 345                 350
```

Thr Asp Glu Glu Gln Ala Ala Leu Met Gln Asn Pro Leu Gly Ala Thr
355 360 365

His Glu Leu Met Trp Ala Thr Pro Asp Glu Ile Ala Asn Gly Arg Val
370 375 380

Leu Pro Val Val Asn Phe Cys Phe Leu Gly Gly Asn Arg Arg Gly Tyr
385 390 395 400

Arg Arg Gly Tyr Gln Ala Val Asn Tyr Gly Gly Ser Tyr Asn Thr Tyr
405 410 415

Ile Ile Asn Asn Phe
420

<210> SEQ ID NO 26
<211> LENGTH: 196
<212> TYPE: PRT
<213> ORGANISM: Fomitiporia mediterranea

<400> SEQUENCE: 26

Leu Thr Ile Ala Gly Ser Gly Ile Ala Ser Ile Lys His Met Thr Leu
1 5 10 15

Glu Thr Val Ser His Ile Lys Glu Val Glu Lys Val Tyr Tyr Ile Val
20 25 30

Ser Asp Pro Ala Thr Glu Ala Tyr Ile Lys Asp Asn Ala Val Gly Thr
35 40 45

Cys Phe Asp Leu Arg Val Phe Tyr Asp Thr Asn Lys Pro Arg Tyr Glu
50 55 60

Ser Asp Val Gln Met Ser Glu Val Met Leu Arg Asp Val Arg Ala Gly
65 70 75 80

His Ser Val Leu Gly Ile Phe Tyr Gly His Pro Gly Val Phe Val Ser
85 90 95

Pro Ser His Arg Ala Ile Ala Ile Ala Lys Glu Glu Gly Phe Gln Ala
100 105 110

Arg Met Leu Pro Gly Ile Ser Ala Glu Asp Tyr Leu Phe Ala Asp Ile
115 120 125

Gly Phe Asp Pro Ala Val His Gly Cys Met Ser Tyr Glu Ala Thr Glu
130 135 140

Leu Leu Val Arg Asn Lys Pro Leu Asn Thr Ser Thr Tyr Asn Ile Ile
145 150 155 160

Trp Gln Val Gly Ala Leu Gly Ala Glu Ala Met Val Phe Asp Asn Ala
165 170 175

Lys Phe Ser Leu Leu Val Asp Arg Leu Glu Arg Asp Tyr Gly Ser Asp
180 185 190

His Lys Val Val
195

<210> SEQ ID NO 27
<211> LENGTH: 417
<212> TYPE: PRT
<213> ORGANISM: Dendrothele bispora

<400> SEQUENCE: 27

Met Pro Val Arg Ile Pro Ser Pro Gln Lys Glu Ala Gly Ser Leu Thr
1 5 10 15

Ile Val Gly Thr Gly Ile Glu Ser Ile Gly Gln Ile Thr Leu Gln Ala
20 25 30

Ile Ser His Ile Glu Thr Ala Ser Lys Val Phe Tyr Cys Val Val Asp
35 40 45

-continued

```
Pro Ala Thr Glu Ala Phe Ile Arg Thr Lys Asn Lys Asn Cys Phe Asp
    50                  55                  60

Leu Tyr Pro Tyr Tyr Asp Asn Gly Lys His Arg Met Asp Thr Tyr Ile
65                  70                  75                  80

Gln Met Ala Glu Val Met Leu Lys Glu Val Arg Asn Gly Leu Asp Val
                85                  90                  95

Val Gly Val Phe Tyr Gly His Pro Gly Val Phe Val Ser Pro Ser His
            100                 105                 110

Arg Ala Leu Ala Ile Ala Glu Ser Glu Gly Tyr Lys Ala Arg Met Leu
        115                 120                 125

Pro Gly Val Ser Ala Glu Asp Cys Leu Phe Ala Asp Leu Arg Ile Asp
    130                 135                 140

Pro Ser His Pro Gly Cys Met Thr Tyr Glu Ala Ser Asp Phe Leu Ile
145                 150                 155                 160

Arg Glu Arg Pro Val Asn Ile His Ser His Leu Val Leu Trp Gln Val
                165                 170                 175

Gly Cys Val Gly Val Ala Asp Phe Asn Ser Gly Gly Phe Lys Asn Thr
            180                 185                 190

Lys Phe Asp Val Leu Val Asp Arg Leu Glu Gln Glu Tyr Gly Ala Asp
        195                 200                 205

His Pro Val Val His Tyr Met Ala Ser Ile Leu Pro Tyr Glu Asp Pro
    210                 215                 220

Val Thr Asp Lys Phe Thr Val Ser Gln Phe Arg Asp Pro Gln Ile Ala
225                 230                 235                 240

Lys Arg Ile Cys Gly Ile Ser Thr Phe Tyr Ile Pro Pro Lys Glu Thr
                245                 250                 255

Lys Asp Ser Asn Val Glu Ala Met His Arg Leu Gln Leu Leu Pro Ser
            260                 265                 270

Gly Lys Gly Val Leu Lys Glu Thr Gly Arg Tyr Pro Ser Asn Lys Trp
        275                 280                 285

Ala Pro Ser Gly Ser Phe His Asp Val Asp Pro Tyr Gly Pro Arg Glu
    290                 295                 300

Leu Ala Ala Val Thr Lys Leu Lys Ser His Thr Ile Pro Glu His Tyr
305                 310                 315                 320

Gln Pro Leu Ala Thr Ser Lys Ala Met Thr Asp Val Met Thr Lys Leu
                325                 330                 335

Ala Leu Asp Pro Arg Val Leu Ser Glu Tyr Lys Ala Ser Arg Gln Asp
            340                 345                 350

Phe Val His Ser Val Pro Gly Leu Thr Pro Asn Glu Lys Asn Ala Leu
        355                 360                 365

Val Lys Gly Glu Ile Ala Ala Ile Arg Cys Gly Met Lys Asn Ile Pro
    370                 375                 380

Ile Ser Glu Lys Gln Trp Glu Leu Arg Asp Gly Leu Val Thr Lys Phe
385                 390                 395                 400

Ile Val Val Pro Ile Trp Val Ser Ile Asp Asp Thr Thr Gly Asn Leu
                405                 410                 415

Glu


<210> SEQ ID NO 28
<211> LENGTH: 198
<212> TYPE: PRT
<213> ORGANISM: Dendrothele bispora

<400> SEQUENCE: 28
```

-continued

```
Leu Thr Ile Val Gly Thr Gly Ile Glu Ser Ile Gly Gln Ile Thr Leu
1               5                   10                  15

Gln Ala Ile Ser His Ile Glu Thr Ala Ser Lys Val Phe Tyr Cys Val
            20                  25                  30

Val Asp Pro Ala Thr Glu Ala Phe Ile Arg Thr Lys Asn Lys Asn Cys
        35                  40                  45

Phe Asp Leu Tyr Pro Tyr Tyr Asp Asn Gly Lys His Arg Met Asp Thr
    50                  55                  60

Tyr Ile Gln Met Ala Glu Val Met Leu Lys Glu Val Arg Asn Gly Leu
65                  70                  75                  80

Asp Val Val Gly Val Phe Tyr Gly His Pro Gly Val Phe Val Ser Pro
                85                  90                  95

Ser His Arg Ala Leu Ala Ile Ala Glu Ser Glu Gly Tyr Lys Ala Arg
            100                 105                 110

Met Leu Pro Gly Val Ser Ala Glu Asp Cys Leu Phe Ala Asp Leu Arg
        115                 120                 125

Ile Asp Pro Ser His Pro Gly Cys Met Thr Tyr Glu Ala Ser Asp Phe
    130                 135                 140

Leu Ile Arg Glu Arg Pro Val Asn Ile His Ser His Leu Val Leu Trp
145                 150                 155                 160

Gln Val Gly Cys Val Gly Val Ala Asp Phe Asn Ser Gly Gly Phe Lys
                165                 170                 175

Asn Thr Lys Phe Asp Val Leu Val Asp Arg Leu Glu Gln Glu Tyr Gly
            180                 185                 190

Ala Asp His Pro Val Val
        195
```

<210> SEQ ID NO 29
<211> LENGTH: 2238
<212> TYPE: DNA
<213> ORGANISM: Omphalotus olearius

<400> SEQUENCE: 29

```
atgtcgtttc caggatgggg accatatcca cctgttgaaa gggacgaaac ttcagcgata      60

acttacagta gcaagttgca tggctctgtt acggttcgtg atccctacag tcaacttgaa     120

gtacctttcg aggatagtga agaaacgaag gcgtttgttc attcacaacg caagtttgca     180

cgaacctatc tagatgaaaa tcccgatcga gaagcatggc tcgagacgct gaagaagagc     240

tggaattaca ggagatttag cgcattgaaa cctgaaagcg acggacatta ctacttcgag     300

tataacgatg gccttcaatc tcagctttcc ctgtatcgtg tgaggatggg ggaggaggat     360

accgtcctcg ctgagtctgg tcctggtgga gaactctttt tcaatcccaa cttgctctcc     420

cttgatggca acgccgcact tactggtttc gtcatgagtc catgtgggaa ttattgggca     480

tatggcgtat ctgaacatgg atccgactgg atgtctattt acgttcgaaa gacgtcgtct     540

ccgcatcttc cgtcacaaga acgaggaaag gatcctggac ggatgaacga caagattcga     600

cacgtccgtt tcttcattgt atcttggaca agtgacagca aaggcttttt ctattctagg     660

tatcctcctg aggatgacga agggaaaggt aatgcaccag caatgaattg catggtctat     720

tatcatcgga ttggcgagga tcaggagagt gacgtccttg ttcatgagga tcctgagcat     780

ccgttctgga tctcgtcggt gcagctcact ccgagcggcc gatacatcct ctttgccgcg     840

agccgcgacg caagtcacac tcaattagtc aagatcgcag atcttcacga aaatgacatt     900

gggacgaata tgaaatggaa aaaccttcat gatccatggg aggccaggtt tacaatagtc     960
```

-continued

```
ggagacgagg gttcaaagat ctatttcatg accaatctca aggccaagaa ctacaaagtg   1020

gcgacgtttg atgccaacca ccccgacgag ggtctgacga cgctcatagc agaagaccct   1080

agcgcgtttc tcgtttcagc aagcattcac gcccaagaca agctcctact tgtttatctt   1140

cgtaatgcca gccacgagat tcatatccgt gatctaacca ctgggaaacc cctcgggcgt   1200

atctttgagg atttacttgg acagttcatg atatcaggtc gacggcagga taacgatatt   1260

ttcgttctct ttagcagttt cctctctcct ggaacggtgt atcggtacac gttcggtgaa   1320

gagaaaggat accgttcact atttcgtgct atcagtattc cgggcctcaa tctagatgac   1380

tttatgacag agtcggtttt ctatccatcc aaggacggga cttctgttca catgtttatc   1440

acccgcccga aggatgtact gctcgatgga acttcccctg tcctacaata cggctatggc   1500

ggtttctccc tagcaatgct tcctacattc tccctctcta cgctgctatt ctgcaaaatt   1560

tacagggcga tctatgcgat acccaatatt cgtggtggtt cggaatacgg cgagtcatgg   1620

caccgggagg gtatgttaga caagaagcag aacgtgtttg acgacttcaa cgctgcaacc   1680

gaatggctta ttgcgaataa gtacgcaagc aaggatcgca ttgccatccg aggaggatca   1740

aatggaggtg ttttgaccac tgcatgtgca aatcaagcac cgggactcta ccgttgtgtg   1800

atcacaattg agggtataat tgatatgctt agatttccta agtttacatt tggcgctagc   1860

tggcgttctg aatatggtga tcctgaggat cctgaagatt tcgacttcat attcaaatac   1920

tccccctatc acaacatccc tcccccggga gacactatta tgccagccat gctattcttt   1980

actgcggcgt atgatgatcg tgtctcgcct ttgcacacgt tcaagcacgt tgcggcagtg   2040

caacacaact ttcccaaagg cccgaatcca tgcctaatgc gcatcgactt gaattcggga   2100

cactttgctg gcaagagtac gcaggagatg ttggaagaaa cggcagatga atacagcttc   2160

atcgggaagt ctatgggcct cactatgcag actcaaggtt cagtggattc aagccgctgg   2220

tcctgcgtaa cagtttga                                                2238
```

<210> SEQ ID NO 30
<211> LENGTH: 615
<212> TYPE: DNA
<213> ORGANISM: Omphalotus olearius

<400> SEQUENCE: 30

```
atctatgcga tacccaatat tcgtggtggt tcggaatacg gcgagtcatg gcaccgggag     60

ggtatgttag acaagaagca gaacgtgttt gacgacttca acgctgcaac cgaatggctt    120

attgcgaata agtacgcaag caaggatcgc attgccatcc gaggaggatc aaatggaggt    180

gttttgacca ctgcatgtgc aaatcaagca ccgggactct accgttgtgt gatcacaatt    240

gagggtataa ttgatatgct tagatttcct aagtttacat ttggcgctag ctggcgttct    300

gaatatggtg atcctgagga tcctgaagat ttcgacttca tattcaaata ctccccctat    360

cacaacatcc ctcccccggg agacactatt atgccagcca tgctattctt tactgcggcg    420

tatgatgatc gtgtctcgcc tttgcacacg ttcaagcacg ttgcggcagt gcaacacaac    480

tttcccaaag gcccgaatcc atgcctaatg cgcatcgact tgaattcggg acactttgct    540

ggcaagagta cgcaggagat gttggaagaa acggcagatg aatacagctt catcgggaag    600

tctatgggcc tcact                                                     615
```

<210> SEQ ID NO 31
<211> LENGTH: 1512
<212> TYPE: DNA
<213> ORGANISM: Omphalotus olearius

<400> SEQUENCE: 31
atgttcttca ccttttcaac atcttacatc gctctggtcg tcgccgttct tgtcgttgcc 60
cgctcaatcg ttaccttgcg tgctaaacac aagcttgatc tgccaaccat cggaggggca 120
ggactcgtcc agtcttatgt cgctgcgtac aaatttcttt tcggatcccg cgatctcatt 180
caagaaggtt atgaaaagta ttatgggaag gctttcaaag ttcctatgtt agctggctgg 240
caaattcttg tcacaggacc gcgtatgatg gaggaaattc gaatggctcc cgagctttct 300
acccgtgaat ccctattcag agagtgccta cagatggact ataccttcgg ccctgaacat 360
ctcattaacc catatcattt tcaatttgta caaatctctc tcggacgaga tattggtctt 420
cgaatacccg ctctacaaga ggaaattgta acgttatttt cggaactcat tcctcaaacg 480
aaagattgga ttagactccc gggagcgtct actgggcagc aaatcgcgtt cagaacaacg 540
actaggcttc ttgttgggct tccactatgc cgggaccaag actacaagac actcaatgat 600
caatggcctg attctctggc caaggctgcg atcaccatta gcgttgttcc tcagtttctg 660
aaatcgttcg tttctcgttc tcttcccttt taccgatcag tgttagatcg cgcaatgaac 720
catgtgcgtc ctttgttgga ggagcgcttt gaaaagcaag gaccattcgg cgatgatgca 780
ccggataaat cggacgacct tcttacctgg ttgatgaaga aagcgccaac aaacgagaag 840
tcactcgaag ccattacgag gcgccttatg gcaacacact tcgtgactta tcgtccgcta 900
tcgctcgcta caacggaagt gctgtatgat ctagcagcgc atccatctta cgtccctgag 960
ctacgagaag aagttgaagc tcttgtacgc gagcacggtg ttacgaagga aggtttggat 1020
aagatgtata agcttgatag cttcgttaag gaatgtctgc gcctccattc gagcccaaag 1080
atcaccatgt cacgtaaagt tatgaaagac ttcacctttt ccgatgggac caccattcca 1140
gcaggaaata cgattgctgt ggcgggctat gccattcatc acgatgagag aagctttcct 1200
aatcccgagg aattcgatgg gttcagatat tttaggaaac aggacgaaga acaggaaccg 1260
ggaaaacatc agctggttac tctcgctcac gactatgtcc tctttggagg tggtagacac 1320
gcctgtccgg gacgtttttt ggtcgctgcg atactcaaga cgatgctcgt gcatgtacta 1380
cttacgtacg atgtgaagct ggaggaagaa ggtgtacgcc ccccagatga atggcctggg 1440
atgttggttg cagtacctaa ccaaactgca ggagttttgg tgagaagacg agaactatct 1500
tcttgggaat ga 1512

<210> SEQ ID NO 32
<211> LENGTH: 1122
<212> TYPE: DNA
<213> ORGANISM: Omphalotus olearius

<400> SEQUENCE: 32
atgagttata gtcgaatcct tgtccttgct gctgtgtcca aatgcatatc gacatttgga 60
atcgtgaccc cgccttcccc gcaccgatgg atgcttttcg tgcctatcgt cgtaatcaat 120
gcttactgtt acttcagcac tttcaccgac gataccatgc gtaggaacgc cgtcatagaa 180
actttggttg cttcggattt cttggtcctt acggacgttc agcgcgaatt ccgtcaggtt 240
ggacagcggg aacctatctc gaaactcggg ctttgggctc gattacaatg ggctctccgg 300
ctactactct cccctcgagg tgtaggatgg acgtatgaac ccacatcagc tcttccttct 360
cgccacaacc ttccgcggcg cacgttcctt cggactcagc tcattcttct tgtatgggct 420
atcattggaa acgatcttgc ctacattctt acctccaagg atccaggctt cgccaaacat 480

```
gcacgtccgt ttagcgagca gcctctcgtc tggcgtttct gggcaactgc cgtcttcttt    540

ttcaagatca gaaagtgtac cgaagtttat tacttcttcg tagccttcgt acttgtcggg    600

gtcaacatgt cagagccaag ctcttggccg gaatttttg gaagttggtc ggatgcatat    660

actgttcgtc gttggtgggg aagagtatgg catcaaagtc tgcgcaggat gtttgcttcg    720

cacgggaagt acctagctca tcgtgtcttc ggttttcgcc caggatcccc agcgtcttcg    780

tacactcagc tctatgtcgc ctttttctta tcggggatca ttcatgtgac gtcgtacgat    840

ccacgtccca tatggtattt catgtctcag gcagtcacga tcacctttga ggaaatcgtt    900

ctcaccatag cgaagaaagc tggtgtaaaa agctcgaagg gtactcgtct gctgggttat    960

gtttgggtgt actgcaacct ggtgttcact ttgggcccac tcttcgattc catgaatgca   1020

gtcggacttg gtttgggagg gtacgatggg acaatcttgc taggtcgtta tcgtgactcg   1080

gagtggatga cggggttgct gtctcatgcg actgcaaatt ga                      1122
```

<210> SEQ ID NO 33
<211> LENGTH: 1497
<212> TYPE: DNA
<213> ORGANISM: Omphalotus olearius

<400> SEQUENCE: 33

```
atggccgacg agtgggagga attgttatct tggctcgtat cgagacttca atttgacctc     60

tatgtccagt acagcgcgaa tagagcactt ggaagcttcg ttctgctgct cggaatcgct    120

atccttgtcc ttttcacgaa gaaaatcaaa gagatataca tcgacttcct tgccattgca    180

tatggttacg acttgatgag atcccgcttc aaatacggcg agaacgtttt tcatttccat    240

ctctttggta atctcgtcat cggattacga ggtcagaaag cacggagagt gttgttcgaa    300

gagaagaact tcagtagtag tgatggatac aagatgttca gcaaagtagt ccctattcct    360

gaggtcacgt ttgccccgga acaagaagat tacaccttgg cattcaagaa gcacctgggt    420

actctgctgg ggaaggatag gcttaatgac ataattgtta ccatgtttcg agacatagaa    480

cgtgtcatgg aaacttgggg cgagaaaggc gctatggatc cgttcaataa catcaacgac    540

atcgcgtttc tgttgaccgt gcatatggtt accagcgacg aattcgtttc ggatctctct    600

gctctgtctc gttttcaaag ccacttttcc agacagctaa gcagtcatac cccggaacg    660

atttcttcc catggttcta tcggacagct cagcgcgagc gagagaagtc cgtaatggcc    720

ctcttcaata cattaaccga acacatcgag gcacgaaaag ggcgtaccgc accgacacct    780

gaagctgtcg atcttttact ggcccgtgga ctgaatactc aagagatttt ccagtttatc    840

cttggattct tattcggagg tgcttttaat acaaccaaag cgacgtcatg gattcttctt    900

tatctcgcac tccatcctca gtggggctct actattcgct ccgaaataga gaccgttctc    960

tctcgcacat caattgacaa ctctgaatcg atgtgcagca ggctttcttc aatctctgtc   1020

gaagattggg aaagctcaat gcctacactc gaccttgtca tatctgaaac tcttcgattg   1080

gtcatgaatc aaaccgtgct tcggcgcaat atgggcgaga agttgaagat agatggtatg   1140

ggcgaaatac cgagaggcgc atttctgatc tacagtaatg ccgatgcgca tttgaacccc   1200

gagctgtatc ctgatccttg gacattcaac ccccagcact tcagtcaggg taaggaagat   1260

gatgagtatg cgttcttggg gtggggcgcg gggaggcacc ggtgtgttgg ggttaagatt   1320

gcaaaattgg caatcaaggc gattgtctcg tcattcataa tgacttatga gcacgatgtc   1380

atcagctcaa atcgcaaagt cacctcgaaa actcccattc ccgattataa caagataaac   1440

aatggacacc cgaagaatgg agtgtattcc atcagctata gtaggcgcgt aggatga      1497
```

<210> SEQ ID NO 34
<211> LENGTH: 1164
<212> TYPE: DNA
<213> ORGANISM: Omphalotus olearius

<400> SEQUENCE: 34
atgttcagca aagtagtccc tattcctgag gtcacgtttg ccccggaaca agaagattac 60
accttggcat tcaagaagca cctgggtact ctgctgggga aggataggct taatgacata 120
attgttacca tgtttcgaga catagaacgt gtcatggaaa cttggggcga gaaaggcgct 180
atggatccgt tcaataacat caacgacatc gcgtttctgt tgaccgtgca tatggttacc 240
agcgacgaat tcgtttcgga tctctctgct ctgtctcgtt ttcaaagcca cttttccaga 300
cagctaagca gtcatacccc cggaacgatt ttcttcccat ggttctatcg gacagctcag 360
cgcgagcgag agaagtccgt aatggccctc ttcaatacat taaccgaaca catcgaggca 420
cgaaaagggc gtaccgcacc gacacctgaa gctgtcgatc ttttactggc ccgtggactg 480
aatactcaag agattttcca gtttatcctt ggattcttat tcggaggtgc ttttaataca 540
accaaagcga cgtcatggat tcttctttat ctcgcactcc atcctcagtg gggctctact 600
attcgctccg aaatagagac cgttctctct cgcacatcaa ttgacaactc tgaatcgatg 660
tgcagcaggc tttcttcaat ctctgtcgaa gattgggaaa gctcaatgcc tacactcgac 720
cttgtcatat ctgaaactct tcgattggtc atgaatcaaa ccgtgcttcg gcgcaatatg 780
ggcgagaagt tgaagataga tggtatgggc gaaataccga gaggcgcatt tctgatctac 840
agtaatgccg atgcgcattt gaaccccgag ctgtatcctg atccttggac attcaacccc 900
cagcacttca gtcagggtaa ggaagatgat gagtatgcgt tcttggggtg gggcgcgggg 960
aggcaccggt gtgttggggt taagattgca aaattggcaa tcaaggcgat tgtctcgtca 1020
ttcataatga cttatgagca cgatgtcatc agctcaaatc gcaaagtcac ctcgaaaact 1080
cccattcccg attataacaa gataaacaat ggacacccga agaatggagt gtattccatc 1140
agctatagta ggcgcgtagg atga 1164

<210> SEQ ID NO 35
<211> LENGTH: 1251
<212> TYPE: DNA
<213> ORGANISM: Omphalotus olearius

<400> SEQUENCE: 35
atgtttgcct tgcctgttga tgttcatgaa gctattattc gcgagctctt tgccagaaag 60
gacaaggcga ccgtaaagtc tttatcgctt gtatgctcct ccctgacgca tatttgccaa 120
cggcacctcc tctcgcatct caccatcacc tgtcctacag cacaacgcaa atacgaacgg 180
gaccagcgct cgagtcacgc aacgcaggag ctactccaat catcacctca cctcatccca 240
atcattcgat cgttgtccat catcgcctct agcacaactt ggagacagat cgatgtcgct 300
ctcctataca tcctcgaaac gctcacgaat ctgaacgagt ttacttggaa agcttcatcg 360
gtttcatcgc acccagctcg ctgggcggaa ctaccccatc tattgcagga cgcagtaaag 420
gatgcaattc ggcgtccttc gttgacctcg ctagttctcc atttcgctga cttgactgaa 480
ctgttaaatg caacgatcat cgtgtcaccc tctttaaggc aattaaggct acagggcact 540
ggctattcaa atctcacctt ggaactgacc cgtcccagca taataccttg cgacgatgcg 600
ggtgaaccaa atctgcagga actttttgtc acgtcatgca agctagagtg gattgatgat 660

-continued

```
gacgagatgt tctttggctg gatgaacact gtccaaccgc atctcagcct cacgcgactt    720

cacaagctcg ccgtgctccg ctgcatactt aattcgacgc aagtagagct gccctggggg    780

ccgttgttat atcacgaatc cgttcggtcg aagctggagg agttatggtt cgatcttggg    840

tccacgcgtg gtcctccagc tggtactgta tatctcgacc agctgccgtc cttacgacga    900

cttgggctga ccgcagagct ttcgggtatg gctgccacct ggaacttgtt atctgggatt    960

gctcagtttt tcgagggcga gaacaacgtt gagattactc accttgccct tgtcttcagc   1020

ttctccacca cttctctcgt actaaacccg ctcagcatgc cgtggtcgcg attggacgca   1080

gctgtcgcag cgttgcccta cttgaaatgg gttgggattc aggtcatcga ttgtagatgc   1140

cagccttgca tgatgatccc tgaaaattcg gaatttttgc tgccaatgct tgcggagcag   1200

ggagttttgc actggtcaac gagcgggttg gagtttccag cacaaaagta g            1251


<210> SEQ ID NO 36
<211> LENGTH: 745
<212> TYPE: PRT
<213> ORGANISM: Omphalotus olearius

<400> SEQUENCE: 36

Met Ser Phe Pro Gly Trp Gly Pro Tyr Pro Pro Val Glu Arg Asp Glu
1               5                   10                  15

Thr Ser Ala Ile Thr Tyr Ser Ser Lys Leu His Gly Ser Val Thr Val
            20                  25                  30

Arg Asp Pro Tyr Ser Gln Leu Glu Val Pro Phe Glu Asp Ser Glu Glu
        35                  40                  45

Thr Lys Ala Phe Val His Ser Gln Arg Lys Phe Ala Arg Thr Tyr Leu
    50                  55                  60

Asp Glu Asn Pro Asp Arg Glu Ala Trp Leu Glu Thr Leu Lys Lys Ser
65                  70                  75                  80

Trp Asn Tyr Arg Arg Phe Ser Ala Leu Lys Pro Glu Ser Asp Gly His
                85                  90                  95

Tyr Tyr Phe Glu Tyr Asn Asp Gly Leu Gln Ser Gln Leu Ser Leu Tyr
            100                 105                 110

Arg Val Arg Met Gly Glu Glu Asp Thr Val Leu Ala Glu Ser Gly Pro
        115                 120                 125

Gly Gly Glu Leu Phe Phe Asn Pro Asn Leu Leu Ser Leu Asp Gly Asn
    130                 135                 140

Ala Ala Leu Thr Gly Phe Val Met Ser Pro Cys Gly Asn Tyr Trp Ala
145                 150                 155                 160

Tyr Gly Val Ser Glu His Gly Ser Asp Trp Met Ser Ile Tyr Val Arg
                165                 170                 175

Lys Thr Ser Ser Pro His Leu Pro Ser Gln Glu Arg Gly Lys Asp Pro
            180                 185                 190

Gly Arg Met Asn Asp Lys Ile Arg His Val Arg Phe Phe Ile Val Ser
        195                 200                 205

Trp Thr Ser Asp Ser Lys Gly Phe Phe Tyr Ser Arg Tyr Pro Pro Glu
    210                 215                 220

Asp Asp Glu Gly Lys Gly Asn Ala Pro Ala Met Asn Cys Met Val Tyr
225                 230                 235                 240

Tyr His Arg Ile Gly Glu Asp Gln Glu Ser Asp Val Leu Val His Glu
                245                 250                 255

Asp Pro Glu His Pro Phe Trp Ile Ser Ser Val Gln Leu Thr Pro Ser
            260                 265                 270
```

-continued

```
Gly Arg Tyr Ile Leu Phe Ala Ala Ser Arg Asp Ala Ser His Thr Gln
        275                 280                 285

Leu Val Lys Ile Ala Asp Leu His Glu Asn Asp Ile Gly Thr Asn Met
    290                 295                 300

Lys Trp Lys Asn Leu His Asp Pro Trp Glu Ala Arg Phe Thr Ile Val
305                 310                 315                 320

Gly Asp Glu Gly Ser Lys Ile Tyr Phe Met Thr Asn Leu Lys Ala Lys
                325                 330                 335

Asn Tyr Lys Val Ala Thr Phe Asp Ala Asn His Pro Asp Glu Gly Leu
            340                 345                 350

Thr Thr Leu Ile Ala Glu Asp Pro Ser Ala Phe Leu Val Ser Ala Ser
        355                 360                 365

Ile His Ala Gln Asp Lys Leu Leu Leu Val Tyr Leu Arg Asn Ala Ser
    370                 375                 380

His Glu Ile His Ile Arg Asp Leu Thr Thr Gly Lys Pro Leu Gly Arg
385                 390                 395                 400

Ile Phe Glu Asp Leu Leu Gly Gln Phe Met Ile Ser Gly Arg Arg Gln
                405                 410                 415

Asp Asn Asp Ile Phe Val Leu Phe Ser Ser Phe Leu Ser Pro Gly Thr
            420                 425                 430

Val Tyr Arg Tyr Thr Phe Gly Glu Glu Lys Gly Tyr Arg Ser Leu Phe
        435                 440                 445

Arg Ala Ile Ser Ile Pro Gly Leu Asn Leu Asp Asp Phe Met Thr Glu
    450                 455                 460

Ser Val Phe Tyr Pro Ser Lys Asp Gly Thr Ser Val His Met Phe Ile
465                 470                 475                 480

Thr Arg Pro Lys Asp Val Leu Leu Asp Gly Thr Ser Pro Val Leu Gln
                485                 490                 495

Tyr Gly Tyr Gly Gly Phe Ser Leu Ala Met Leu Pro Thr Phe Ser Leu
            500                 505                 510

Ser Thr Leu Leu Phe Cys Lys Ile Tyr Arg Ala Ile Tyr Ala Ile Pro
        515                 520                 525

Asn Ile Arg Gly Gly Ser Glu Tyr Gly Glu Ser Trp His Arg Glu Gly
    530                 535                 540

Met Leu Asp Lys Lys Gln Asn Val Phe Asp Asp Phe Asn Ala Ala Thr
545                 550                 555                 560

Glu Trp Leu Ile Ala Asn Lys Tyr Ala Ser Lys Asp Arg Ile Ala Ile
                565                 570                 575

Arg Gly Gly Ser Asn Gly Gly Val Leu Thr Thr Ala Cys Ala Asn Gln
            580                 585                 590

Ala Pro Gly Leu Tyr Arg Cys Val Ile Thr Ile Glu Gly Ile Ile Asp
        595                 600                 605

Met Leu Arg Phe Pro Lys Phe Thr Phe Gly Ala Ser Trp Arg Ser Glu
    610                 615                 620

Tyr Gly Asp Pro Glu Asp Pro Glu Asp Phe Asp Phe Ile Phe Lys Tyr
625                 630                 635                 640

Ser Pro Tyr His Asn Ile Pro Pro Pro Gly Asp Thr Ile Met Pro Ala
                645                 650                 655

Met Leu Phe Phe Thr Ala Ala Tyr Asp Asp Arg Val Ser Pro Leu His
            660                 665                 670

Thr Phe Lys His Val Ala Ala Val Gln His Asn Phe Pro Lys Gly Pro
        675                 680                 685

Asn Pro Cys Leu Met Arg Ile Asp Leu Asn Ser Gly His Phe Ala Gly
```

```
    690                 695                 700

Lys Ser Thr Gln Glu Met Leu Glu Glu Thr Ala Asp Glu Tyr Ser Phe
705                 710                 715                 720

Ile Gly Lys Ser Met Gly Leu Thr Met Gln Thr Gln Gly Ser Val Asp
                725                 730                 735

Ser Ser Arg Trp Ser Cys Val Thr Val
            740                 745


<210> SEQ ID NO 37
<211> LENGTH: 205
<212> TYPE: PRT
<213> ORGANISM: Omphalotus olearius

<400> SEQUENCE: 37

Ile Tyr Ala Ile Pro Asn Ile Arg Gly Gly Ser Glu Tyr Gly Glu Ser
1               5                   10                  15

Trp His Arg Glu Gly Met Leu Asp Lys Lys Gln Asn Val Phe Asp Asp
            20                  25                  30

Phe Asn Ala Ala Thr Glu Trp Leu Ile Ala Asn Lys Tyr Ala Ser Lys
        35                  40                  45

Asp Arg Ile Ala Ile Arg Gly Gly Ser Asn Gly Gly Val Leu Thr Thr
    50                  55                  60

Ala Cys Ala Asn Gln Ala Pro Gly Leu Tyr Arg Cys Val Ile Thr Ile
65                  70                  75                  80

Glu Gly Ile Ile Asp Met Leu Arg Phe Pro Lys Phe Thr Phe Gly Ala
                85                  90                  95

Ser Trp Arg Ser Glu Tyr Gly Asp Pro Glu Asp Pro Glu Asp Phe Asp
            100                 105                 110

Phe Ile Phe Lys Tyr Ser Pro Tyr His Asn Ile Pro Pro Pro Gly Asp
        115                 120                 125

Thr Ile Met Pro Ala Met Leu Phe Phe Thr Ala Ala Tyr Asp Asp Arg
    130                 135                 140

Val Ser Pro Leu His Thr Phe Lys His Val Ala Ala Val Gln His Asn
145                 150                 155                 160

Phe Pro Lys Gly Pro Asn Pro Cys Leu Met Arg Ile Asp Leu Asn Ser
                165                 170                 175

Gly His Phe Ala Gly Lys Ser Thr Gln Glu Met Leu Glu Glu Thr Ala
            180                 185                 190

Asp Glu Tyr Ser Phe Ile Gly Lys Ser Met Gly Leu Thr
        195                 200                 205


<210> SEQ ID NO 38
<211> LENGTH: 503
<212> TYPE: PRT
<213> ORGANISM: Omphalotus olearius

<400> SEQUENCE: 38

Met Phe Phe Thr Phe Ser Thr Ser Tyr Ile Ala Leu Val Val Ala Val
1               5                   10                  15

Leu Val Val Ala Arg Ser Ile Val Thr Leu Arg Ala Lys His Lys Leu
            20                  25                  30

Asp Leu Pro Thr Ile Gly Gly Ala Gly Leu Val Gln Ser Tyr Val Ala
        35                  40                  45

Ala Tyr Lys Phe Leu Phe Gly Ser Arg Asp Leu Ile Gln Glu Gly Tyr
    50                  55                  60

Glu Lys Tyr Tyr Gly Lys Ala Phe Lys Val Pro Met Leu Ala Gly Trp
```

-continued

```
65                  70                  75                  80

Gln Ile Leu Val Thr Gly Pro Arg Met Met Glu Glu Ile Arg Met Ala
                85                  90                  95

Pro Glu Leu Ser Thr Arg Glu Ser Leu Phe Arg Glu Cys Leu Gln Met
            100                 105                 110

Asp Tyr Thr Phe Gly Pro Glu His Leu Ile Asn Pro Tyr His Phe Gln
        115                 120                 125

Phe Val Gln Ile Ser Leu Gly Arg Asp Ile Gly Leu Arg Ile Pro Ala
    130                 135                 140

Leu Gln Glu Glu Ile Val Thr Leu Phe Ser Glu Leu Ile Pro Gln Thr
145                 150                 155                 160

Lys Asp Trp Ile Arg Leu Pro Gly Ala Ser Thr Gly Gln Gln Ile Ala
                165                 170                 175

Phe Arg Thr Thr Thr Arg Leu Leu Val Gly Leu Pro Leu Cys Arg Asp
            180                 185                 190

Gln Asp Tyr Lys Thr Leu Asn Asp Gln Trp Pro Asp Ser Leu Ala Lys
        195                 200                 205

Ala Ala Ile Thr Ile Ser Val Val Pro Gln Phe Leu Lys Ser Phe Val
    210                 215                 220

Ser Arg Ser Leu Pro Phe Tyr Arg Ser Val Leu Asp Arg Ala Met Asn
225                 230                 235                 240

His Val Arg Pro Leu Leu Glu Glu Arg Phe Glu Lys Gln Gly Pro Phe
                245                 250                 255

Gly Asp Asp Ala Pro Asp Lys Ser Asp Asp Leu Leu Thr Trp Leu Met
            260                 265                 270

Lys Lys Ala Pro Thr Asn Glu Lys Ser Leu Glu Ala Ile Thr Arg Arg
        275                 280                 285

Leu Met Ala Thr His Phe Val Thr Tyr Arg Pro Leu Ser Leu Ala Thr
    290                 295                 300

Thr Glu Val Leu Tyr Asp Leu Ala Ala His Pro Ser Tyr Val Pro Glu
305                 310                 315                 320

Leu Arg Glu Glu Val Glu Ala Leu Val Arg Glu His Gly Val Thr Lys
                325                 330                 335

Glu Gly Leu Asp Lys Met Tyr Lys Leu Asp Ser Phe Val Lys Glu Cys
            340                 345                 350

Leu Arg Leu His Ser Ser Pro Lys Ile Thr Met Ser Arg Lys Val Met
        355                 360                 365

Lys Asp Phe Thr Phe Ser Asp Gly Thr Thr Ile Pro Ala Gly Asn Thr
    370                 375                 380

Ile Ala Val Ala Gly Tyr Ala Ile His His Asp Glu Arg Ser Phe Pro
385                 390                 395                 400

Asn Pro Glu Glu Phe Asp Gly Phe Arg Tyr Phe Arg Lys Gln Asp Glu
                405                 410                 415

Glu Gln Glu Pro Gly Lys His Gln Leu Val Thr Leu Ala His Asp Tyr
            420                 425                 430

Val Leu Phe Gly Gly Gly Arg His Ala Cys Pro Gly Arg Phe Leu Val
        435                 440                 445

Ala Ala Ile Leu Lys Thr Met Leu Val His Val Leu Leu Thr Tyr Asp
    450                 455                 460

Val Lys Leu Glu Glu Glu Gly Val Arg Pro Pro Asp Glu Trp Pro Gly
465                 470                 475                 480

Met Leu Val Ala Val Pro Asn Gln Thr Ala Gly Val Leu Val Arg Arg
                485                 490                 495
```

```
Arg Glu Leu Ser Ser Trp Glu
            500


<210> SEQ ID NO 39
<211> LENGTH: 373
<212> TYPE: PRT
<213> ORGANISM: Omphalotus olearius

<400> SEQUENCE: 39

Met Ser Tyr Ser Arg Ile Leu Val Leu Ala Ala Val Ser Lys Cys Ile
1               5                   10                  15

Ser Thr Phe Gly Ile Val Thr Pro Pro Ser Pro His Arg Trp Met Leu
            20                  25                  30

Phe Val Pro Ile Val Val Ile Asn Ala Tyr Cys Tyr Phe Ser Thr Phe
        35                  40                  45

Thr Asp Asp Thr Met Arg Arg Asn Ala Val Ile Glu Thr Leu Val Ala
    50                  55                  60

Ser Asp Phe Leu Val Leu Thr Asp Val Gln Arg Glu Phe Arg Gln Val
65                  70                  75                  80

Gly Gln Arg Glu Pro Ile Ser Lys Leu Gly Leu Trp Ala Arg Leu Gln
                85                  90                  95

Trp Ala Leu Arg Leu Leu Leu Ser Pro Arg Gly Val Gly Trp Thr Tyr
            100                 105                 110

Glu Pro Thr Ser Ala Leu Pro Ser Arg His Asn Leu Pro Arg Arg Thr
        115                 120                 125

Phe Leu Arg Thr Gln Leu Ile Leu Leu Val Trp Ala Ile Ile Gly Asn
    130                 135                 140

Asp Leu Ala Tyr Ile Leu Thr Ser Lys Asp Pro Gly Phe Ala Lys His
145                 150                 155                 160

Ala Arg Pro Phe Ser Glu Gln Pro Leu Val Trp Arg Phe Trp Ala Thr
                165                 170                 175

Ala Val Phe Phe Phe Lys Ile Arg Lys Cys Thr Glu Val Tyr Tyr Phe
            180                 185                 190

Phe Val Ala Phe Val Leu Val Gly Val Asn Met Ser Glu Pro Ser Ser
        195                 200                 205

Trp Pro Glu Phe Phe Gly Ser Trp Ser Asp Ala Tyr Thr Val Arg Arg
    210                 215                 220

Trp Trp Gly Arg Val Trp His Gln Ser Leu Arg Arg Met Phe Ala Ser
225                 230                 235                 240

His Gly Lys Tyr Leu Ala His Arg Val Phe Gly Phe Arg Pro Gly Ser
                245                 250                 255

Pro Ala Ser Ser Tyr Thr Gln Leu Tyr Val Ala Phe Phe Leu Ser Gly
            260                 265                 270

Ile Ile His Val Thr Ser Tyr Asp Pro Arg Pro Ile Trp Tyr Phe Met
        275                 280                 285

Ser Gln Ala Val Thr Ile Thr Phe Glu Glu Ile Val Leu Thr Ile Ala
    290                 295                 300

Lys Lys Ala Gly Val Lys Ser Ser Lys Gly Thr Arg Leu Leu Gly Tyr
305                 310                 315                 320

Val Trp Val Tyr Cys Asn Leu Val Phe Thr Leu Gly Pro Leu Phe Asp
                325                 330                 335

Ser Met Asn Ala Val Gly Leu Gly Leu Gly Gly Tyr Asp Gly Thr Ile
            340                 345                 350

Leu Leu Gly Arg Tyr Arg Asp Ser Glu Trp Met Thr Gly Leu Leu Ser
```

```
        355                 360                 365

His Ala Thr Ala Asn
    370


<210> SEQ ID NO 40
<211> LENGTH: 498
<212> TYPE: PRT
<213> ORGANISM: Omphalotus olearius

<400> SEQUENCE: 40

Met Ala Asp Glu Trp Glu Glu Leu Leu Ser Trp Leu Val Ser Arg Leu
1               5                   10                  15

Gln Phe Asp Leu Tyr Val Gln Tyr Ser Ala Asn Arg Ala Leu Gly Ser
            20                  25                  30

Phe Val Leu Leu Leu Gly Ile Ala Ile Leu Val Leu Phe Thr Lys Lys
        35                  40                  45

Ile Lys Glu Ile Tyr Ile Asp Phe Leu Ala Ile Ala Tyr Gly Tyr Asp
    50                  55                  60

Leu Met Arg Ser Arg Phe Lys Tyr Gly Glu Asn Val Phe His Phe His
65                  70                  75                  80

Leu Phe Gly Asn Leu Val Ile Gly Leu Arg Gly Gln Lys Ala Arg Arg
                85                  90                  95

Val Leu Phe Glu Glu Lys Asn Phe Ser Ser Ser Asp Gly Tyr Lys Met
            100                 105                 110

Phe Ser Lys Val Val Pro Ile Pro Glu Val Thr Phe Ala Pro Glu Gln
        115                 120                 125

Glu Asp Tyr Thr Leu Ala Phe Lys Lys His Leu Gly Thr Leu Leu Gly
    130                 135                 140

Lys Asp Arg Leu Asn Asp Ile Ile Val Thr Met Phe Arg Asp Ile Glu
145                 150                 155                 160

Arg Val Met Glu Thr Trp Gly Glu Lys Gly Ala Met Asp Pro Phe Asn
                165                 170                 175

Asn Ile Asn Asp Ile Ala Phe Leu Leu Thr Val His Met Val Thr Ser
            180                 185                 190

Asp Glu Phe Val Ser Asp Leu Ser Ala Leu Ser Arg Phe Gln Ser His
        195                 200                 205

Phe Ser Arg Gln Leu Ser Ser His Thr Pro Gly Thr Ile Phe Phe Pro
    210                 215                 220

Trp Phe Tyr Arg Thr Ala Gln Arg Glu Arg Glu Lys Ser Val Met Ala
225                 230                 235                 240

Leu Phe Asn Thr Leu Thr Glu His Ile Glu Ala Arg Lys Gly Arg Thr
                245                 250                 255

Ala Pro Thr Pro Glu Ala Val Asp Leu Leu Leu Ala Arg Gly Leu Asn
            260                 265                 270

Thr Gln Glu Ile Phe Gln Phe Ile Leu Gly Phe Leu Phe Gly Gly Ala
        275                 280                 285

Phe Asn Thr Thr Lys Ala Thr Ser Trp Ile Leu Leu Tyr Leu Ala Leu
    290                 295                 300

His Pro Gln Trp Gly Ser Thr Ile Arg Ser Glu Ile Glu Thr Val Leu
305                 310                 315                 320

Ser Arg Thr Ser Ile Asp Asn Ser Glu Ser Met Cys Ser Arg Leu Ser
                325                 330                 335

Ser Ile Ser Val Glu Asp Trp Glu Ser Ser Met Pro Thr Leu Asp Leu
            340                 345                 350
```

```
Val Ile Ser Glu Thr Leu Arg Leu Val Met Asn Gln Thr Val Leu Arg
        355                 360                 365

Arg Asn Met Gly Glu Lys Leu Lys Ile Asp Gly Met Gly Glu Ile Pro
    370                 375                 380

Arg Gly Ala Phe Leu Ile Tyr Ser Asn Ala Asp Ala His Leu Asn Pro
385                 390                 395                 400

Glu Leu Tyr Pro Asp Pro Trp Thr Phe Asn Pro Gln His Phe Ser Gln
                405                 410                 415

Gly Lys Glu Asp Asp Glu Tyr Ala Phe Leu Gly Trp Gly Ala Gly Arg
            420                 425                 430

His Arg Cys Val Gly Val Lys Ile Ala Lys Leu Ala Ile Lys Ala Ile
        435                 440                 445

Val Ser Ser Phe Ile Met Thr Tyr Glu His Asp Val Ile Ser Ser Asn
    450                 455                 460

Arg Lys Val Thr Ser Lys Thr Pro Ile Pro Asp Tyr Asn Lys Ile Asn
465                 470                 475                 480

Asn Gly His Pro Lys Asn Gly Val Tyr Ser Ile Ser Tyr Ser Arg Arg
                485                 490                 495

Val Gly


<210> SEQ ID NO 41
<211> LENGTH: 387
<212> TYPE: PRT
<213> ORGANISM: Omphalotus olearius

<400> SEQUENCE: 41

Met Phe Ser Lys Val Val Pro Ile Pro Glu Val Thr Phe Ala Pro Glu
1               5                   10                  15

Gln Glu Asp Tyr Thr Leu Ala Phe Lys Lys His Leu Gly Thr Leu Leu
            20                  25                  30

Gly Lys Asp Arg Leu Asn Asp Ile Ile Val Thr Met Phe Arg Asp Ile
        35                  40                  45

Glu Arg Val Met Glu Thr Trp Gly Glu Lys Gly Ala Met Asp Pro Phe
    50                  55                  60

Asn Asn Ile Asn Asp Ile Ala Phe Leu Leu Thr Val His Met Val Thr
65                  70                  75                  80

Ser Asp Glu Phe Val Ser Asp Leu Ser Ala Leu Ser Arg Phe Gln Ser
                85                  90                  95

His Phe Ser Arg Gln Leu Ser Ser His Thr Pro Gly Thr Ile Phe Phe
            100                 105                 110

Pro Trp Phe Tyr Arg Thr Ala Gln Arg Glu Arg Glu Lys Ser Val Met
        115                 120                 125

Ala Leu Phe Asn Thr Leu Thr Glu His Ile Glu Ala Arg Lys Gly Arg
    130                 135                 140

Thr Ala Pro Thr Pro Glu Ala Val Asp Leu Leu Leu Ala Arg Gly Leu
145                 150                 155                 160

Asn Thr Gln Glu Ile Phe Gln Phe Ile Leu Gly Phe Leu Phe Gly Gly
                165                 170                 175

Ala Phe Asn Thr Thr Lys Ala Thr Ser Trp Ile Leu Leu Tyr Leu Ala
            180                 185                 190

Leu His Pro Gln Trp Gly Ser Thr Ile Arg Ser Glu Ile Glu Thr Val
        195                 200                 205

Leu Ser Arg Thr Ser Ile Asp Asn Ser Glu Ser Met Cys Ser Arg Leu
    210                 215                 220
```

Ser Ser Ile Ser Val Glu Asp Trp Glu Ser Ser Met Pro Thr Leu Asp
225 230 235 240

Leu Val Ile Ser Glu Thr Leu Arg Leu Val Met Asn Gln Thr Val Leu
245 250 255

Arg Arg Asn Met Gly Glu Lys Leu Lys Ile Asp Gly Met Gly Glu Ile
260 265 270

Pro Arg Gly Ala Phe Leu Ile Tyr Ser Asn Ala Asp Ala His Leu Asn
275 280 285

Pro Glu Leu Tyr Pro Asp Pro Trp Thr Phe Asn Pro Gln His Phe Ser
290 295 300

Gln Gly Lys Glu Asp Asp Glu Tyr Ala Phe Leu Gly Trp Gly Ala Gly
305 310 315 320

Arg His Arg Cys Val Gly Val Lys Ile Ala Lys Leu Ala Ile Lys Ala
325 330 335

Ile Val Ser Ser Phe Ile Met Thr Tyr Glu His Asp Val Ile Ser Ser
340 345 350

Asn Arg Lys Val Thr Ser Lys Thr Pro Ile Pro Asp Tyr Asn Lys Ile
355 360 365

Asn Asn Gly His Pro Lys Asn Gly Val Tyr Ser Ile Ser Tyr Ser Arg
370 375 380

Arg Val Gly
385

<210> SEQ ID NO 42
<211> LENGTH: 416
<212> TYPE: PRT
<213> ORGANISM: Omphalotus olearius

<400> SEQUENCE: 42

Met Phe Ala Leu Pro Val Asp Val His Glu Ala Ile Ile Arg Glu Leu
1 5 10 15

Phe Ala Arg Lys Asp Lys Ala Thr Val Lys Ser Leu Ser Leu Val Cys
20 25 30

Ser Ser Leu Thr His Ile Cys Gln Arg His Leu Leu Ser His Leu Thr
35 40 45

Ile Thr Cys Pro Thr Ala Gln Arg Lys Tyr Glu Arg Asp Gln Arg Ser
50 55 60

Ser His Ala Thr Gln Glu Leu Leu Gln Ser Ser Pro His Leu Ile Pro
65 70 75 80

Ile Ile Arg Ser Leu Ser Ile Ile Ala Ser Ser Thr Thr Trp Arg Gln
85 90 95

Ile Asp Val Ala Leu Leu Tyr Ile Leu Glu Thr Leu Thr Asn Leu Asn
100 105 110

Glu Phe Thr Trp Lys Ala Ser Ser Val Ser Ser His Pro Ala Arg Trp
115 120 125

Ala Glu Leu Pro His Leu Leu Gln Asp Ala Val Lys Asp Ala Ile Arg
130 135 140

Arg Pro Ser Leu Thr Ser Leu Val Leu His Phe Ala Asp Leu Thr Glu
145 150 155 160

Leu Leu Asn Ala Thr Ile Ile Val Ser Pro Ser Leu Arg Gln Leu Arg
165 170 175

Leu Gln Gly Thr Gly Tyr Ser Asn Leu Thr Leu Glu Leu Thr Arg Pro
180 185 190

Ser Ile Ile Pro Cys Asp Asp Ala Gly Glu Pro Asn Leu Gln Glu Leu
195 200 205

```
Phe Val Thr Ser Cys Lys Leu Glu Trp Ile Asp Asp Asp Glu Met Phe
    210                 215                 220

Phe Gly Trp Met Asn Thr Val Gln Pro His Leu Ser Leu Thr Arg Leu
225                 230                 235                 240

His Lys Leu Ala Val Leu Arg Cys Ile Leu Asn Ser Thr Gln Val Glu
                245                 250                 255

Leu Pro Trp Gly Pro Leu Leu Tyr His Glu Ser Val Arg Ser Lys Leu
            260                 265                 270

Glu Glu Leu Trp Phe Asp Leu Gly Ser Thr Arg Gly Pro Pro Ala Gly
        275                 280                 285

Thr Val Tyr Leu Asp Gln Leu Pro Ser Leu Arg Arg Leu Gly Leu Thr
    290                 295                 300

Ala Glu Leu Ser Gly Met Ala Ala Thr Trp Asn Leu Leu Ser Gly Ile
305                 310                 315                 320

Ala Gln Phe Phe Glu Gly Glu Asn Asn Val Glu Ile Thr His Leu Ala
                325                 330                 335

Leu Val Phe Ser Phe Ser Thr Thr Ser Leu Val Leu Asn Pro Leu Ser
            340                 345                 350

Met Pro Trp Ser Arg Leu Asp Ala Ala Val Ala Ala Leu Pro Tyr Leu
        355                 360                 365

Lys Trp Val Gly Ile Gln Val Ile Asp Cys Arg Cys Gln Pro Cys Met
    370                 375                 380

Met Ile Pro Glu Asn Ser Glu Phe Leu Leu Pro Met Leu Ala Glu Gln
385                 390                 395                 400

Gly Val Leu His Trp Ser Thr Ser Gly Leu Glu Phe Pro Ala Gln Lys
                405                 410                 415
```

<210> SEQ ID NO 43
<211> LENGTH: 1830
<212> TYPE: DNA
<213> ORGANISM: Dendrothele bispora

<400> SEQUENCE: 43

```
atgatctcgt tggacggtaa cgcttcactc actggcttca tcatgagtcc ttgcggaaag     60

tattgggctt atggcgtgtc tgaacatggt tctgattgga tgacgatata cgttcgagaa    120

acttcctctc cacatgtacc gtcacaagaa agaggcaaag atcctggaag aatggatgac    180

gaggttcgac actctcgttt cttcatcgtg tcctggaccg gtgatagcaa aggctttttc    240

tattctaaat accctcctga ggaaaatgag ggtaaaggca atgcaccggc gaagaattgc    300

atagtctatt atcatcgact cggtgagaaa caggagaatg acacccttgt ccataaggat    360

tctgggcatc cgttttggct ttggtcccta cagaccaccc ccagtggcag atatgctctc    420

ctcgctgcca gtcgtgatgc cagccacact cagctagcta agatcgctga tattcatgac    480

aacgatatcg gagccagcat gaaatggata aatcttcacg actcatggga ggctaggttt    540

agcataatcg gagacgacga ttcgaagatc tactttatga caaacctcca agctccgaat    600

tacaaagtag cgatatttga tgcttgccat ccgagtccag atgcggacct cacgaccctt    660

gtagccgaag atcccaatgc acttcttata gcggctagca ttcacgccaa ggacaaactc    720

gcgctcgttt accttcgaga tgccaggcat gaaattcacg ttcatgatct tgtcacagga    780

cgattgcttc ggcgtattct tggggatctt gttggacaat ttatggtaac ggggcgacgt    840

gcagacaatg atatgttcat cttttatagt ggtttcacct ctcccggtac agtatatcgg    900

tacaagtttg acgacgaaag agatacgtgc tcgctgttcc gtgccatacg aatccccggt    960
```

```
cttgacctag ataagtttgt gactgaatcg gtattttatc catccaaaga cgggacttcg   1020

atccatatgt tcattacccg cccaaaagac gtgttactcg atggaacggc acccgtctta   1080

caatatggtt acggcggttt cgcactagca atgctcccga cattctccgt ctctacgcta   1140

ctgttttgca agatttatcg agcgatgtat gtggtgccta atatacgtgg gggatcagag   1200

tacggtgaat catggcaccg agcaggcatg ttgggcaata agcaaaacgt atttgacgac   1260

cttaacgcag ctactgaatg gcttgttgca aataagtatg caaacaagga tcgcgttgct   1320

atacgtggag gctcaaacgg aggtgttctg acaactgcgt gtgcaaatca agcacctgga   1380

ctctatcgtt gtgtaatcac cattggaggt ataattgaca tgctcagatt tcctaaattt   1440

acgtttggcg cgctttggtg ctcagagtac ggcgaccctg aagatcctga ggctttcgat   1500

tttatctaca agtactcgcc ctatcataat attccttcgg gagagacagt catgcccgcc   1560

atgttattct ttactgctgc atacgatgac cgcgtttcgc ctttacacac attcaagcat   1620

gtcgctgctt tacaacacag ctttccccat ggtccaaatc cgatcctgat gcgcgtcgac   1680

atgaattcag ggcattacgc tggcaagagt acacagaaaa tgctggagga aacggctgac   1740

gagtacagct ttattgggaa atccatgggc ctcactatgc aagttgagaa caaatcagac   1800

tccaaccgtt ggtcttgtgt agtgaattga                                     1830
```

<210> SEQ ID NO 44
<211> LENGTH: 609
<212> TYPE: DNA
<213> ORGANISM: Dendrothele bispora

<400> SEQUENCE: 44

```
tatgtggtgc ctaatatacg tgggggatca gagtacggtg aatcatggca ccgagcaggc     60

atgttgggca ataagcaaaa cgtatttgac gaccttaacg cagctactga atggcttgtt    120

gcaaataagt atgcaaacaa ggatcgcgtt gctatacgtg gaggctcaaa cggaggtgtt    180

ctgacaactg cgtgtgcaaa tcaagcacct ggactctatc gttgtgtaat caccattgga    240

ggtataattg acatgctcag atttcctaaa tttacgtttg gcgcgctttg gtgctcagag    300

tacggcgacc ctgaagatcc tgaggctttc gattttatct acaagtactc gccctatcat    360

aatattcctt cgggagagac agtcatgccc gccatgttat tctttactgc tgcatacgat    420

gaccgcgttt cgcctttaca cacattcaag catgtcgctg ctttacaaca cagctttccc    480

catggtccaa atccgatcct gatgcgcgtc gacatgaatt cagggcatta cgctggcaag    540

agtacacaga aaatgctgga ggaaacggct gacgagtaca gctttattgg gaaatccatg    600

ggcctcact                                                            609
```

<210> SEQ ID NO 45
<211> LENGTH: 1002
<212> TYPE: DNA
<213> ORGANISM: Fomitiporia mediterranea

<400> SEQUENCE: 45

```
atgtcgacca tcgcaagatc tgcccagccc gcgcccgtgg agcaacccaa gcagtcgaat     60

ctttatccac ctatttcacc atataaagtc gattatctca aagtctccga cttgcatacc    120

ctttactacg acctgagtgg aaataaagac gggactcccg ttgtattctt gcatggtggt    180

cctggtggag gctgtgacca gcaggaccga tgctttttca atccggagaa atataagatt    240

atcctcttcg atcaacgtgg ctcgggcaag tcaactccat cagcctcgct tgaagagaac    300
```

```
acaacctggg atctcgtaaa ggacattgag aaactcagag aacatcttag tatagacaag    360

tggcatgtct ttggtggttc ctggggttca acattgtcat tggcatatgc acagagtcat    420

ccggataggg tcaaatctct cgtcttacga ggaatcttca ctcttcgtcg cagcgaactt    480

aacttcttct atcaagacgg tgcatcgcat ttattccctg aagcatggga cgaatacatc    540

gcgcccatcc cagaggcaga aagaaaagat atgatccttg cgtatcacgc acagctcaac    600

gctgctgacg aagaagtacg ccttcgtgct gcgaaggcgt ggtccaaatg ggagatgtgg    660

acatccaagc tacacgtcga ccccgagtac atcgcgcgtg caactgagga cgactgggca    720

aatgcttttg caaggattga gaaccactat ttcgtcaatg gcggattcat gcgcgacgga    780

caacttctgg agaaacaaga aatcgacaag atccggcata tacccaccat cgtcgtccaa    840

ggccgatacg acgtcgtctg tcccatcaca acggctcacg ctctgaagaa ggtcttcccc    900

gagatcgaat tacacgtcgt ccccgatgcc ggacattccg ctcgcgaacc cgggattgcg    960

aaattactcg tcgaggcagc agacaagttt gcagacttgt ag                      1002
```

```
<210> SEQ ID NO 46
<211> LENGTH: 918
<212> TYPE: DNA
<213> ORGANISM: Fomitiporia mediterranea

<400> SEQUENCE: 46

atttcaccat ataaagtcga ttatctcaaa gtctccgact tgcataccct ttactacgac     60

ctgagtggaa ataaagacgg gactcccgtt gtattcttgc atggtggtcc tggtggaggc    120

tgtgaccagc aggaccgatg ctttttcaat ccggagaaat ataagattat cctcttcgat    180

caacgtggct cgggcaagtc aactccatca gcctcgcttg aagagaacac aacctgggat    240

ctcgtaaagg acattgagaa actcagagaa catcttagta tagacaagtg gcatgtcttt    300

ggtggttcct ggggttcaac attgtcattg gcatatgcac agagtcatcc ggatagggtc    360

aaatctctcg tcttacgagg aatcttcact cttcgtcgca gcgaacttaa cttcttctat    420

caagacggtg catcgcattt attccctgaa gcatgggacg aatacatcgc gcccatccca    480

gaggcagaaa gaaaagatat gatccttgcg tatcacgcac agctcaacgc tgctgacgaa    540

gaagtacgcc ttcgtgctgc gaaggcgtgg tccaaatggg agatgtggac atccaagcta    600

cacgtcgacc ccgagtacat cgcgcgtgca actgaggacg actgggcaaa tgcttttgca    660

aggattgaga accactattt cgtcaatggc ggattcatgc gcgacggaca acttctggag    720

aaacaagaaa tcgacaagat ccggcatata cccaccatcg tcgtccaagg ccgatacgac    780

gtcgtctgtc ccatcacaac ggctcacgct ctgaagaagg tcttccccga gatcgaatta    840

cacgtcgtcc ccgatgccgg acattccgct cgcgaacccg ggattgcgaa attactcgtc    900

gaggcagcag acaagttt                                                  918
```

```
<210> SEQ ID NO 47
<211> LENGTH: 732
<212> TYPE: DNA
<213> ORGANISM: Dendrothele bispora

<400> SEQUENCE: 47

atgttttcgg ccttacatag actcaacgcc gatggtttgt ttggcagaga agtatggctc     60

gagacattga aacagagttg gaactacaag cgattcactg ccccgagacg caaaagcgat    120

gaccatatct acttcgaata caacgacggt cttcagtctc agttgtccct tcatcgcgtg    180

aaggtgggta acgaagatac catccttacc gaatctggac caggaggaga actcttttc    240
```

gattccaaca tgatctcatt ggacggtaac gcttcactca ctggtttcat catgagtcct 300
tgcggaaagt attgggctta tggcgcctct gaacatgtcc attatcatcg actcggcgag 360
aaacaggaga atgacaccct tgtccataag aattctggac atccgttttg gctttggtcc 420
ctacagacca cccccagtgg tagatatgct ctcctcgctg ccagtcgcga tgccagccac 480
actcactgtc agcttgttaa gatggccgat ctacataacg atatcggaac cagcatgaaa 540
tggataaatc ttcacgactc atgggaggcc aggttcagta taatcggaga tgacgactcg 600
aagatcttct ttatgacaaa cctgaattac aaagtggcga tatttgacgc ttgtcatccg 660
agtccaaaag ccaacctcat aactcttgta gctgaagatc ctaaaaggca acctagtgta 720
aacacgtcct ga 732

<210> SEQ ID NO 48
<211> LENGTH: 624
<212> TYPE: DNA
<213> ORGANISM: Dendrothele bispora

<400> SEQUENCE: 48
agagaagtat ggctcgagac attgaaacag agttggaact acaagcgatt cactgccccg 60
agacgcaaaa gcgatgacca tatctacttc gaatacaacg acggtcttca gtctcagttg 120
tcccttcatc gcgtgaaggt gggtaacgaa gataccatcc ttaccgaatc tggaccagga 180
ggagaactct ttttcgattc caacatgatc tcattggacg gtaacgcttc actcactggt 240
ttcatcatga gtccttgcgg aaagtattgg gcttatggcg cctctgaaca tgtccattat 300
catcgactcg gcgagaaaca ggagaatgac acccttgtcc ataagaattc tggacatccg 360
ttttggcttt ggtccctaca gaccaccccc agtggtagat atgctctcct cgctgccagt 420
cgcgatgcca gccacactca ctgtcagctt gttaagatgg ccgatctaca taacgatatc 480
ggaaccagca tgaaatggat aaatcttcac gactcatggg aggccaggtt cagtataatc 540
ggagatgacg actcgaagat cttctttatg acaaacctga attacaaagt ggcgatattt 600
gacgcttgtc atccgagtcc aaaa 624

<210> SEQ ID NO 49
<211> LENGTH: 1203
<212> TYPE: DNA
<213> ORGANISM: Fomitiporia mediterranea

<400> SEQUENCE: 49
atgattctct ctgcgtttgc ggttatcatt ctcctgccaa ttgccatcgc cagcagtggc 60
gtgcacaagc tcaaacttca taaggttcct cgaggaattg ttgactcagt tatagagtct 120
gcctacttgt cggagaagta tcgtggacag gcccaactac cgttaacggg cacagatggc 180
ccgagtcacc agcctggtcc aatcagtgat aagatagcaa atggcgggca taaagtcccg 240
ctcagtgact tcatgaatgt ccaatacttc acgaatgtca ctctcggttc tcctcctcaa 300
gagttcaggg ttattctgga tacaggtagt tcaaatctat gggtccccag caccaaatgc 360
aggtccttcg gatgttccat gcatgcgaag tataattctt ctgcatcgtc aacgtatcag 420
gagaatggga cggacatcca tatcacatat ggctctggct ccatggaagg attcgtctca 480
aaggatgttg tcaccatcgg cgacctcaaa atcgatggac aggactttgc cgaagcgacg 540
aaagatccgg gtccagcatt tgcgtttgga aagtttgacg gaatcttcgg gctcggctat 600
gatactattt ccatcaatca cattacgccc cctttctaca gcatggtcaa ccagggatta 660

-continued

```
cttggcgcac ctatcttttc tttccggttc ggttcatcgg aggatgacgg cggtgaagca    720

acctttggcg gtattgatga atcggcatac acaggggaga tcaactatgc tcctgttcgt    780

agccgggaac actgggaagt cgaacttcct aaatatgcct ttggtgataa tgagttcatt    840

cttgaaaata ctggcggcgt gatcgacact gggacctccc tcatcaattt gcctgtcgac    900

gttgcagaga agctgaatgc ccagattggt gcgaagaagt ccaggactgg gcaatacaca    960

gttgactgca agaaagtccc cgaatttccc gaattcactc tctggttcaa tgggcaggcc   1020

tatcctctca agggaagcga ctatattatc gaaagccagg gtttgtgcac cagttccttc   1080

actggtatca atatcaatgg acctggtggc gcactctgga tcattggcga tgttttcctg   1140

cgccgctact atacggtatt tgatcttgga aacgatgcta tcggttttgc gaaatcgaaa   1200

taa                                                                 1203
```

<210> SEQ ID NO 50
<211> LENGTH: 933
<212> TYPE: DNA
<213> ORGANISM: Fomitiporia mediterranea

<400> SEQUENCE: 50

```
caatacttca cgaatgtcac tctcggttct cctcctcaag agttcagggt tattctggat     60

acaggtagtt caaatctatg ggtccccagc accaaatgca ggtccttcgg atgttccatg    120

catgcgaagt ataattcttc tgcatcgtca acgtatcagg agaatgggac ggacatccat    180

atcacatatg gctctggctc catggaagga ttcgtctcaa aggatgttgt caccatcggc    240

gacctcaaaa tcgatggaca ggactttgcc gaagcgacga aagatccggg tccagcattt    300

gcgtttggaa agtttgacgg aatcttcggg ctcggctatg atactatttc catcaatcac    360

attacgcccc ctttctacag catggtcaac cagggattac ttggcgcacc tatcttttct    420

ttccggttcg gttcatcgga ggatgacggc ggtgaagcaa cctttggcgg tattgatgaa    480

tcggcataca caggggagat caactatgct cctgttcgta gccgggaaca ctgggaagtc    540

gaacttccta aatatgcctt tggtgataat gagttcattc ttgaaaatac tggcggcgtg    600

atcgacactg ggacctccct catcaatttg cctgtcgacg ttgcagagaa gctgaatgcc    660

cagattggtg cgaagaagtc caggactggg caatacacag ttgactgcaa gaaagtcccc    720

gaatttcccg aattcactct ctggttcaat gggcaggcct atcctctcaa gggaagcgac    780

tatattatcg aaagccaggg tttgtgcacc agttccttca ctggtatcaa tatcaatgga    840

cctggtggcg cactctggat cattggcgat gttttcctgc gccgctacta tacggtattt    900

gatcttggaa acgatgctat cggttttgcg aaa                                933
```

<210> SEQ ID NO 51
<211> LENGTH: 1176
<212> TYPE: DNA
<213> ORGANISM: Fomitiporia mediterranea

<400> SEQUENCE: 51

```
atgattccct ctgcatttgc gtttatcctt ctcctgccca ttgctaccgc aagcggcggc     60

gtgcacaagc tcaagctcca taagattcct cgaggaaatg ttgacccaac catagagtct    120

gcctatttgt cggagaaata tagtggacag ccccaactgc cgttaatggg cacagatggc    180

ccgagtcacc agtttggttc aatcggcgat aagatgacga atggcgggca caaagtcccg    240

ctcagtgact tcatgaatgt tcaatacttc acgaatgtca ctctcggttc tcctcctcag    300

gagttcaggg ttatcctgga tacaggtagc tcaaacctat gggtcccaag caccaaatgc    360
```

```
aggtccttcg gatgttccaa gcatgtgaag tataattctt ctgtatcgtc aacgtatcag    420

gagaatggga cggacatcca tatcaaatac ggctccggcg acatggaagg aatcgtctca    480

aaggatgttg tcaccatcgg cgacctcaaa atcgacggac aggattttgc cgaagcgacg    540

aaagatccgg gcccagcatt tgcgttcgga aagtttgacg gaatcttcgg actcggctat    600

gatactattt ccgtcaacca cattacgccc cccttctaca gcatggtcaa ccaaggatta    660

cttgatgctc ctgtttattc cttcaggttc ggttcctcgg aggatgacgg tggtgaagta    720

gtctttggcg gtattgatga atcggcatac tcaggggaga tcaactatgc tcctgttcgc    780

agccgggaac actgggaagt cgaacttcct aaatatgcct ttggggataa agagttcgtt    840

cttgaaaata ctggtggtgt gatcgacact gggacctccc tcatgtattt gcctgtcgac    900

gttgcagaga agctgaatgc ccagattggt gcgaataaca ggaatggtca atatatagtt    960

gattgcaaga aagtccctga acttcccgac ttcacccttt ggttcaatgg gcaggcctat   1020

cctctcaagg gaagtgacta tattatcgaa aaccagggca ggtcatcccg cacgtgcacc   1080

agttccttca ctggtaacga tatctatggt gacgcactat ggattattgt attcgatctt   1140

ggaaataata ctatcggttt tgcgacattg aaataa                             1176
```

<210> SEQ ID NO 52
<211> LENGTH: 933
<212> TYPE: DNA
<213> ORGANISM: Fomitiporia mediterranea

<400> SEQUENCE: 52

```
gtcccgctca gtgacttcat gaatgttcaa tacttcacga atgtcactct cggttctcct     60

cctcaggagt tcagggttat cctggataca ggtagctcaa acctatgggt cccaagcacc    120

aaatgcaggt ccttcggatg ttccaagcat gtgaagtata attcttctgt atcgtcaacg    180

tatcaggaga atgggacgga catccatatc aaatacggct ccggcgacat ggaaggaatc    240

gtctcaaagg atgttgtcac catcggcgac ctcaaaatcg acggacagga ttttgccgaa    300

gcgacgaaag atccgggccc agcatttgcg ttcggaaagt ttgacggaat cttcggactc    360

ggctatgata ctatttccgt caaccacatt acgcccccct tctacagcat ggtcaaccaa    420

ggattacttg atgctcctgt ttattccttc aggttcggtt cctcggagga tgacggtggt    480

gaagtagtct ttggcggtat tgatgaatcg gcatactcag gggagatcaa ctatgctcct    540

gttcgcagcc gggaacactg ggaagtcgaa cttcctaaat atgcctttgg ggataaagag    600

ttcgttcttg aaaatactgg tggtgtgatc gacactggga cctccctcat gtatttgcct    660

gtcgacgttg cagagaagct gaatgcccag attggtgcga ataacaggaa tggtcaatat    720

atagttgatt gcaagaaagt ccctgaactt cccgacttca ccctttggtt caatgggcag    780

gcctatcctc tcaagggaag tgactatatt atcgaaaacc agggcaggtc atcccgcacg    840

tgcaccagtt ccttcactgg taacgatatc tatggtgacg cactatggat tattgtattc    900

gatcttggaa ataatactat cggttttgcg aca                                 933
```

<210> SEQ ID NO 53
<211> LENGTH: 609
<212> TYPE: PRT
<213> ORGANISM: Dendrothele bispora

<400> SEQUENCE: 53

```
Met Ile Ser Leu Asp Gly Asn Ala Ser Leu Thr Gly Phe Ile Met Ser
1               5                   10                  15
```

-continued

```
Pro Cys Gly Lys Tyr Trp Ala Tyr Gly Val Ser Glu His Gly Ser Asp
            20                  25                  30

Trp Met Thr Ile Tyr Val Arg Glu Thr Ser Ser Pro His Val Pro Ser
        35                  40                  45

Gln Glu Arg Gly Lys Asp Pro Gly Arg Met Asp Asp Glu Val Arg His
    50                  55                  60

Ser Arg Phe Phe Ile Val Ser Trp Thr Gly Asp Ser Lys Gly Phe Phe
65                  70                  75                  80

Tyr Ser Lys Tyr Pro Pro Glu Glu Asn Glu Gly Lys Gly Asn Ala Pro
                85                  90                  95

Ala Lys Asn Cys Ile Val Tyr Tyr His Arg Leu Gly Glu Lys Gln Glu
            100                 105                 110

Asn Asp Thr Leu Val His Lys Asp Ser Gly His Pro Phe Trp Leu Trp
        115                 120                 125

Ser Leu Gln Thr Thr Pro Ser Gly Arg Tyr Ala Leu Leu Ala Ala Ser
    130                 135                 140

Arg Asp Ala Ser His Thr Gln Leu Ala Lys Ile Ala Asp Ile His Asp
145                 150                 155                 160

Asn Asp Ile Gly Ala Ser Met Lys Trp Ile Asn Leu His Asp Ser Trp
                165                 170                 175

Glu Ala Arg Phe Ser Ile Ile Gly Asp Asp Asp Ser Lys Ile Tyr Phe
            180                 185                 190

Met Thr Asn Leu Gln Ala Pro Asn Tyr Lys Val Ala Ile Phe Asp Ala
        195                 200                 205

Cys His Pro Ser Pro Asp Ala Asp Leu Thr Thr Leu Val Ala Glu Asp
    210                 215                 220

Pro Asn Ala Leu Leu Ile Ala Ala Ser Ile His Ala Lys Asp Lys Leu
225                 230                 235                 240

Ala Leu Val Tyr Leu Arg Asp Ala Arg His Glu Ile His Val His Asp
                245                 250                 255

Leu Val Thr Gly Arg Leu Leu Arg Arg Ile Leu Gly Asp Leu Val Gly
            260                 265                 270

Gln Phe Met Val Thr Gly Arg Arg Ala Asp Asn Asp Met Phe Ile Phe
        275                 280                 285

Tyr Ser Gly Phe Thr Ser Pro Gly Thr Val Tyr Arg Tyr Lys Phe Asp
    290                 295                 300

Asp Glu Arg Asp Thr Cys Ser Leu Phe Arg Ala Ile Arg Ile Pro Gly
305                 310                 315                 320

Leu Asp Leu Asp Lys Phe Val Thr Glu Ser Val Phe Tyr Pro Ser Lys
                325                 330                 335

Asp Gly Thr Ser Ile His Met Phe Ile Thr Arg Pro Lys Asp Val Leu
            340                 345                 350

Leu Asp Gly Thr Ala Pro Val Leu Gln Tyr Gly Tyr Gly Gly Phe Ala
        355                 360                 365

Leu Ala Met Leu Pro Thr Phe Ser Val Ser Thr Leu Leu Phe Cys Lys
    370                 375                 380

Ile Tyr Arg Ala Met Tyr Val Val Pro Asn Ile Arg Gly Gly Ser Glu
385                 390                 395                 400

Tyr Gly Glu Ser Trp His Arg Ala Gly Met Leu Gly Asn Lys Gln Asn
                405                 410                 415

Val Phe Asp Asp Leu Asn Ala Ala Thr Glu Trp Leu Val Ala Asn Lys
            420                 425                 430
```

-continued

```
Tyr Ala Asn Lys Asp Arg Val Ala Ile Arg Gly Gly Ser Asn Gly Gly
        435                 440                 445

Val Leu Thr Thr Ala Cys Ala Asn Gln Ala Pro Gly Leu Tyr Arg Cys
    450                 455                 460

Val Ile Thr Ile Gly Gly Ile Ile Asp Met Leu Arg Phe Pro Lys Phe
465                 470                 475                 480

Thr Phe Gly Ala Leu Trp Cys Ser Glu Tyr Gly Asp Pro Glu Asp Pro
                485                 490                 495

Glu Ala Phe Asp Phe Ile Tyr Lys Tyr Ser Pro Tyr His Asn Ile Pro
            500                 505                 510

Ser Gly Glu Thr Val Met Pro Ala Met Leu Phe Phe Thr Ala Ala Tyr
        515                 520                 525

Asp Asp Arg Val Ser Pro Leu His Thr Phe Lys His Val Ala Ala Leu
    530                 535                 540

Gln His Ser Phe Pro His Gly Pro Asn Pro Ile Leu Met Arg Val Asp
545                 550                 555                 560

Met Asn Ser Gly His Tyr Ala Gly Lys Ser Thr Gln Lys Met Leu Glu
                565                 570                 575

Glu Thr Ala Asp Glu Tyr Ser Phe Ile Gly Lys Ser Met Gly Leu Thr
            580                 585                 590

Met Gln Val Glu Asn Lys Ser Asp Ser Asn Arg Trp Ser Cys Val Val
        595                 600                 605

Asn


<210> SEQ ID NO 54
<211> LENGTH: 203
<212> TYPE: PRT
<213> ORGANISM: Dendrothele bispora

<400> SEQUENCE: 54

Tyr Val Val Pro Asn Ile Arg Gly Gly Ser Glu Tyr Gly Glu Ser Trp
1               5                   10                  15

His Arg Ala Gly Met Leu Gly Asn Lys Gln Asn Val Phe Asp Asp Leu
            20                  25                  30

Asn Ala Ala Thr Glu Trp Leu Val Ala Asn Lys Tyr Ala Asn Lys Asp
        35                  40                  45

Arg Val Ala Ile Arg Gly Gly Ser Asn Gly Gly Val Leu Thr Thr Ala
    50                  55                  60

Cys Ala Asn Gln Ala Pro Gly Leu Tyr Arg Cys Val Ile Thr Ile Gly
65                  70                  75                  80

Gly Ile Ile Asp Met Leu Arg Phe Pro Lys Phe Thr Phe Gly Ala Leu
                85                  90                  95

Trp Cys Ser Glu Tyr Gly Asp Pro Glu Asp Pro Glu Ala Phe Asp Phe
            100                 105                 110

Ile Tyr Lys Tyr Ser Pro Tyr His Asn Ile Pro Ser Gly Glu Thr Val
        115                 120                 125

Met Pro Ala Met Leu Phe Phe Thr Ala Ala Tyr Asp Asp Arg Val Ser
    130                 135                 140

Pro Leu His Thr Phe Lys His Val Ala Ala Leu Gln His Ser Phe Pro
145                 150                 155                 160

His Gly Pro Asn Pro Ile Leu Met Arg Val Asp Met Asn Ser Gly His
                165                 170                 175

Tyr Ala Gly Lys Ser Thr Gln Lys Met Leu Glu Glu Thr Ala Asp Glu
            180                 185                 190
```

```
Tyr Ser Phe Ile Gly Lys Ser Met Gly Leu Thr
        195                 200


<210> SEQ ID NO 55
<211> LENGTH: 333
<212> TYPE: PRT
<213> ORGANISM: Fomitiporia mediterranea

<400> SEQUENCE: 55

Met Ser Thr Ile Ala Arg Ser Ala Gln Pro Ala Pro Val Glu Gln Pro
1               5                   10                  15

Lys Gln Ser Asn Leu Tyr Pro Pro Ile Ser Pro Tyr Lys Val Asp Tyr
            20                  25                  30

Leu Lys Val Ser Asp Leu His Thr Leu Tyr Tyr Asp Leu Ser Gly Asn
        35                  40                  45

Lys Asp Gly Thr Pro Val Val Phe Leu His Gly Gly Pro Gly Gly Gly
    50                  55                  60

Cys Asp Gln Gln Asp Arg Cys Phe Phe Asn Pro Glu Lys Tyr Lys Ile
65                  70                  75                  80

Ile Leu Phe Asp Gln Arg Gly Ser Gly Lys Ser Thr Pro Ser Ala Ser
                85                  90                  95

Leu Glu Glu Asn Thr Thr Trp Asp Leu Val Lys Asp Ile Glu Lys Leu
            100                 105                 110

Arg Glu His Leu Ser Ile Asp Lys Trp His Val Phe Gly Gly Ser Trp
        115                 120                 125

Gly Ser Thr Leu Ser Leu Ala Tyr Ala Gln Ser His Pro Asp Arg Val
    130                 135                 140

Lys Ser Leu Val Leu Arg Gly Ile Phe Thr Leu Arg Arg Ser Glu Leu
145                 150                 155                 160

Asn Phe Phe Tyr Gln Asp Gly Ala Ser His Leu Phe Pro Glu Ala Trp
                165                 170                 175

Asp Glu Tyr Ile Ala Pro Ile Pro Glu Ala Glu Arg Lys Asp Met Ile
            180                 185                 190

Leu Ala Tyr His Ala Gln Leu Asn Ala Ala Asp Glu Glu Val Arg Leu
        195                 200                 205

Arg Ala Ala Lys Ala Trp Ser Lys Trp Glu Met Trp Thr Ser Lys Leu
    210                 215                 220

His Val Asp Pro Glu Tyr Ile Ala Arg Ala Thr Glu Asp Asp Trp Ala
225                 230                 235                 240

Asn Ala Phe Ala Arg Ile Glu Asn His Tyr Phe Val Asn Gly Gly Phe
                245                 250                 255

Met Arg Asp Gly Gln Leu Leu Glu Lys Gln Glu Ile Asp Lys Ile Arg
            260                 265                 270

His Ile Pro Thr Ile Val Val Gln Gly Arg Tyr Asp Val Val Cys Pro
        275                 280                 285

Ile Thr Thr Ala His Ala Leu Lys Lys Val Phe Pro Glu Ile Glu Leu
    290                 295                 300

His Val Val Pro Asp Ala Gly His Ser Ala Arg Glu Pro Gly Ile Ala
305                 310                 315                 320

Lys Leu Leu Val Glu Ala Ala Asp Lys Phe Ala Asp Leu
                325                 330


<210> SEQ ID NO 56
<211> LENGTH: 306
<212> TYPE: PRT
<213> ORGANISM: Fomitiporia mediterranea
```

<400> SEQUENCE: 56

Ile Ser Pro Tyr Lys Val Asp Tyr Leu Lys Val Ser Asp Leu His Thr
1 5 10 15

Leu Tyr Tyr Asp Leu Ser Gly Asn Lys Asp Gly Thr Pro Val Val Phe
20 25 30

Leu His Gly Gly Pro Gly Gly Gly Cys Asp Gln Gln Asp Arg Cys Phe
35 40 45

Phe Asn Pro Glu Lys Tyr Lys Ile Ile Leu Phe Asp Gln Arg Gly Ser
50 55 60

Gly Lys Ser Thr Pro Ser Ala Ser Leu Glu Glu Asn Thr Thr Trp Asp
65 70 75 80

Leu Val Lys Asp Ile Glu Lys Leu Arg Glu His Leu Ser Ile Asp Lys
85 90 95

Trp His Val Phe Gly Gly Ser Trp Gly Ser Thr Leu Ser Leu Ala Tyr
100 105 110

Ala Gln Ser His Pro Asp Arg Val Lys Ser Leu Val Leu Arg Gly Ile
115 120 125

Phe Thr Leu Arg Arg Ser Glu Leu Asn Phe Phe Tyr Gln Asp Gly Ala
130 135 140

Ser His Leu Phe Pro Glu Ala Trp Asp Glu Tyr Ile Ala Pro Ile Pro
145 150 155 160

Glu Ala Glu Arg Lys Asp Met Ile Leu Ala Tyr His Ala Gln Leu Asn
165 170 175

Ala Ala Asp Glu Glu Val Arg Leu Arg Ala Ala Lys Ala Trp Ser Lys
180 185 190

Trp Glu Met Trp Thr Ser Lys Leu His Val Asp Pro Glu Tyr Ile Ala
195 200 205

Arg Ala Thr Glu Asp Asp Trp Ala Asn Ala Phe Ala Arg Ile Glu Asn
210 215 220

His Tyr Phe Val Asn Gly Gly Phe Met Arg Asp Gly Gln Leu Leu Glu
225 230 235 240

Lys Gln Glu Ile Asp Lys Ile Arg His Ile Pro Thr Ile Val Val Gln
245 250 255

Gly Arg Tyr Asp Val Val Cys Pro Ile Thr Thr Ala His Ala Leu Lys
260 265 270

Lys Val Phe Pro Glu Ile Glu Leu His Val Val Pro Asp Ala Gly His
275 280 285

Ser Ala Arg Glu Pro Gly Ile Ala Lys Leu Leu Val Glu Ala Ala Asp
290 295 300

Lys Phe
305

<210> SEQ ID NO 57
<211> LENGTH: 243
<212> TYPE: PRT
<213> ORGANISM: Dendrothele bispora

<400> SEQUENCE: 57

Met Phe Ser Ala Leu His Arg Leu Asn Ala Asp Gly Leu Phe Gly Arg
1 5 10 15

Glu Val Trp Leu Glu Thr Leu Lys Gln Ser Trp Asn Tyr Lys Arg Phe
20 25 30

Thr Ala Pro Arg Arg Lys Ser Asp Asp His Ile Tyr Phe Glu Tyr Asn
35 40 45

```
Asp Gly Leu Gln Ser Gln Leu Ser Leu His Arg Val Lys Val Gly Asn
    50                  55                  60

Glu Asp Thr Ile Leu Thr Glu Ser Gly Pro Gly Gly Glu Leu Phe Phe
65                  70                  75                  80

Asp Ser Asn Met Ile Ser Leu Asp Gly Asn Ala Ser Leu Thr Gly Phe
                85                  90                  95

Ile Met Ser Pro Cys Gly Lys Tyr Trp Ala Tyr Gly Ala Ser Glu His
            100                 105                 110

Val His Tyr His Arg Leu Gly Glu Lys Gln Glu Asn Asp Thr Leu Val
        115                 120                 125

His Lys Asn Ser Gly His Pro Phe Trp Leu Trp Ser Leu Gln Thr Thr
    130                 135                 140

Pro Ser Gly Arg Tyr Ala Leu Leu Ala Ala Ser Arg Asp Ala Ser His
145                 150                 155                 160

Thr His Cys Gln Leu Val Lys Met Ala Asp Leu His Asn Asp Ile Gly
                165                 170                 175

Thr Ser Met Lys Trp Ile Asn Leu His Asp Ser Trp Glu Ala Arg Phe
            180                 185                 190

Ser Ile Ile Gly Asp Asp Asp Ser Lys Ile Phe Phe Met Thr Asn Leu
        195                 200                 205

Asn Tyr Lys Val Ala Ile Phe Asp Ala Cys His Pro Ser Pro Lys Ala
    210                 215                 220

Asn Leu Ile Thr Leu Val Ala Glu Asp Pro Lys Arg Gln Pro Ser Val
225                 230                 235                 240

Asn Thr Ser


<210> SEQ ID NO 58
<211> LENGTH: 208
<212> TYPE: PRT
<213> ORGANISM: Dendrothele bispora

<400> SEQUENCE: 58

Arg Glu Val Trp Leu Glu Thr Leu Lys Gln Ser Trp Asn Tyr Lys Arg
1               5                   10                  15

Phe Thr Ala Pro Arg Arg Lys Ser Asp Asp His Ile Tyr Phe Glu Tyr
            20                  25                  30

Asn Asp Gly Leu Gln Ser Gln Leu Ser Leu His Arg Val Lys Val Gly
        35                  40                  45

Asn Glu Asp Thr Ile Leu Thr Glu Ser Gly Pro Gly Gly Glu Leu Phe
    50                  55                  60

Phe Asp Ser Asn Met Ile Ser Leu Asp Gly Asn Ala Ser Leu Thr Gly
65                  70                  75                  80

Phe Ile Met Ser Pro Cys Gly Lys Tyr Trp Ala Tyr Gly Ala Ser Glu
                85                  90                  95

His Val His Tyr His Arg Leu Gly Glu Lys Gln Glu Asn Asp Thr Leu
            100                 105                 110

Val His Lys Asn Ser Gly His Pro Phe Trp Leu Trp Ser Leu Gln Thr
        115                 120                 125

Thr Pro Ser Gly Arg Tyr Ala Leu Leu Ala Ala Ser Arg Asp Ala Ser
    130                 135                 140

His Thr His Cys Gln Leu Val Lys Met Ala Asp Leu His Asn Asp Ile
145                 150                 155                 160

Gly Thr Ser Met Lys Trp Ile Asn Leu His Asp Ser Trp Glu Ala Arg
                165                 170                 175
```

```
Phe Ser Ile Ile Gly Asp Asp Asp Ser Lys Ile Phe Phe Met Thr Asn
            180                 185                 190

Leu Asn Tyr Lys Val Ala Ile Phe Asp Ala Cys His Pro Ser Pro Lys
        195                 200                 205


<210> SEQ ID NO 59
<211> LENGTH: 400
<212> TYPE: PRT
<213> ORGANISM: Fomitiporia mediterranea

<400> SEQUENCE: 59

Met Ile Leu Ser Ala Phe Ala Val Ile Ile Leu Leu Pro Ile Ala Ile
1               5                   10                  15

Ala Ser Ser Gly Val His Lys Leu Lys Leu His Lys Val Pro Arg Gly
            20                  25                  30

Ile Val Asp Ser Val Ile Glu Ser Ala Tyr Leu Ser Glu Lys Tyr Arg
        35                  40                  45

Gly Gln Ala Gln Leu Pro Leu Thr Gly Thr Asp Gly Pro Ser His Gln
    50                  55                  60

Pro Gly Pro Ile Ser Asp Lys Ile Ala Asn Gly Gly His Lys Val Pro
65                  70                  75                  80

Leu Ser Asp Phe Met Asn Val Gln Tyr Phe Thr Asn Val Thr Leu Gly
                85                  90                  95

Ser Pro Pro Gln Glu Phe Arg Val Ile Leu Asp Thr Gly Ser Ser Asn
            100                 105                 110

Leu Trp Val Pro Ser Thr Lys Cys Arg Ser Phe Gly Cys Ser Met His
        115                 120                 125

Ala Lys Tyr Asn Ser Ser Ala Ser Ser Thr Tyr Gln Glu Asn Gly Thr
    130                 135                 140

Asp Ile His Ile Thr Tyr Gly Ser Gly Ser Met Glu Gly Phe Val Ser
145                 150                 155                 160

Lys Asp Val Val Thr Ile Gly Asp Leu Lys Ile Asp Gly Gln Asp Phe
                165                 170                 175

Ala Glu Ala Thr Lys Asp Pro Gly Pro Ala Phe Ala Phe Gly Lys Phe
            180                 185                 190

Asp Gly Ile Phe Gly Leu Gly Tyr Asp Thr Ile Ser Ile Asn His Ile
        195                 200                 205

Thr Pro Pro Phe Tyr Ser Met Val Asn Gln Gly Leu Leu Gly Ala Pro
    210                 215                 220

Ile Phe Ser Phe Arg Phe Gly Ser Ser Glu Asp Asp Gly Gly Glu Ala
225                 230                 235                 240

Thr Phe Gly Gly Ile Asp Glu Ser Ala Tyr Thr Gly Glu Ile Asn Tyr
                245                 250                 255

Ala Pro Val Arg Ser Arg Glu His Trp Glu Val Glu Leu Pro Lys Tyr
            260                 265                 270

Ala Phe Gly Asp Asn Glu Phe Ile Leu Glu Asn Thr Gly Gly Val Ile
        275                 280                 285

Asp Thr Gly Thr Ser Leu Ile Asn Leu Pro Val Asp Val Ala Glu Lys
    290                 295                 300

Leu Asn Ala Gln Ile Gly Ala Lys Lys Ser Arg Thr Gly Gln Tyr Thr
305                 310                 315                 320

Val Asp Cys Lys Lys Val Pro Glu Phe Pro Glu Phe Thr Leu Trp Phe
                325                 330                 335

Asn Gly Gln Ala Tyr Pro Leu Lys Gly Ser Asp Tyr Ile Ile Glu Ser
```

-continued

```
            340                 345                 350

Gln Gly Leu Cys Thr Ser Ser Phe Thr Gly Ile Asn Ile Asn Gly Pro
        355                 360                 365

Gly Gly Ala Leu Trp Ile Ile Gly Asp Val Phe Leu Arg Arg Tyr Tyr
    370                 375                 380

Thr Val Phe Asp Leu Gly Asn Asp Ala Ile Gly Phe Ala Lys Ser Lys
385                 390                 395                 400


<210> SEQ ID NO 60
<211> LENGTH: 311
<212> TYPE: PRT
<213> ORGANISM: Fomitiporia mediterranea

<400> SEQUENCE: 60

Gln Tyr Phe Thr Asn Val Thr Leu Gly Ser Pro Pro Gln Glu Phe Arg
1               5                   10                  15

Val Ile Leu Asp Thr Gly Ser Ser Asn Leu Trp Val Pro Ser Thr Lys
            20                  25                  30

Cys Arg Ser Phe Gly Cys Ser Met His Ala Lys Tyr Asn Ser Ser Ala
        35                  40                  45

Ser Ser Thr Tyr Gln Glu Asn Gly Thr Asp Ile His Ile Thr Tyr Gly
    50                  55                  60

Ser Gly Ser Met Glu Gly Phe Val Ser Lys Asp Val Val Thr Ile Gly
65                  70                  75                  80

Asp Leu Lys Ile Asp Gly Gln Asp Phe Ala Glu Ala Thr Lys Asp Pro
                85                  90                  95

Gly Pro Ala Phe Ala Phe Gly Lys Phe Asp Gly Ile Phe Gly Leu Gly
            100                 105                 110

Tyr Asp Thr Ile Ser Ile Asn His Ile Thr Pro Pro Phe Tyr Ser Met
        115                 120                 125

Val Asn Gln Gly Leu Leu Gly Ala Pro Ile Phe Ser Phe Arg Phe Gly
    130                 135                 140

Ser Ser Glu Asp Asp Gly Gly Glu Ala Thr Phe Gly Gly Ile Asp Glu
145                 150                 155                 160

Ser Ala Tyr Thr Gly Glu Ile Asn Tyr Ala Pro Val Arg Ser Arg Glu
                165                 170                 175

His Trp Glu Val Glu Leu Pro Lys Tyr Ala Phe Gly Asp Asn Glu Phe
            180                 185                 190

Ile Leu Glu Asn Thr Gly Gly Val Ile Asp Thr Gly Thr Ser Leu Ile
        195                 200                 205

Asn Leu Pro Val Asp Val Ala Glu Lys Leu Asn Ala Gln Ile Gly Ala
    210                 215                 220

Lys Lys Ser Arg Thr Gly Gln Tyr Thr Val Asp Cys Lys Lys Val Pro
225                 230                 235                 240

Glu Phe Pro Glu Phe Thr Leu Trp Phe Asn Gly Gln Ala Tyr Pro Leu
                245                 250                 255

Lys Gly Ser Asp Tyr Ile Ile Glu Ser Gln Gly Leu Cys Thr Ser Ser
            260                 265                 270

Phe Thr Gly Ile Asn Ile Asn Gly Pro Gly Gly Ala Leu Trp Ile Ile
        275                 280                 285

Gly Asp Val Phe Leu Arg Arg Tyr Tyr Thr Val Phe Asp Leu Gly Asn
    290                 295                 300

Asp Ala Ile Gly Phe Ala Lys
305                 310
```

<210> SEQ ID NO 61
<211> LENGTH: 391
<212> TYPE: PRT
<213> ORGANISM: Fomitiporia mediterranea

<400> SEQUENCE: 61

Met Ile Pro Ser Ala Phe Ala Phe Ile Leu Leu Leu Pro Ile Ala Thr
1               5                   10                  15

Ala Ser Gly Gly Val His Lys Leu Lys Leu His Lys Ile Pro Arg Gly
            20                  25                  30

Asn Val Asp Pro Thr Ile Glu Ser Ala Tyr Leu Ser Glu Lys Tyr Ser
        35                  40                  45

Gly Gln Pro Gln Leu Pro Leu Met Gly Thr Asp Gly Pro Ser His Gln
    50                  55                  60

Phe Gly Ser Ile Gly Asp Lys Met Thr Asn Gly Gly His Lys Val Pro
65                  70                  75                  80

Leu Ser Asp Phe Met Asn Val Gln Tyr Phe Thr Asn Val Thr Leu Gly
                85                  90                  95

Ser Pro Pro Gln Glu Phe Arg Val Ile Leu Asp Thr Gly Ser Ser Asn
            100                 105                 110

Leu Trp Val Pro Ser Thr Lys Cys Arg Ser Phe Gly Cys Ser Lys His
        115                 120                 125

Val Lys Tyr Asn Ser Ser Val Ser Ser Thr Tyr Gln Glu Asn Gly Thr
    130                 135                 140

Asp Ile His Ile Lys Tyr Gly Ser Gly Asp Met Glu Gly Ile Val Ser
145                 150                 155                 160

Lys Asp Val Val Thr Ile Gly Asp Leu Lys Ile Asp Gly Gln Asp Phe
                165                 170                 175

Ala Glu Ala Thr Lys Asp Pro Gly Pro Ala Phe Ala Phe Gly Lys Phe
            180                 185                 190

Asp Gly Ile Phe Gly Leu Gly Tyr Asp Thr Ile Ser Val Asn His Ile
        195                 200                 205

Thr Pro Pro Phe Tyr Ser Met Val Asn Gln Gly Leu Leu Asp Ala Pro
    210                 215                 220

Val Tyr Ser Phe Arg Phe Gly Ser Ser Glu Asp Asp Gly Gly Glu Val
225                 230                 235                 240

Val Phe Gly Gly Ile Asp Glu Ser Ala Tyr Ser Gly Glu Ile Asn Tyr
                245                 250                 255

Ala Pro Val Arg Ser Arg Glu His Trp Glu Val Glu Leu Pro Lys Tyr
            260                 265                 270

Ala Phe Gly Asp Lys Glu Phe Val Leu Glu Asn Thr Gly Gly Val Ile
        275                 280                 285

Asp Thr Gly Thr Ser Leu Met Tyr Leu Pro Val Asp Val Ala Glu Lys
    290                 295                 300

Leu Asn Ala Gln Ile Gly Ala Asn Asn Arg Asn Gly Gln Tyr Ile Val
305                 310                 315                 320

Asp Cys Lys Lys Val Pro Glu Leu Pro Asp Phe Thr Leu Trp Phe Asn
                325                 330                 335

Gly Gln Ala Tyr Pro Leu Lys Gly Ser Asp Tyr Ile Ile Glu Asn Gln
            340                 345                 350

Gly Arg Ser Ser Arg Thr Cys Thr Ser Ser Phe Thr Gly Asn Asp Ile
        355                 360                 365

Tyr Gly Asp Ala Leu Trp Ile Ile Val Phe Asp Leu Gly Asn Asn Thr
    370                 375                 380

Ile Gly Phe Ala Thr Leu Lys
385 390

<210> SEQ ID NO 62
<211> LENGTH: 311
<212> TYPE: PRT
<213> ORGANISM: Fomitiporia mediterranea

<400> SEQUENCE: 62

Val Pro Leu Ser Asp Phe Met Asn Val Gln Tyr Phe Thr Asn Val Thr
1 5 10 15

Leu Gly Ser Pro Pro Gln Glu Phe Arg Val Ile Leu Asp Thr Gly Ser
20 25 30

Ser Asn Leu Trp Val Pro Ser Thr Lys Cys Arg Ser Phe Gly Cys Ser
35 40 45

Lys His Val Lys Tyr Asn Ser Ser Val Ser Ser Thr Tyr Gln Glu Asn
50 55 60

Gly Thr Asp Ile His Ile Lys Tyr Gly Ser Gly Asp Met Glu Gly Ile
65 70 75 80

Val Ser Lys Asp Val Val Thr Ile Gly Asp Leu Lys Ile Asp Gly Gln
85 90 95

Asp Phe Ala Glu Ala Thr Lys Asp Pro Gly Pro Ala Phe Ala Phe Gly
100 105 110

Lys Phe Asp Gly Ile Phe Gly Leu Gly Tyr Asp Thr Ile Ser Val Asn
115 120 125

His Ile Thr Pro Pro Phe Tyr Ser Met Val Asn Gln Gly Leu Leu Asp
130 135 140

Ala Pro Val Tyr Ser Phe Arg Phe Gly Ser Ser Glu Asp Asp Gly Gly
145 150 155 160

Glu Val Val Phe Gly Gly Ile Asp Glu Ser Ala Tyr Ser Gly Glu Ile
165 170 175

Asn Tyr Ala Pro Val Arg Ser Arg Glu His Trp Glu Val Glu Leu Pro
180 185 190

Lys Tyr Ala Phe Gly Asp Lys Glu Phe Val Leu Glu Asn Thr Gly Gly
195 200 205

Val Ile Asp Thr Gly Thr Ser Leu Met Tyr Leu Pro Val Asp Val Ala
210 215 220

Glu Lys Leu Asn Ala Gln Ile Gly Ala Asn Asn Arg Asn Gly Gln Tyr
225 230 235 240

Ile Val Asp Cys Lys Lys Val Pro Glu Leu Pro Asp Phe Thr Leu Trp
245 250 255

Phe Asn Gly Gln Ala Tyr Pro Leu Lys Gly Ser Asp Tyr Ile Ile Glu
260 265 270

Asn Gln Gly Arg Ser Ser Arg Thr Cys Thr Ser Ser Phe Thr Gly Asn
275 280 285

Asp Ile Tyr Gly Asp Ala Leu Trp Ile Ile Val Phe Asp Leu Gly Asn
290 295 300

Asn Thr Ile Gly Phe Ala Thr
305 310

<210> SEQ ID NO 63
<211> LENGTH: 12
<212> TYPE: PRT
<213> ORGANISM: Artificial Sequence
<220> FEATURE:
<223> OTHER INFORMATION: OMP

<400> SEQUENCE: 63

Trp Val Ile Val Val Gly Val Ile Gly Val Ile Gly
1 5 10

<210> SEQ ID NO 64
<211> LENGTH: 20
<212> TYPE: DNA
<213> ORGANISM: Artificial Sequence
<220> FEATURE:
<223> OTHER INFORMATION: Forward Primer 1 Example 1

<400> SEQUENCE: 64
atggagactt ccactcagac 20

<210> SEQ ID NO 65
<211> LENGTH: 20
<212> TYPE: DNA
<213> ORGANISM: Artificial Sequence
<220> FEATURE:
<223> OTHER INFORMATION: Reverse Primer 1 Example 1

<400> SEQUENCE: 65
ttattccgtg ctcatgactg 20

<210> SEQ ID NO 66
<211> LENGTH: 29
<212> TYPE: DNA
<213> ORGANISM: Artificial Sequence
<220> FEATURE:
<223> OTHER INFORMATION: Forward Primer 2 Example 1

<400> SEQUENCE: 66
ggggggcata tggagacttc cactcagac 29

<210> SEQ ID NO 67
<211> LENGTH: 66
<212> TYPE: DNA
<213> ORGANISM: Artificial Sequence
<220> FEATURE:
<223> OTHER INFORMATION: Forward Primer 3 Example 1

<400> SEQUENCE: 67 tttttcata tggagcatca tcatcatcat catcatcata cttccactca gaccaaagct 60
ggctca 66

<210> SEQ ID NO 68
<211> LENGTH: 33
<212> TYPE: DNA
<213> ORGANISM: Artificial Sequence
<220> FEATURE:
<223> OTHER INFORMATION: Reverse Primer 2 Example 1

<400> SEQUENCE: 68
ccccccgcgg ccgcttattc cgtgctcatg act 33

<210> SEQ ID NO 69
<211> LENGTH: 31
<212> TYPE: DNA
<213> ORGANISM: Artificial Sequence
<220> FEATURE:
<223> OTHER INFORMATION: Forward Primer 1 Example 2

<400> SEQUENCE: 69
catgagacct agtcatgagc acggaataag c 31

<210> SEQ ID NO 70
<211> LENGTH: 31
<212> TYPE: DNA
<213> ORGANISM: Artificial Sequence
<220> FEATURE:
<223> OTHER INFORMATION: Reverse Primer 1 Example 2

<400> SEQUENCE: 70
ggccgcttat tccgtgctca tgactaggtc t 31

<210> SEQ ID NO 71
<211> LENGTH: 75
<212> TYPE: DNA
<213> ORGANISM: Artificial Sequence
<220> FEATURE:
<223> OTHER INFORMATION: Forward Primer 2 Example 2

<400> SEQUENCE: 71
aggtctcacc cactggtgct ggctgcactg ctcgtcatcg ttggttcagt catgagcacg 60
gaataagcgg ccgca 75

<210> SEQ ID NO 72
<211> LENGTH: 75
<212> TYPE: DNA
<213> ORGANISM: Artificial Sequence
<220> FEATURE:
<223> OTHER INFORMATION: Reverse primer 2 Example 2

<400> SEQUENCE: 72
tgcggccgct tattccgtgc tcatgactga accaacgatg acgagcagtg cagccagcac 60
cagtgggtga gacct 75

<210> SEQ ID NO 73
<211> LENGTH: 57
<212> TYPE: DNA
<213> ORGANISM: Artificial Sequence
<220> FEATURE:
<223> OTHER INFORMATION: Forward primer 3 Example 2

<400> SEQUENCE: 73
aggtctcacc cagcaacgac cgtagtagtt gttgttattg tgggttaagc ggccgca 57

<210> SEQ ID NO 74
<211> LENGTH: 57
<212> TYPE: DNA
<213> ORGANISM: Artificial Sequence
<220> FEATURE:
<223> OTHER INFORMATION: Reverse primer 3 Example 2

<400> SEQUENCE: 74
tgcggccgct taacccacaa taacaacaac tactacggtc gttgctgggt gagacct 57

<210> SEQ ID NO 75
<211> LENGTH: 66
<212> TYPE: DNA
<213> ORGANISM: Artificial Sequence
<220> FEATURE:
<223> OTHER INFORMATION: Forward primer 4 Example 2

<400> SEQUENCE: 75
aggtctcacc cacagttcat tgccgttgta gttgtggcag tcgtgtgctg tttctaagcg 60
gccgca 66

<210> SEQ ID NO 76
<211> LENGTH: 66
<212> TYPE: DNA
<213> ORGANISM: Artificial Sequence
<220> FEATURE:
<223> OTHER INFORMATION: Reverse primer 4 Example 2

<400> SEQUENCE: 76
tgcggccgct tagaaacagc acacgactgc cacaactaca acggcaatga actgtgggtg 60
agacct 66

<210> SEQ ID NO 77
<211> LENGTH: 60
<212> TYPE: DNA
<213> ORGANISM: Artificial Sequence
<220> FEATURE:
<223> OTHER INFORMATION: Forward primer 5 Example 2

<400> SEQUENCE: 77
aggtctcacc catgggtcat cgtcgttggt gttatcggtg tcatcggata agcggccgca 60

<210> SEQ ID NO 78
<211> LENGTH: 60
<212> TYPE: DNA
<213> ORGANISM: Artificial Sequence
<220> FEATURE:
<223> OTHER INFORMATION: Reverse primer 5 Example 2

<400> SEQUENCE: 78
tgcggccgct tatccgatga caccgataac accaacgacg atgacccatg ggtgagacct 60

<210> SEQ ID NO 79
<211> LENGTH: 244
<212> TYPE: DNA
<213> ORGANISM: Artificial Sequence
<220> FEATURE:
<223> OTHER INFORMATION: OMP TEV, Example 3

<400> SEQUENCE: 79
ggatcccaag gcactcgccg actacaaagc tgatcaccgc gcctttgctc aatctgtccc 60
cgacttgacg cctcaggagc gtgcggcttt ggagctcggt gattcgtggg ctattcgttg 120
cgcgatgaag aatatgccct cgtcgctctt ggacgctgct cgtgaatccg gcgaaaactt 180
gtacttccaa ggtttcccat gggtcatcgt cgttggtgtt atcggtgtca tcggataaga 240
attc 244

<210> SEQ ID NO 80
<211> LENGTH: 270
<212> TYPE: DNA
<213> ORGANISM: Artificial Sequence
<220> FEATURE:
<223> OTHER INFORMATION: OMP R1, Example 3

<400> SEQUENCE: 80
ggatcccaag gcactcgccg actacaaagc tgatcaccgc gcctttgctc aatctgtccc 60
cgacttgacg cctcaggagc gtgcggcttt ggagctcggt gattcgtggg ctattcgttg 120
cgcgatgaag aatatgccct cgtcgctctt ggacgctgct cgtgaatccg gcgaagaggc 180
atcccaaaac ggtttcccag tctttgcaga atttctgcct ctgttcagca aattcggttc 240
gcggatgcac attctgaaat aagcggccgc 270

<210> SEQ ID NO 81
<211> LENGTH: 419
<212> TYPE: PRT
<213> ORGANISM: Artificial Sequence
<220> FEATURE:
<223> OTHER INFORMATION: OMP TEV, complete

<400> SEQUENCE: 81

```
Met Glu His His His His His His His His Thr Ser Thr Gln Thr Lys
1               5                   10                  15

Ala Gly Ser Leu Thr Ile Val Gly Thr Gly Ile Glu Ser Ile Gly Gln
            20                  25                  30

Met Thr Leu Gln Ala Leu Ser Tyr Ile Glu Ala Ala Ala Lys Val Phe
        35                  40                  45

Tyr Cys Val Ile Asp Pro Ala Thr Glu Ala Phe Ile Leu Thr Lys Asn
    50                  55                  60

Lys Asn Cys Val Asp Leu Tyr Gln Tyr Tyr Asp Asn Gly Lys Ser Arg
65                  70                  75                  80

Leu Asn Thr Tyr Thr Gln Met Ser Glu Leu Met Val Arg Glu Val Arg
                85                  90                  95

Lys Gly Leu Asp Val Val Gly Val Phe Tyr Gly His Pro Gly Val Phe
            100                 105                 110

Val Asn Pro Ser His Arg Ala Leu Ala Ile Ala Lys Ser Glu Gly Tyr
        115                 120                 125

Arg Ala Arg Met Leu Pro Gly Val Ser Ala Glu Asp Cys Leu Phe Ala
    130                 135                 140

Asp Leu Cys Ile Asp Pro Ser Asn Pro Gly Cys Leu Thr Tyr Glu Ala
145                 150                 155                 160

Ser Asp Phe Leu Ile Arg Asp Arg Pro Val Ser Ile His Ser His Leu
                165                 170                 175

Val Leu Phe Gln Val Gly Cys Val Gly Ile Ala Asp Phe Asn Phe Thr
            180                 185                 190

Gly Phe Asp Asn Asn Lys Phe Gly Val Leu Val Asp Arg Leu Glu Gln
        195                 200                 205

Glu Tyr Gly Ala Glu His Pro Val Val His Tyr Ile Ala Ala Met Met
    210                 215                 220

Pro His Gln Asp Pro Val Thr Asp Lys Tyr Thr Val Ala Gln Leu Arg
225                 230                 235                 240

Glu Pro Glu Ile Ala Lys Arg Val Gly Gly Val Ser Thr Phe Tyr Ile
                245                 250                 255

Pro Pro Lys Ala Arg Lys Ala Ser Asn Leu Asp Ile Ile Arg Arg Leu
            260                 265                 270

Glu Leu Leu Pro Ala Gly Gln Val Pro Asp Lys Lys Ala Arg Ile Tyr
        275                 280                 285

Pro Ala Asn Gln Trp Glu Pro Asp Val Pro Glu Val Glu Pro Tyr Arg
    290                 295                 300

Pro Ser Asp Gln Ala Ala Ile Ala Gln Leu Ala Asp His Ala Pro Pro
305                 310                 315                 320

Glu Gln Tyr Gln Pro Leu Ala Thr Ser Lys Ala Met Ser Asp Val Met
                325                 330                 335

Thr Lys Leu Ala Leu Asp Pro Lys Ala Leu Ala Asp Tyr Lys Ala Asp
            340                 345                 350

His Arg Ala Phe Ala Gln Ser Val Pro Asp Leu Thr Pro Gln Glu Arg
        355                 360                 365

Ala Ala Leu Glu Leu Gly Asp Ser Trp Ala Ile Arg Cys Ala Met Lys
```

370 375 380

Asn Met Pro Ser Ser Leu Leu Asp Ala Ala Arg Glu Ser Gly Glu Asn
385 390 395 400

Leu Tyr Phe Gln Gly Phe Pro Trp Val Ile Val Val Gly Val Ile Gly
405 410 415

Val Ile Gly

<210> SEQ ID NO 82
<211> LENGTH: 1260
<212> TYPE: DNA
<213> ORGANISM: Artificial Sequence
<220> FEATURE:
<223> OTHER INFORMATION: OMP TEV, complete

<400> SEQUENCE: 82
atggagcatc atcatcatca tcatcatcat acttccactc agaccaaagc tggctcactc 60
accatcgtcg gtaccggtat cgagagtatc ggacaaatga cgcttcaggc gttgtcctac 120
atcgaagccg ccgcgaaggt tttctactgc gtcatcgacc ccgccactga ggcattcatc 180
ctcaccaaga acaagaactg cgttgacttg tatcagtatt acgacaatgg caagtccaga 240
ttgaacactt acacccaaat gtcagagctc atggtcaggg aagtccgcaa gggcctcgat 300
gtcgtgggcg tcttctacgg ccacccagga gtgttcgtga acccgtctca ccgagctctg 360
gctatcgcca agagtgaagg ctaccgagcg aggatgcttc caggcgtgtc tgcggaagat 420
tgtctcttcg cggacttgtg cattgatcct tcgaacccgg gttgcctgac ctacgaggca 480
tcggatttcc tgatcaggga tcgcccggtc agcatccaca gtcacttggt cctgttccaa 540
gtcggatgcg tcggtatcgc cgacttcaac ttcactggat tcgacaacaa caaattcggc 600
gttctcgtcg accgtctcga gcaagaatac ggcgccgagc accctgtcgt ccattacatc 660
gcagctatga tgccacacca agacccagtc accgataaat acaccgtcgc gcagctccgt 720
gagcccgaga tcgcgaagcg tgttggcggt gtctcgactt tctacatccc tcccaaggcc 780
aggaaagcat cgaacttgga catcataagg cgcctagagc tcttgcctgc tgggcaagtt 840
cccgacaaga aagcgcgtat ttacccggcc aaccagtggg agcccgatgt tcccgaagtc 900
gaaccctaca gaccatctga ccaggctgcc atcgctcagt tggctgacca cgctcctcct 960
gagcaatatc aacctcttgc tacttcgaaa gccatgtctg atgttatgac gaagttggct 1020
ttggatccca aggcactcgc cgactacaaa gctgatcacc gcgcctttgc tcaatctgtc 1080
cccgacttga cgcctcagga gcgtgcggct ttggagctcg gtgattcgtg ggctattcgt 1140
tgcgcgatga agaatatgcc ctcgtcgctc ttggacgctg ctcgtgaatc cggcgaaaac 1200
ttgtacttcc aaggtttccc atgggtcatc gtcgttggtg ttatcggtgt catcggataa 1260

<210> SEQ ID NO 83
<211> LENGTH: 25
<212> TYPE: PRT
<213> ORGANISM: Artificial Sequence
<220> FEATURE:
<223> OTHER INFORMATION: OMP Fmoc SPPS of omphalotin with follower, linker
<220> FEATURE:
<221> NAME/KEY: MOD_RES
<222> LOCATION: (19)..(19)
<223> OTHER INFORMATION: Xaa is 4-hydroxymethyl-benzoic acid

<400> SEQUENCE: 83

Trp Val Ile Val Val Gly Val Ile Gly Val Ile Gly Ser Val Met Ser
1 5 10 15

```
Thr Glu Xaa Arg Arg Arg Arg Arg Arg
            20                  25


<210> SEQ ID NO 84
<211> LENGTH: 19
<212> TYPE: PRT
<213> ORGANISM: Artificial Sequence
<220> FEATURE:
<223> OTHER INFORMATION: OMP Fmoc SPPS of omphalotin without follower,
      linker
<220> FEATURE:
<221> NAME/KEY: MOD_RES
<222> LOCATION: (13)..(13)
<223> OTHER INFORMATION: Xaa is 4-hydroxymethyl-benzoic acid

<400> SEQUENCE: 84

Trp Val Ile Val Val Gly Val Ile Gly Val Ile Gly Xaa Arg Arg Arg
1               5                   10                  15

Arg Arg Arg


<210> SEQ ID NO 85
<211> LENGTH: 18
<212> TYPE: PRT
<213> ORGANISM: Omphalotus olearius

<400> SEQUENCE: 85

Trp Val Ile Val Val Gly Val Val Gly Val Ile Gly Ser Val Met Ser
1               5                   10                  15

Thr Glu


<210> SEQ ID NO 86
<211> LENGTH: 12
<212> TYPE: PRT
<213> ORGANISM: Omphalotus olearius

<400> SEQUENCE: 86

Trp Val Ile Val Val Gly Val Ile Gly Val Ile Gly
1               5                   10


<210> SEQ ID NO 87
<211> LENGTH: 437
<212> TYPE: PRT
<213> ORGANISM: Artificial Sequence
<220> FEATURE:
<223> OTHER INFORMATION: OMP 2xOMP, complete

<400> SEQUENCE: 87

Met Glu His His His His His His His His Thr Ser Thr Gln Thr Lys
1               5                   10                  15

Ala Gly Ser Leu Thr Ile Val Gly Thr Gly Ile Glu Ser Ile Gly Gln
            20                  25                  30

Met Thr Leu Gln Ala Leu Ser Tyr Ile Glu Ala Ala Ala Lys Val Phe
        35                  40                  45

Tyr Cys Val Ile Asp Pro Ala Thr Glu Ala Phe Ile Leu Thr Lys Asn
    50                  55                  60

Lys Asn Cys Val Asp Leu Tyr Gln Tyr Tyr Asp Asn Gly Lys Ser Arg
65                  70                  75                  80

Leu Asn Thr Tyr Thr Gln Met Ser Glu Leu Met Val Arg Glu Val Arg
                85                  90                  95

Lys Gly Leu Asp Val Val Gly Val Phe Tyr Gly His Pro Gly Val Phe
            100                 105                 110
```

```
Val Asn Pro Ser His Arg Ala Leu Ala Ile Ala Lys Ser Glu Gly Tyr
        115                 120                 125

Arg Ala Arg Met Leu Pro Gly Val Ser Ala Glu Asp Cys Leu Phe Ala
    130                 135                 140

Asp Leu Cys Ile Asp Pro Ser Asn Pro Gly Cys Leu Thr Tyr Glu Ala
145                 150                 155                 160

Ser Asp Phe Leu Ile Arg Asp Arg Pro Val Ser Ile His Ser His Leu
                165                 170                 175

Val Leu Phe Gln Val Gly Cys Val Gly Ile Ala Asp Phe Asn Phe Thr
            180                 185                 190

Gly Phe Asp Asn Asn Lys Phe Gly Val Leu Val Asp Arg Leu Glu Gln
        195                 200                 205

Glu Tyr Gly Ala Glu His Pro Val Val His Tyr Ile Ala Ala Met Met
    210                 215                 220

Pro His Gln Asp Pro Val Thr Asp Lys Tyr Thr Val Ala Gln Leu Arg
225                 230                 235                 240

Glu Pro Glu Ile Ala Lys Arg Val Gly Gly Val Ser Thr Phe Tyr Ile
                245                 250                 255

Pro Pro Lys Ala Arg Lys Ala Ser Asn Leu Asp Ile Ile Arg Arg Leu
            260                 265                 270

Glu Leu Leu Pro Ala Gly Gln Val Pro Asp Lys Lys Ala Arg Ile Tyr
        275                 280                 285

Pro Ala Asn Gln Trp Glu Pro Asp Val Pro Glu Val Glu Pro Tyr Arg
    290                 295                 300

Pro Ser Asp Gln Ala Ala Ile Ala Gln Leu Ala Asp His Ala Pro Pro
305                 310                 315                 320

Glu Gln Tyr Gln Pro Leu Ala Thr Ser Lys Ala Met Ser Asp Val Met
                325                 330                 335

Thr Lys Leu Ala Leu Asp Pro Lys Ala Leu Ala Asp Tyr Lys Ala Asp
            340                 345                 350

His Arg Ala Phe Ala Gln Ser Val Pro Asp Leu Thr Pro Gln Glu Arg
        355                 360                 365

Ala Ala Leu Glu Leu Gly Asp Ser Trp Ala Ile Arg Cys Ala Met Lys
    370                 375                 380

Asn Met Pro Ser Ser Leu Leu Asp Ala Ala Arg Glu Ser Gly Glu Glu
385                 390                 395                 400

Ala Ser Gln Asn Gly Phe Pro Trp Val Ile Val Val Gly Val Ile Gly
                405                 410                 415

Val Ile Gly Trp Val Ile Val Val Gly Val Ile Gly Val Ile Gly Ser
            420                 425                 430

Val Met Ser Thr Glu
        435
```

<210> SEQ ID NO 88
<211> LENGTH: 1314
<212> TYPE: DNA
<213> ORGANISM: Artificial Sequence
<220> FEATURE:
<223> OTHER INFORMATION: OMP 2xOMP, complete

<400> SEQUENCE: 88

```
atggagcatc atcatcatca tcatcatcat acttccactc agaccaaagc tggctcactc      60

accatcgtcg gtaccggtat cgagagtatc ggacaaatga cgcttcaggc gttgtcctac     120

atcgaagccg ccgcgaaggt tttctactgc gtcatcgacc ccgccactga ggcattcatc     180
```

```
ctcaccaaga acaagaactg cgttgacttg tatcagtatt acgacaatgg caagtccaga    240

ttgaacactt acacccaaat gtcagagctc atggtcaggg aagtccgcaa gggcctcgat    300

gtcgtgggcg tcttctacgg ccacccagga gtgttcgtga acccgtctca ccgagctctg    360

gctatcgcca agagtgaagg ctaccgagcg aggatgcttc caggcgtgtc tgcggaagat    420

tgtctcttcg cggacttgtg cattgatcct tcgaacccgg gttgcctgac ctacgaggca    480

tcggatttcc tgatcaggga tcgcccggtc agcatccaca gtcacttggt cctgttccaa    540

gtcggatgcg tcggtatcgc cgacttcaac ttcactggat tcgacaacaa caaattcggc    600

gttctcgtcg accgtctcga gcaagaatac ggcgccgagc accctgtcgt ccattacatc    660

gcagctatga tgccacacca agacccagtc accgataaat acaccgtcgc gcagctccgt    720

gagcccgaga tcgcgaagcg tgttggcggt gtctcgactt tctacatccc tcccaaggcc    780

aggaaagcat cgaacttgga catcataagg cgcctagagc tcttgcctgc tgggcaagtt    840

cccgacaaga aagcgcgtat ttacccggcc aaccagtggg agcccgatgt tcccgaagtc    900

gaaccctaca gaccatctga ccaggctgcc atcgctcagt tggctgacca cgctcctcct    960

gagcaatatc aacctcttgc tacttcgaaa gccatgtctg atgttatgac gaagttggct   1020

ttggatccca aggcactcgc cgactacaaa gctgatcacc gcgcctttgc tcaatctgtc   1080

cccgacttga cgcctcagga gcgtgcggct ttggagctcg gtgattcgtg ggctattcgt   1140

tgcgcgatga agaatatgcc ctcgtcgctc ttggacgctg ctcgtgaatc cggcgaagag   1200

gcatcccaaa acggtttccc atgggtcatc gtcgttggtg ttatcggtgt catcggatgg   1260

gtcatcgtcg ttggtgttat cggtgtcatc ggatcagtca tgagcacgga ataa         1314
```

```
<210> SEQ ID NO 89
<211> LENGTH: 425
<212> TYPE: PRT
<213> ORGANISM: Artificial Sequence
<220> FEATURE:
<223> OTHER INFORMATION: OMP PtoA, complete

<400> SEQUENCE: 89

Met Glu His His His His His His His His Thr Ser Thr Gln Thr Lys
1               5                   10                  15

Ala Gly Ser Leu Thr Ile Val Gly Thr Gly Ile Glu Ser Ile Gly Gln
            20                  25                  30

Met Thr Leu Gln Ala Leu Ser Tyr Ile Glu Ala Ala Ala Lys Val Phe
        35                  40                  45

Tyr Cys Val Ile Asp Pro Ala Thr Glu Ala Phe Ile Leu Thr Lys Asn
    50                  55                  60

Lys Asn Cys Val Asp Leu Tyr Gln Tyr Tyr Asp Asn Gly Lys Ser Arg
65                  70                  75                  80

Leu Asn Thr Tyr Thr Gln Met Ser Glu Leu Met Val Arg Glu Val Arg
                85                  90                  95

Lys Gly Leu Asp Val Val Gly Val Phe Tyr Gly His Pro Gly Val Phe
            100                 105                 110

Val Asn Pro Ser His Arg Ala Leu Ala Ile Ala Lys Ser Glu Gly Tyr
        115                 120                 125

Arg Ala Arg Met Leu Pro Gly Val Ser Ala Glu Asp Cys Leu Phe Ala
    130                 135                 140

Asp Leu Cys Ile Asp Pro Ser Asn Pro Gly Cys Leu Thr Tyr Glu Ala
145                 150                 155                 160

Ser Asp Phe Leu Ile Arg Asp Arg Pro Val Ser Ile His Ser His Leu
```

-continued 165 170 175

Val Leu Phe Gln Val Gly Cys Val Gly Ile Ala Asp Phe Asn Phe Thr
180 185 190

Gly Phe Asp Asn Asn Lys Phe Gly Val Leu Val Asp Arg Leu Glu Gln
195 200 205

Glu Tyr Gly Ala Glu His Pro Val Val His Tyr Ile Ala Ala Met Met
210 215 220

Pro His Gln Asp Pro Val Thr Asp Lys Tyr Thr Val Ala Gln Leu Arg
225 230 235 240

Glu Pro Glu Ile Ala Lys Arg Val Gly Gly Val Ser Thr Phe Tyr Ile
245 250 255

Pro Pro Lys Ala Arg Lys Ala Ser Asn Leu Asp Ile Ile Arg Arg Leu
260 265 270

Glu Leu Leu Pro Ala Gly Gln Val Pro Asp Lys Lys Ala Arg Ile Tyr
275 280 285

Pro Ala Asn Gln Trp Glu Pro Asp Val Pro Glu Val Glu Pro Tyr Arg
290 295 300

Pro Ser Asp Gln Ala Ala Ile Ala Gln Leu Ala Asp His Ala Pro Pro
305 310 315 320

Glu Gln Tyr Gln Pro Leu Ala Thr Ser Lys Ala Met Ser Asp Val Met
325 330 335

Thr Lys Leu Ala Leu Asp Pro Lys Ala Leu Ala Asp Tyr Lys Ala Asp
340 345 350

His Arg Ala Phe Ala Gln Ser Val Pro Asp Leu Thr Pro Gln Glu Arg
355 360 365

Ala Ala Leu Glu Leu Gly Asp Ser Trp Ala Ile Arg Cys Ala Met Lys
370 375 380

Asn Met Pro Ser Ser Leu Leu Asp Ala Ala Arg Glu Ser Gly Glu Glu
385 390 395 400

Ala Ser Gln Asn Gly Phe Ala Trp Val Ile Val Val Gly Val Ile Gly
405 410 415

Val Ile Gly Ser Val Met Ser Thr Glu
420 425

<210> SEQ ID NO 90
<211> LENGTH: 1254
<212> TYPE: DNA
<213> ORGANISM: Artificial Sequence
<220> FEATURE:
<223> OTHER INFORMATION: OMP PtoA, complete

<400> SEQUENCE: 90
atggagactt ccactcagac caaagctggc tcactcacca tcgtcggtac cggtatcgag 60
agtatcggac aaatgacgct tcaggcgttg tcctacatcg aagccgccgc gaaggttttc 120
tactgcgtca tcgaccccgc cactgaggca ttcatcctca ccaagaacaa gaactgcgtt 180
gacttgtatc agtattacga caatggcaag tccagattga acacttacac ccaaatgtca 240
gagctcatgg tcagggaagt ccgcaagggc ctcgatgtcg tgggcgtctt ctacggccac 300
ccaggagtgt tcgtgaaccc gtctcaccga gctctggcta tcgccaagag tgaaggctac 360
cgagcgagga tgcttccagg cgtgtctgcg gaagattgtc tcttcgcgga cttgtgcatt 420
gatccttcga acccgggttg cctgacctac gaggcatcgg atttcctgat cagggatcgc 480
ccggtcagca tccacagtca cttggtcctg ttccaagtcg gatgcgtcgg tatcgccgac 540
ttcaacttca ctggattcga caacaacaaa ttcggcgttc tcgtcgaccg tctcgagcaa 600
gaatacggcg ccgagcaccc tgtcgtccat tacatcgcag ctatgatgcc acaccaagac 660
ccagtcaccg ataaatacac cgtcgcgcag ctccgtgagc ccgagatcgc gaagcgtgtt 720
ggcggtgtct cgactttcta catccctccc aaggccagga aagcatcgaa cttggacatc 780
ataaggcgcc tagagctctt gcctgctggg caagttcccg acaagaaagc gcgtatttac 840
ccggccaacc agtgggagcc cgatgttccc gaagtcgaac cctacagacc atctgaccag 900
gctgccatcg ctcagttggc tgaccacgct cctcctgagc aatatcaacc tcttgctact 960
tcgaaagcca tgtctgatgt tatgacgaag ttggctttgg atcccaaggc actcgccgac 1020
tacaaagctg atcaccgcgc ctttgctcaa tctgtccccg acttgacgcc tcaggagcgt 1080
gcggctttgg agctcggtga ttcgtgggct attcgttgcg cgatgaagaa tatgccctcg 1140
tcgctcttgg acgctgctcg tgaatccggc gaagaggcat cccaaaacgg tttcgcgtgg 1200
gtcatcgtcg ttggtgttat cggtgtcatc ggatcagtca tgagcacgga ataa 1254

<210> SEQ ID NO 91
<211> LENGTH: 424
<212> TYPE: PRT
<213> ORGANISM: Artificial Sequence
<220> FEATURE:
<223> OTHER INFORMATION: OMP CycD, complete

<400> SEQUENCE: 91

Met Glu His His His His His His His His Thr Ser Thr Gln Thr Lys
1               5                   10                  15

Ala Gly Ser Leu Thr Ile Val Gly Thr Gly Ile Glu Ser Ile Gly Gln
            20                  25                  30

Met Thr Leu Gln Ala Leu Ser Tyr Ile Glu Ala Ala Ala Lys Val Phe
        35                  40                  45

Tyr Cys Val Ile Asp Pro Ala Thr Glu Ala Phe Ile Leu Thr Lys Asn
    50                  55                  60

Lys Asn Cys Val Asp Leu Tyr Gln Tyr Tyr Asp Asn Gly Lys Ser Arg
65                  70                  75                  80

Leu Asn Thr Tyr Thr Gln Met Ser Glu Leu Met Val Arg Glu Val Arg
                85                  90                  95

Lys Gly Leu Asp Val Val Gly Val Phe Tyr Gly His Pro Gly Val Phe
            100                 105                 110

Val Asn Pro Ser His Arg Ala Leu Ala Ile Ala Lys Ser Glu Gly Tyr
        115                 120                 125

Arg Ala Arg Met Leu Pro Gly Val Ser Ala Glu Asp Cys Leu Phe Ala
    130                 135                 140

Asp Leu Cys Ile Asp Pro Ser Asn Pro Gly Cys Leu Thr Tyr Glu Ala
145                 150                 155                 160

Ser Asp Phe Leu Ile Arg Asp Arg Pro Val Ser Ile His Ser His Leu
                165                 170                 175

Val Leu Phe Gln Val Gly Cys Val Gly Ile Ala Asp Phe Asn Phe Thr
            180                 185                 190

Gly Phe Asp Asn Asn Lys Phe Gly Val Leu Val Asp Arg Leu Glu Gln
        195                 200                 205

Glu Tyr Gly Ala Glu His Pro Val Val His Tyr Ile Ala Ala Met Met
    210                 215                 220

Pro His Gln Asp Pro Val Thr Asp Lys Tyr Thr Val Ala Gln Leu Arg
225                 230                 235                 240

Glu Pro Glu Ile Ala Lys Arg Val Gly Gly Val Ser Thr Phe Tyr Ile

-continued

```
            245                 250                 255

Pro Pro Lys Ala Arg Lys Ala Ser Asn Leu Asp Ile Ile Arg Arg Leu
            260                 265                 270

Glu Leu Leu Pro Ala Gly Gln Val Pro Asp Lys Lys Ala Arg Ile Tyr
        275                 280                 285

Pro Ala Asn Gln Trp Glu Pro Asp Val Pro Glu Val Glu Pro Tyr Arg
    290                 295                 300

Pro Ser Asp Gln Ala Ala Ile Ala Gln Leu Ala Asp His Ala Pro Pro
305                 310                 315                 320

Glu Gln Tyr Gln Pro Leu Ala Thr Ser Lys Ala Met Ser Asp Val Met
                325                 330                 335

Thr Lys Leu Ala Leu Asp Pro Lys Ala Leu Ala Asp Tyr Lys Ala Asp
            340                 345                 350

His Arg Ala Phe Ala Gln Ser Val Pro Asp Leu Thr Pro Gln Glu Arg
        355                 360                 365

Ala Ala Leu Glu Leu Gly Asp Ser Trp Ala Ile Arg Cys Ala Met Lys
    370                 375                 380

Asn Met Pro Ser Ser Leu Leu Asp Ala Ala Arg Glu Ser Gly Glu Glu
385                 390                 395                 400

Ala Ser Gln Asn Gly Phe Pro Leu Val Leu Ala Ala Leu Leu Val Ile
                405                 410                 415

Val Gly Ser Val Met Ser Thr Glu
            420
```

<210> SEQ ID NO 92
<211> LENGTH: 1275
<212> TYPE: DNA
<213> ORGANISM: Artificial Sequence
<220> FEATURE:
<223> OTHER INFORMATION: OMP CycD, complete

<400> SEQUENCE: 92

```
atggagcatc atcatcatca tcatcatcat acttccactc agaccaaagc tggctcactc     60

accatcgtcg gtaccggtat cgagagtatc ggacaaatga cgcttcaggc gttgtcctac    120

atcgaagccg ccgcgaaggt tttctactgc gtcatcgacc ccgccactga ggcattcatc    180

ctcaccaaga acaagaactg cgttgacttg tatcagtatt acgacaatgg caagtccaga    240

ttgaacactt acacccaaat gtcagagctc atggtcaggg aagtccgcaa gggcctcgat    300

gtcgtgggcg tcttctacgg ccacccagga gtgttcgtga acccgtctca ccgagctctg    360

gctatcgcca agagtgaagg ctaccgagcg aggatgcttc caggcgtgtc tgcggaagat    420

tgtctcttcg cggacttgtg cattgatcct tcgaacccgg gttgcctgac ctacgaggca    480

tcggatttcc tgatcaggga tcgcccggtc agcatccaca gtcacttggt cctgttccaa    540

gtcggatgcg tcggtatcgc cgacttcaac ttcactggat tcgacaacaa caaattcggc    600

gttctcgtcg accgtctcga gcaagaatac ggcgccgagc accctgtcgt ccattacatc    660

gcagctatga tgccacacca agacccagtc accgataaat acaccgtcgc gcagctccgt    720

gagcccgaga tcgcgaagcg tgttggcggt gtctcgactt tctacatccc tcccaaggcc    780

aggaaagcat cgaacttgga catcataagg cgcctagagc tcttgcctgc tgggcaagtt    840

cccgacaaga aagcgcgtat ttacccggcc aaccagtggg agcccgatgt tcccgaagtc    900

gaaccctaca gaccatctga ccaggctgcc atcgctcagt tggctgacca cgctcctcct    960

gagcaatatc aacctcttgc tacttcgaaa gccatgtctg atgttatgac gaagttggct   1020
```

```
ttggatccca aggcactcgc cgactacaaa gctgatcacc gcgcctttgc tcaatctgtc   1080

cccgacttga cgcctcagga gcgtgcggct ttggagctcg gtgattcgtg ggctattcgt   1140

tgcgcgatga agaatatgcc ctcgtcgctc ttggacgctg ctcgtgaatc cggcgaagag   1200

gcatcccaaa acggtttccc actggtgctg gctgcactgc tcgtcatcgt tggttcagtc   1260

atgagcacgg aataa                                                    1275


<210> SEQ ID NO 93
<211> LENGTH: 421
<212> TYPE: PRT
<213> ORGANISM: Artificial Sequence
<220> FEATURE:
<223> OTHER INFORMATION: OMP KenA, complete

<400> SEQUENCE: 93

Met Glu His His His His His His His His Thr Ser Thr Gln Thr Lys
1               5                   10                  15

Ala Gly Ser Leu Thr Ile Val Gly Thr Gly Ile Glu Ser Ile Gly Gln
            20                  25                  30

Met Thr Leu Gln Ala Leu Ser Tyr Ile Glu Ala Ala Ala Lys Val Phe
        35                  40                  45

Tyr Cys Val Ile Asp Pro Ala Thr Glu Ala Phe Ile Leu Thr Lys Asn
    50                  55                  60

Lys Asn Cys Val Asp Leu Tyr Gln Tyr Tyr Asp Asn Gly Lys Ser Arg
65                  70                  75                  80

Leu Asn Thr Tyr Thr Gln Met Ser Glu Leu Met Val Arg Glu Val Arg
                85                  90                  95

Lys Gly Leu Asp Val Val Gly Val Phe Tyr Gly His Pro Gly Val Phe
            100                 105                 110

Val Asn Pro Ser His Arg Ala Leu Ala Ile Ala Lys Ser Glu Gly Tyr
        115                 120                 125

Arg Ala Arg Met Leu Pro Gly Val Ser Ala Glu Asp Cys Leu Phe Ala
    130                 135                 140

Asp Leu Cys Ile Asp Pro Ser Asn Pro Gly Cys Leu Thr Tyr Glu Ala
145                 150                 155                 160

Ser Asp Phe Leu Ile Arg Asp Arg Pro Val Ser Ile His Ser His Leu
                165                 170                 175

Val Leu Phe Gln Val Gly Cys Val Gly Ile Ala Asp Phe Asn Phe Thr
            180                 185                 190

Gly Phe Asp Asn Asn Lys Phe Gly Val Leu Val Asp Arg Leu Glu Gln
        195                 200                 205

Glu Tyr Gly Ala Glu His Pro Val Val His Tyr Ile Ala Ala Met Met
    210                 215                 220

Pro His Gln Asp Pro Val Thr Asp Lys Tyr Thr Val Ala Gln Leu Arg
225                 230                 235                 240

Glu Pro Glu Ile Ala Lys Arg Val Gly Gly Val Ser Thr Phe Tyr Ile
                245                 250                 255

Pro Pro Lys Ala Arg Lys Ala Ser Asn Leu Asp Ile Ile Arg Arg Leu
            260                 265                 270

Glu Leu Leu Pro Ala Gly Gln Val Pro Asp Lys Lys Ala Arg Ile Tyr
        275                 280                 285

Pro Ala Asn Gln Trp Glu Pro Asp Val Pro Glu Val Glu Pro Tyr Arg
    290                 295                 300

Pro Ser Asp Gln Ala Ala Ile Ala Gln Leu Ala Asp His Ala Pro Pro
305                 310                 315                 320
```

```
Glu Gln Tyr Gln Pro Leu Ala Thr Ser Lys Ala Met Ser Asp Val Met
                325                 330                 335

Thr Lys Leu Ala Leu Asp Pro Lys Ala Leu Ala Asp Tyr Lys Ala Asp
            340                 345                 350

His Arg Ala Phe Ala Gln Ser Val Pro Asp Leu Thr Pro Gln Glu Arg
        355                 360                 365

Ala Ala Leu Glu Leu Gly Asp Ser Trp Ala Ile Arg Cys Ala Met Lys
    370                 375                 380

Asn Met Pro Ser Ser Leu Leu Asp Ala Ala Arg Glu Ser Gly Glu Glu
385                 390                 395                 400

Ala Ser Gln Asn Gly Phe Pro Gln Phe Ile Ala Val Val Val Val Ala
                405                 410                 415

Val Val Cys Cys Phe
            420
```

<210> SEQ ID NO 94
<211> LENGTH: 1266
<212> TYPE: DNA
<213> ORGANISM: Artificial Sequence
<220> FEATURE:
<223> OTHER INFORMATION: OMP KenA, complete

<400> SEQUENCE: 94

```
atggagcatc atcatcatca tcatcatcat acttccactc agaccaaagc tggctcactc     60

accatcgtcg gtaccggtat cgagagtatc ggacaaatga cgcttcaggc gttgtcctac    120

atcgaagccg ccgcgaaggt tttctactgc gtcatcgacc ccgccactga ggcattcatc    180

ctcaccaaga acaagaactg cgttgacttg tatcagtatt acgacaatgg caagtccaga    240

ttgaacactt acacccaaat gtcagagctc atggtcaggg aagtccgcaa gggcctcgat    300

gtcgtgggcg tcttctacgg ccacccagga gtgttcgtga acccgtctca ccgagctctg    360

gctatcgcca agagtgaagg ctaccgagcg aggatgcttc caggcgtgtc tgcggaagat    420

tgtctcttcg cggacttgtg cattgatcct tcgaacccgg gttgcctgac ctacgaggca    480

tcggatttcc tgatcaggga tcgcccggtc agcatccaca gtcacttggt cctgttccaa    540

gtcggatgcg tcggtatcgc cgacttcaac ttcactggat tcgacaacaa caaattcggc    600

gttctcgtcg accgtctcga gcaagaatac ggcgccgagc accctgtcgt ccattacatc    660

gcagctatga tgccacacca agacccagtc accgataaat acaccgtcgc gcagctccgt    720

gagcccgaga tcgcgaagcg tgttggcggt gtctcgactt tctacatccc tcccaaggcc    780

aggaaagcat cgaacttgga catcataagg cgcctagagc tcttgcctgc tgggcaagtt    840

cccgacaaga aagcgcgtat ttacccggcc aaccagtggg agcccgatgt tcccgaagtc    900

gaaccctaca gaccatctga ccaggctgcc atcgctcagt tggctgacca cgctcctcct    960

gagcaatatc aacctcttgc tacttcgaaa gccatgtctg atgttatgac gaagttggct   1020

ttggatccca aggcactcgc cgactacaaa gctgatcacc gcgcctttgc tcaatctgtc   1080

cccgacttga cgcctcagga gcgtgcggct ttggagctcg gtgattcgtg ggctattcgt   1140

tgcgcgatga agaatatgcc ctcgtcgctc ttggacgctg ctcgtgaatc cggcgaagag   1200

gcatcccaaa acggtttccc acagttcatt gccgttgtag ttgtggcagt cgtgtgctgt   1260

ttctaa                                                              1266
```

<210> SEQ ID NO 95
<211> LENGTH: 418

<212> TYPE: PRT
<213> ORGANISM: Artificial Sequence
<220> FEATURE:
<223> OTHER INFORMATION: OMP DicA, complete

<400> SEQUENCE: 95

```
Met Glu His His His His His His His His Thr Ser Thr Gln Thr Lys
1               5                   10                  15

Ala Gly Ser Leu Thr Ile Val Gly Thr Gly Ile Glu Ser Ile Gly Gln
            20                  25                  30

Met Thr Leu Gln Ala Leu Ser Tyr Ile Glu Ala Ala Ala Lys Val Phe
        35                  40                  45

Tyr Cys Val Ile Asp Pro Ala Thr Glu Ala Phe Ile Leu Thr Lys Asn
    50                  55                  60

Lys Asn Cys Val Asp Leu Tyr Gln Tyr Tyr Asp Asn Gly Lys Ser Arg
65                  70                  75                  80

Leu Asn Thr Tyr Thr Gln Met Ser Glu Leu Met Val Arg Glu Val Arg
                85                  90                  95

Lys Gly Leu Asp Val Val Gly Val Phe Tyr Gly His Pro Gly Val Phe
            100                 105                 110

Val Asn Pro Ser His Arg Ala Leu Ala Ile Ala Lys Ser Glu Gly Tyr
        115                 120                 125

Arg Ala Arg Met Leu Pro Gly Val Ser Ala Glu Asp Cys Leu Phe Ala
    130                 135                 140

Asp Leu Cys Ile Asp Pro Ser Asn Pro Gly Cys Leu Thr Tyr Glu Ala
145                 150                 155                 160

Ser Asp Phe Leu Ile Arg Asp Arg Pro Val Ser Ile His Ser His Leu
                165                 170                 175

Val Leu Phe Gln Val Gly Cys Val Gly Ile Ala Asp Phe Asn Phe Thr
            180                 185                 190

Gly Phe Asp Asn Asn Lys Phe Gly Val Leu Val Asp Arg Leu Glu Gln
        195                 200                 205

Glu Tyr Gly Ala Glu His Pro Val Val His Tyr Ile Ala Ala Met Met
    210                 215                 220

Pro His Gln Asp Pro Val Thr Asp Lys Tyr Thr Val Ala Gln Leu Arg
225                 230                 235                 240

Glu Pro Glu Ile Ala Lys Arg Val Gly Gly Val Ser Thr Phe Tyr Ile
                245                 250                 255

Pro Pro Lys Ala Arg Lys Ala Ser Asn Leu Asp Ile Ile Arg Arg Leu
            260                 265                 270

Glu Leu Leu Pro Ala Gly Gln Val Pro Asp Lys Lys Ala Arg Ile Tyr
        275                 280                 285

Pro Ala Asn Gln Trp Glu Pro Asp Val Pro Glu Val Glu Pro Tyr Arg
    290                 295                 300

Pro Ser Asp Gln Ala Ala Ile Ala Gln Leu Ala Asp His Ala Pro Pro
305                 310                 315                 320

Glu Gln Tyr Gln Pro Leu Ala Thr Ser Lys Ala Met Ser Asp Val Met
                325                 330                 335

Thr Lys Leu Ala Leu Asp Pro Lys Ala Leu Ala Asp Tyr Lys Ala Asp
            340                 345                 350

His Arg Ala Phe Ala Gln Ser Val Pro Asp Leu Thr Pro Gln Glu Arg
        355                 360                 365

Ala Ala Leu Glu Leu Gly Asp Ser Trp Ala Ile Arg Cys Ala Met Lys
    370                 375                 380
```

```
Asn Met Pro Ser Ser Leu Leu Asp Ala Ala Arg Glu Ser Gly Glu Glu
385                 390                 395                 400

Ala Ser Gln Asn Gly Phe Pro Ala Thr Thr Val Val Val Val Val Ile
                405                 410                 415

Val Gly


<210> SEQ ID NO 96
<211> LENGTH: 1257
<212> TYPE: DNA
<213> ORGANISM: Artificial Sequence
<220> FEATURE:
<223> OTHER INFORMATION: OMP DicA, complete

<400> SEQUENCE: 96

atggagcatc atcatcatca tcatcatcat acttccactc agaccaaagc tggctcactc     60

accatcgtcg gtaccggtat cgagagtatc ggacaaatga cgcttcaggc gttgtcctac    120

atcgaagccg ccgcgaaggt tttctactgc gtcatcgacc ccgccactga ggcattcatc    180

ctcaccaaga acaagaactg cgttgacttg tatcagtatt acgacaatgg caagtccaga    240

ttgaacactt acacccaaat gtcagagctc atggtcaggg aagtccgcaa gggcctcgat    300

gtcgtgggcg tcttctacgg ccacccagga gtgttcgtga acccgtctca ccgagctctg    360

gctatcgcca agagtgaagg ctaccgagcg aggatgcttc caggcgtgtc tgcggaagat    420

tgtctcttcg cggacttgtg cattgatcct tcgaacccgg gttgcctgac ctacgaggca    480

tcggatttcc tgatcaggga tcgcccggtc agcatccaca gtcacttggt cctgttccaa    540

gtcggatgcg tcggtatcgc cgacttcaac ttcactggat tcgacaacaa caaattcggc    600

gttctcgtcg accgtctcga gcaagaatac ggcgccgagc accctgtcgt ccattacatc    660

gcagctatga tgccacacca agacccagtc accgataaat acaccgtcgc gcagctccgt    720

gagcccgaga tcgcgaagcg tgttggcggt gtctcgactt tctacatccc tcccaaggcc    780

aggaaagcat cgaacttgga catcataagg cgcctagagc tcttgcctgc tgggcaagtt    840

cccgacaaga aagcgcgtat ttacccggcc aaccagtggg agcccgatgt tcccgaagtc    900

gaaccctaca gaccatctga ccaggctgcc atcgctcagt tggctgacca cgctcctcct    960

gagcaatatc aacctcttgc tacttcgaaa gccatgtctg atgttatgac gaagttggct   1020

ttggatccca aggcactcgc cgactacaaa gctgatcacc gcgcctttgc tcaatctgtc   1080

cccgacttga cgcctcagga gcgtgcggct ttggagctcg gtgattcgtg ggctattcgt   1140

tgcgcgatga agaatatgcc ctcgtcgctc ttggacgctg ctcgtgaatc cggcgaagag   1200

gcatcccaaa acggtttccc agcaacgacc gtagtagttg ttgttattgt gggttaa      1257


<210> SEQ ID NO 97
<211> LENGTH: 427
<212> TYPE: PRT
<213> ORGANISM: Artificial Sequence
<220> FEATURE:
<223> OTHER INFORMATION: OMP R1, complete

<400> SEQUENCE: 97

Met Glu His His His His His His His His Thr Ser Thr Gln Thr Lys
1               5                   10                  15

Ala Gly Ser Leu Thr Ile Val Gly Thr Gly Ile Glu Ser Ile Gly Gln
            20                  25                  30

Met Thr Leu Gln Ala Leu Ser Tyr Ile Glu Ala Ala Ala Lys Val Phe
        35                  40                  45
```

```
Tyr Cys Val Ile Asp Pro Ala Thr Glu Ala Phe Ile Leu Thr Lys Asn
    50                  55                  60

Lys Asn Cys Val Asp Leu Tyr Gln Tyr Tyr Asp Asn Gly Lys Ser Arg
65                  70                  75                  80

Leu Asn Thr Tyr Thr Gln Met Ser Glu Leu Met Val Arg Glu Val Arg
                85                  90                  95

Lys Gly Leu Asp Val Val Gly Val Phe Tyr Gly His Pro Gly Val Phe
            100                 105                 110

Val Asn Pro Ser His Arg Ala Leu Ala Ile Ala Lys Ser Glu Gly Tyr
        115                 120                 125

Arg Ala Arg Met Leu Pro Gly Val Ser Ala Glu Asp Cys Leu Phe Ala
    130                 135                 140

Asp Leu Cys Ile Asp Pro Ser Asn Pro Gly Cys Leu Thr Tyr Glu Ala
145                 150                 155                 160

Ser Asp Phe Leu Ile Arg Asp Arg Pro Val Ser Ile His Ser His Leu
                165                 170                 175

Val Leu Phe Gln Val Gly Cys Val Gly Ile Ala Asp Phe Asn Phe Thr
            180                 185                 190

Gly Phe Asp Asn Asn Lys Phe Gly Val Leu Val Asp Arg Leu Glu Gln
        195                 200                 205

Glu Tyr Gly Ala Glu His Pro Val Val His Tyr Ile Ala Ala Met Met
    210                 215                 220

Pro His Gln Asp Pro Val Thr Asp Lys Tyr Thr Val Ala Gln Leu Arg
225                 230                 235                 240

Glu Pro Glu Ile Ala Lys Arg Val Gly Gly Val Ser Thr Phe Tyr Ile
                245                 250                 255

Pro Pro Lys Ala Arg Lys Ala Ser Asn Leu Asp Ile Ile Arg Arg Leu
            260                 265                 270

Glu Leu Leu Pro Ala Gly Gln Val Pro Asp Lys Lys Ala Arg Ile Tyr
        275                 280                 285

Pro Ala Asn Gln Trp Glu Pro Asp Val Pro Glu Val Glu Pro Tyr Arg
    290                 295                 300

Pro Ser Asp Gln Ala Ala Ile Ala Gln Leu Ala Asp His Ala Pro Pro
305                 310                 315                 320

Glu Gln Tyr Gln Pro Leu Ala Thr Ser Lys Ala Met Ser Asp Val Met
                325                 330                 335

Thr Lys Leu Ala Leu Asp Pro Lys Ala Leu Ala Asp Tyr Lys Ala Asp
            340                 345                 350

His Arg Ala Phe Ala Gln Ser Val Pro Asp Leu Thr Pro Gln Glu Arg
        355                 360                 365

Ala Ala Leu Glu Leu Gly Asp Ser Trp Ala Ile Arg Cys Ala Met Lys
    370                 375                 380

Asn Met Pro Ser Ser Leu Leu Asp Ala Ala Arg Glu Ser Gly Glu Glu
385                 390                 395                 400

Ala Ser Gln Asn Gly Phe Pro Val Phe Ala Glu Phe Leu Pro Leu Phe
                405                 410                 415

Ser Lys Phe Gly Ser Arg Met His Ile Leu Lys
            420                 425
```

<210> SEQ ID NO 98
<211> LENGTH: 1284
<212> TYPE: DNA
<213> ORGANISM: Artificial Sequence
<220> FEATURE:
<223> OTHER INFORMATION: OMP R1, complete

<400> SEQUENCE: 98

```
atggagcatc atcatcatca tcatcatcat acttccactc agaccaaagc tggctcactc     60
accatcgtcg gtaccggtat cgagagtatc ggacaaatga cgcttcaggc gttgtcctac    120
atcgaagccg ccgcgaaggt tttctactgc gtcatcgacc ccgccactga ggcattcatc    180
ctcaccaaga acaagaactg cgttgacttg tatcagtatt acgacaatgg caagtccaga    240
ttgaacactt acacccaaat gtcagagctc atggtcaggg aagtccgcaa gggcctcgat    300
gtcgtgggcg tcttctacgg ccacccagga gtgttcgtga acccgtctca ccgagctctg    360
gctatcgcca agagtgaagg ctaccgagcg aggatgcttc caggcgtgtc tgcggaagat    420
tgtctcttcg cggacttgtg cattgatcct tcgaacccgg gttgcctgac ctacgaggca    480
tcggatttcc tgatcaggga tcgcccggtc agcatccaca gtcacttggt cctgttccaa    540
gtcggatgcg tcggtatcgc cgacttcaac ttcactggat tcgacaacaa caaattcggc    600
gttctcgtcg accgtctcga gcaagaatac ggcgccgagc accctgtcgt ccattacatc    660
gcagctatga tgccacacca agacccagtc accgataaat acaccgtcgc gcagctccgt    720
gagcccgaga tcgcgaagcg tgttggcggt gtctcgactt tctacatccc tcccaaggcc    780
aggaaagcat cgaacttgga catcataagg cgcctagagc tcttgcctgc tgggcaagtt    840
cccgacaaga aagcgcgtat ttacccggcc aaccagtggg agcccgatgt tcccgaagtc    900
gaaccctaca gaccatctga ccaggctgcc atcgctcagt tggctgacca cgctcctcct    960
gagcaatatc aacctcttgc tacttcgaaa gccatgtctg atgttatgac gaagttggct   1020
ttggatccca aggcactcgc cgactacaaa gctgatcacc gcgcctttgc tcaatctgtc   1080
cccgacttga cgcctcagga gcgtgcggct ttggagctcg gtgattcgtg ggctattcgt   1140
tgcgcgatga agaatatgcc ctcgtcgctc ttggacgctg ctcgtgaatc cggcgaagag   1200
gcatcccaaa acggtttccc agtctttgca gaatttctgc ctctgttcag caaattcggt   1260
tcgcggatgc acattctgaa ataa                                           1284
```

<210> SEQ ID NO 99
<211> LENGTH: 30
<212> TYPE: PRT
<213> ORGANISM: Omphalotus olearius
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (16)..(16)
<223> OTHER INFORMATION: METHYLATION
<220> FEATURE:
<221> NAME/KEY: MOD_RES
<222> LOCATION: (17)..(17)
<223> OTHER INFORMATION: METHYLATION
<220> FEATURE:
<221> NAME/KEY: MOD_RES
<222> LOCATION: (18)..(18)
<223> OTHER INFORMATION: METHYLATION
<220> FEATURE:
<221> NAME/KEY: MOD_RES
<222> LOCATION: (19)..(19)
<223> OTHER INFORMATION: METHYLATION
<220> FEATURE:
<221> NAME/KEY: MOD_RES
<222> LOCATION: (20)..(20)
<223> OTHER INFORMATION: METHYLATION
<220> FEATURE:
<221> NAME/KEY: MOD_RES
<222> LOCATION: (21)..(21)

<223> OTHER INFORMATION: METHYLATION
<220> FEATURE:
<221> NAME/KEY: MOD_RES
<222> LOCATION: (23)..(23)
<223> OTHER INFORMATION: METHYLATION
<220> FEATURE:
<221> NAME/KEY: MOD_RES
<222> LOCATION: (24)..(24)
<223> OTHER INFORMATION: METHYLATION
<220> FEATURE:
<221> NAME/KEY: MOD_RES
<222> LOCATION: (26)..(26)
<223> OTHER INFORMATION: METHYLATION

<400> SEQUENCE: 99

```
Glu Ser Gly Glu Glu Ala Ser Gln Asn Gly Phe Pro Trp Val Ile Val
1               5                   10                  15

Val Gly Val Ile Gly Val Ile Gly Ser Val Met Ser Thr Glu
            20                  25                  30
```

<210> SEQ ID NO 100
<211> LENGTH: 41
<212> TYPE: PRT
<213> ORGANISM: Dendrothele bispora
<220> FEATURE:
<221> NAME/KEY: MOD_RES
<222> LOCATION: (25)..(25)
<223> OTHER INFORMATION: METHYLATION
<220> FEATURE:
<221> NAME/KEY: MOD_RES
<222> LOCATION: (27)..(27)
<223> OTHER INFORMATION: METHYLATION
<220> FEATURE:
<221> NAME/KEY: MOD_RES
<222> LOCATION: (28)..(28)
<223> OTHER INFORMATION: METHYLATION
<220> FEATURE:
<221> NAME/KEY: MOD_RES
<222> LOCATION: (29)..(29)
<223> OTHER INFORMATION: METHYLATION
<220> FEATURE:
<221> NAME/KEY: MOD_RES
<222> LOCATION: (30)..(30)
<223> OTHER INFORMATION: METHYLATION
<220> FEATURE:
<221> NAME/KEY: MOD_RES
<222> LOCATION: (31)..(31)
<223> OTHER INFORMATION: METHYLATION
<220> FEATURE:
<221> NAME/KEY: MOD_RES
<222> LOCATION: (32)..(32)
<223> OTHER INFORMATION: METHYLATION
<220> FEATURE:
<221> NAME/KEY: MOD_RES
<222> LOCATION: (34)..(34)
<223> OTHER INFORMATION: METHYLATION
<220> FEATURE:
<221> NAME/KEY: MOD_RES
<222> LOCATION: (35)..(35)
<223> OTHER INFORMATION: METHYLATION
<220> FEATURE:
<221> NAME/KEY: MOD_RES
<222> LOCATION: (37)..(37)
<223> OTHER INFORMATION: METHYLATION

<400> SEQUENCE: 100

```
Asn Met Pro Ser Ser Leu Leu Glu Ala Ala Ser Gln Ser Val Glu Glu
1               5                   10                  15

Ala Ser Met Asn Gly Phe Pro Trp Val Ile Val Thr Gly Ile Val Gly
            20                  25                  30

Val Ile Gly Ser Val Val Ser Ser Ala
        35                  40
```

```
<210> SEQ ID NO 101
<211> LENGTH: 24
<212> TYPE: PRT
<213> ORGANISM: Omphalotus olearius
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (16)..(16)
<223> OTHER INFORMATION: METHYLATION
<220> FEATURE:
<221> NAME/KEY: MOD_RES
<222> LOCATION: (17)..(17)
<223> OTHER INFORMATION: METHYLATION
<220> FEATURE:
<221> NAME/KEY: MOD_RES
<222> LOCATION: (18)..(18)
<223> OTHER INFORMATION: METHYLATION
<220> FEATURE:
<221> NAME/KEY: MOD_RES
<222> LOCATION: (19)..(19)
<223> OTHER INFORMATION: METHYLATION
<220> FEATURE:
<221> NAME/KEY: MOD_RES
<222> LOCATION: (20)..(20)
<223> OTHER INFORMATION: METHYLATION
<220> FEATURE:
<221> NAME/KEY: MOD_RES
<222> LOCATION: (21)..(21)
<223> OTHER INFORMATION: METHYLATION
<220> FEATURE:
<221> NAME/KEY: MOD_RES
<222> LOCATION: (23)..(23)
<223> OTHER INFORMATION: METHYLATION

<400> SEQUENCE: 101

Glu Ser Gly Glu Glu Ala Ser Gln Asn Gly Phe Pro Trp Val Ile Val
1               5                   10                  15

Val Gly Val Ile Gly Val Ile Gly
            20


<210> SEQ ID NO 102
<211> LENGTH: 24
<212> TYPE: PRT
<213> ORGANISM: Omphalotus olearius
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (16)..(16)
<223> OTHER INFORMATION: METHYLATION
<220> FEATURE:
<221> NAME/KEY: MOD_RES
<222> LOCATION: (17)..(17)
<223> OTHER INFORMATION: METHYLATION
<220> FEATURE:
<221> NAME/KEY: MOD_RES
<222> LOCATION: (18)..(18)
<223> OTHER INFORMATION: METHYLATION
<220> FEATURE:
<221> NAME/KEY: MOD_RES
<222> LOCATION: (19)..(19)
<223> OTHER INFORMATION: METHYLATION
<220> FEATURE:
<221> NAME/KEY: MOD_RES
<222> LOCATION: (20)..(20)
<223> OTHER INFORMATION: METHYLATION
<220> FEATURE:
<221> NAME/KEY: MOD_RES
<222> LOCATION: (21)..(21)
<223> OTHER INFORMATION: METHYLATION
```

```
<220> FEATURE:
<221> NAME/KEY: MOD_RES
<222> LOCATION: (23)..(23)
<223> OTHER INFORMATION: METHYLATION

<400> SEQUENCE: 102

Glu Ser Gly Glu Asn Leu Tyr Phe Gln Gly Phe Pro Trp Val Ile Val
1               5                   10                  15

Val Gly Val Ile Gly Val Ile Gly
            20


<210> SEQ ID NO 103
<211> LENGTH: 11
<212> TYPE: PRT
<213> ORGANISM: Artificial Sequence
<220> FEATURE:
<223> OTHER INFORMATION: peptide resembling cyclosporin A
<220> FEATURE:
<221> NAME/KEY: MOD_RES
<222> LOCATION: (3)..(3)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (6)..(6)
<223> OTHER INFORMATION: METHYLATION

<400> SEQUENCE: 103

Leu Val Leu Ala Ala Leu Leu Val Ile Val Gly
1               5                   10


<210> SEQ ID NO 104
<211> LENGTH: 11
<212> TYPE: PRT
<213> ORGANISM: Artificial Sequence
<220> FEATURE:
<223> OTHER INFORMATION: peptide resembling dictyonamide A
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (3)..(3)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (6)..(6)
<223> OTHER INFORMATION: METHYLATION
<220> FEATURE:
<221> NAME/KEY: MOD_RES
<222> LOCATION: (8)..(8)
<223> OTHER INFORMATION: METHYLATION

<400> SEQUENCE: 104

Ala Thr Thr Val Val Val Val Val Ile Val Gly
1               5                   10
```

<210> SEQ ID NO 105
<211> LENGTH: 20
<212> TYPE: PRT
<213> ORGANISM: Artificial Sequence
<220> FEATURE:
<223> OTHER INFORMATION: peptide resembling antimalarial R1 peptide
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (3)..(3)
<223> OTHER INFORMATION: METHYLATION

<400> SEQUENCE: 105

Val Phe Ala Glu Phe Leu Pro Leu Phe Ser Lys Phe Gly Ser Arg Met
1               5                   10                  15

His Ile Leu Lys
            20

<210> SEQ ID NO 106
<211> LENGTH: 14
<212> TYPE: PRT
<213> ORGANISM: Artificial Sequence
<220> FEATURE:
<223> OTHER INFORMATION: peptide resembling kendarimide A
<220> FEATURE:
<221> NAME/KEY: MOD_RES
<222> LOCATION: (8)..(8)
<223> OTHER INFORMATION: METHYLATION
<220> FEATURE:
<221> NAME/KEY: MOD_RES
<222> LOCATION: (9)..(9)
<223> OTHER INFORMATION: METHYLATION
<220> FEATURE:
<221> NAME/KEY: DISULFID
<222> LOCATION: (12)..(13)

<400> SEQUENCE: 106

Gln Phe Ile Ala Val Val Val Val Ala Val Val Cys Cys Phe
1               5                   10

<210> SEQ ID NO 107
<211> LENGTH: 1287
<212> TYPE: DNA
<213> ORGANISM: Artificial Sequence
<220> FEATURE:
<223> OTHER INFORMATION: D. bispora 765750 codon optimized

<400> SEQUENCE: 107
catatggaac atcatcatca tcatcatcat cattcttcta ctcaaaccaa acccggttcg     60
ctcatcgtcg tcggtacagg catcgagagc atcggtcaaa tgacgctcca agccttatcg    120
tacattgaag ctgcttccaa agtcttctat tgtgtcatcg accctgcgac agaggctttt    180
atcctcacca agaacaagaa ttgtgtcgac ttgtatcagt actacgacaa tggcaagtct    240
agaatggata cttacaccca aatggctgag ctcatgctca aggaagtccg caatggcctc    300
gacgttgtcg gggtattcta tggccatccg ggcgtgttcg tgaacccttc tcacagggca    360
ttggctatcg ccagaagcga gggataccaa gctcgtatgc ttccaggagt atctgcagag    420
gactgcctct ttgccgactt atgcatcgac ccctcgaacc ccggctgctt gacctacgaa    480
gcatccgatt tcctcatcag agagagacca gtgaacgttc acagtcacct cattcttttc    540
caagttggat gcgtcggtat cgcagacttc aatttcagcg gattcgacaa ttcgaaattt    600
accattctgg ttgaccgtct cgagcaagaa tacggcccag accataccgt cgtgcattat    660
atcgcagcta tgatgcctca ccaagatccc gtcaccgaca agttcacgat cggacaactc 720
cgtgaacccg aaatcgccaa acgagtaggt ggtgtttcga ctttttacat ccctccaaag 780
gccagaaagg atatcaacac cgatatcatc cgactcttgg aattcctacc tgctggtaaa 840
gttcccgaca aacacaccca aatctaccca cctaatcaat gggaacccga cgtgcctact 900
ctacctccct atggacaaaa cgaacaggct gctatcacta gattggaagc tcacgctccc 960
cccgaagagt atcagcctct ggccacttcc aaagctatga ctgacgtcat gaccaaacta 1020
gctttggatc ccaaggcgct cgccgagtat aaggctgatc atcgagcctt cgctcagtct 1080
gttcctgact tgacgcctca agagagagca gctttggagc taggagattc atgggctatt 1140
cggtgcgcca tgaagaacat gccgtcctct ctcttggaag ccgctagcca gtccgtcgaa 1200
gaggcatcca tgaacggttt cccatgggtc atcgtcacgg gtatcgttgg ggtcatcgga 1260
tcggttgtga gcagtgcttg aaagctt 1287

<210> SEQ ID NO 108
<211> LENGTH: 1254
<212> TYPE: DNA
<213> ORGANISM: Lentinula edodes

<400> SEQUENCE: 108
atggagactc ctaccttaaa caaatccggc tccctcacta tcgttggcac tggcatcgag 60
agtattggtc aaatgaccct tcagaccttg tcttacatcg aagccgccga caaagttttt 120
tactgtgtca tagaccctgc caccgaagca ttcatcctca ccaagaacaa ggactgtgtc 180
gacctgtacc agtactacga taatggcaag tccaggatgg atacctacac ccaaatgtct 240
gaggttatgc tcagggaggt ccgcaagggc cttgatgttg taggcgtctt ctacggacac 300
ccaggtgtgt tcgttaaccc ttcgcttcga gcgctcgcta tcgccaaaag tgaggggttc 360
aaggctagga tgctgccggg cgtatctgcg gaggactgcc tttatgcaga cttgtgcatc 420
gatccttcga accccggatg tctgacctac gaagcatctg acttcctcat tcgagagagg 480
ccaacgaaca tttacagcca ttttatcctt ttccaagttg gatgtgtcgg tattgctgac 540
ttcaacttca ctggatttga aaactcgaaa ttcggaattc ttgttgaccg cctcgagaag 600
gagtatggcg cagaacatcc tgtcgtgcac tacatcgccg ctatgctccc tcacgaggat 660
cccgttaccg atcagtggac cattggacaa ctccgtgagc cggagttcta caaacgcgtc 720
ggcggtgttt ccactttcta catcccgcca aaggagcgaa aggagattaa cgttgatatc 780
attcgtgaac tcaagtttct ccctgagggg aaagttccgg atacgcgtac tcagatttac 840
ccacccaacc aatgggaacc cgaggtaccg actgttcctg cgtatggatc aaatgagcac 900
gccgctatcg ctcagttgga cactcacact cctcccgagc aatatcaacc tctcgctact 960
tccaaagcca tgactgatgt gatgaccaag ttggcgttgg atcccaaggc gctcgcagaa 1020
tacaaggctg accaccgagc cttcgctcag tccgttccgg atttgacggc gaatgagagg 1080
accgctttgg agattggaga ctcctgggcg ttccgctgcg ctatgaagga aatgcctatt 1140
tcactcctag acaacgccaa gcagtcaatg gaagaagcct ccgaacaagg cttcccgtgg 1200
atcatcgtcg ttggtgtcgt tggtgtcgtt ggttctgttg ttagtagcgc ctga 1254

<210> SEQ ID NO 109
<211> LENGTH: 384
<212> TYPE: DNA
<213> ORGANISM: Lentinula edodes

<400> SEQUENCE: 109
atgactgata ccacgaagat taaaaccgtt cgaaagttcc acgacctcct gaacgaagga 60
aagcttgatg aggctcatga gctcttggcc gaagacttgt ctgcgcacac cactgcgcat 120
atcgccgcag gggcaccccc gatgagtaaa gcagaggttc ttgaatctca tcaaggcatt 180
catcaagagc tggaagctaa gacaaccatc accgacgcca aggaggtcga tggaaatgtt 240
atcgtagtgg gaaagtccac tttcaatcac gacactatca aggaggttcc gttcaaggca 300
acctatgaat tcatcgggaa tcagattggc aaagtccatt tcgagacgga tcctaaccac 360
aaagttaaat ccttcagcct ctag 384

<210> SEQ ID NO 110
<211> LENGTH: 1236
<212> TYPE: DNA
<213> ORGANISM: Lentinula edodes

<400> SEQUENCE: 110
atgcttgtcc tgccgctaga catcgctgaa gctataattc gcgaactcct agccagaaag 60
gacaaggcta cagtgaaatc cttgtccctc gtccgctctt cctttacccc aatctgccaa 120
cgatatctcc tctcgaatat catcatatcc tgttcgaagg cagaaggaaa tagacgatac 180
caacgctcaa gtgacgcaac actaaagcta cttcgatcgt cacctcatct cgtttcgagt 240
atccgatcct tatctattct cgactccggt tttagctgga cacagctcga ccccgccctc 300
gttgatatct tgaattctct caccgatcta acctgcttca tatggaaagc cgcttccaac 360
tcctcacgcc cgacttattg gagagaatta ccccaacctc tgcaggactc aatcagagcc 420
acgatcagac gtccttcagt cacttcccta ttccttcatt tcgccgacct gaccgatcta 480
ttgaatgcaa gaatcattat ctctccctct ttgacatatc tgaacttacg aggcacggga 540
ttttccaaaa tcgccttgga actgactcgt ccgagtataa tacctttcgg agagatgccg 600
tctagattgt tcgtcacggc atgtaagctt gagtggatcg aggacgagaa gatgtgcttt 660
gggtggatca ctgctattct accgaatctc agtcttgaac ggcttcagaa actggcagtc 720
ttccgatctt cgctacaatc aaaattgcct gaacttcctt gggggggcgtt attataccac 780 cagtctgttc agtcaaacct ggaagagctt tggttcgata tgatctctac taatggtcct 840
ccagttgata ccatgtcgct cgaccgcttg ccttccttaa agcgactcgg gctatctatg 900
ggcctctcac gagtcttcga tgctaattgg gatttggttt taggattatc tagatttttt 960
gagaatacaa atgcagctgg aattactcat cttatccttt gctttagctt ttccagtact 1020
tctcttgtat tagacccact aaaggtgcca tgggggagtc tcgatgccgc tgtagcggca 1080
atacccacct tacgctgggt gggagtccag ttcgttgatt gtagacgtga accgactggc 1140
attattcctc ccaaaacgaa gattatgctg ccaatgttga ccgaaagggg aatattgcat 1200
tggtcgacta gcagagtaga atttccgcaa atttga 1236

<210> SEQ ID NO 111
<211> LENGTH: 2235
<212> TYPE: DNA
<213> ORGANISM: Lentinula edodes

<400> SEQUENCE: 111
atgtcagttc cgcagtggga tccataccca ccagtcagta gagacgaaac ctcagcaatc 60
acgtatcaga gcaagttgtg cggttctgtt actgtacgcg atccgtacag tgcacttgag 120 gtgcctttttg atgatagtga agagaccaaa gcctttgttc atgcacaacg caagtttgcg 180

```
cggacgtatc tagacgagat tcctgacaga gaaacgtggc tgcaaacgct gaaagagagt    240
tggaactaca gacgattcac tgtccccaaa cgcgaaagcg atggttacac ctacttcgaa    300
tacaacgacg gtcttcaatc tcaaatgtct ctacgtcgcg tgaaagtgag cgaagaggac    360
accattctca ccgagtctgg acctggtggg gaactcttct ttgatcctaa cctgctctct    420
ctggatggaa acgcggccct aactggctca atgatgagtc catgtggcaa atactgggct    480
tacggcgttt ctgaacatgg ttctgattgg atgacaacat atgttcggaa aacatcgtca    540
ccgcatatgc cttctcaaga gaagggcaaa gatcctggaa gaatggacga cgttatccgt    600
tactctcgct tctttattgt atattggtcg agtgacagca aaggtttttt ctattctaga    660
tatccaccag aagatgacga gggcaaaggc aatacacctg cgcagaattg catggtgtat    720
tatcaccgcc tcggggagaa acaggaaaaa gatactcttg tctatgagga tcccgagcat    780
ccattctggc tctgggcact gcagctctcc cctagtggcc gatatgcact cttgactgca    840
agccgggatg ctagtcatac tcaactagcc aaaattgctg atattgggac gagcgacatt    900
caaaacggta ttcaatggtt gactatccat gatcaatggc aggctagatt tgttataatt    960
ggagacgatg attcaacaat ttatttcatg acgaacctag aagctaaaaa ttacctagta   1020
gcaaccttgg acattcggca ttcagaagcg gggtcaaga cactggtggc tgaaaatcct   1080
gacgcccttc tcatatcggc aagcatcctc tcgaccgata aactcgtcct cgtctacctt   1140
cataatgcca ggcatgaaat ccatgtacac gatcttaaca ccggaaaaca gatccgccag   1200
atattcgaca atttgatcgg gcagttttcg ctgtcgggac ggcgtgacga taacgatatg   1260
tttgtctttc acagtggttt cacttctccc ggcaccatat atcggttccg attgaatgaa   1320
gatagtaaca agggcaccct atttcgtgct gtacaggttc ctggcctcaa cctgagtgat   1380
ttcacgacag aatcggtgtt ttatccatca aaggatggga ctcctattca catgttcatt   1440
actcgattga aggatacccc cgtcgacgga actgcccctg tatatattta tggctacggc   1500
ggcttcgccc tggcaatgct cccgaccttc tctgtctcga cgcttctgtt ctgcaagatc   1560
taccgggcaa tgtatgtggt acccaacata cgtggtggtt cagagtttgg agaatcatgg   1620
caccgggagg gaatgttgga caagaaacag aacgtgttcg acgacttcaa tgcagctacg   1680
aaatggctcg ttgcgaacaa atatgccaat aaatataacg ttgccattcg cggaggatcc   1740
aacggaggag ttttgacaac tgcgtgtgcg aatcaagcgc ctgagctcta ccgctgtgtc   1800
atcacaattg gaggtatcat cgacatgctc agatttccca agtttacttt cggcgcttta   1860
tggcgttcgg aatacggtga tcccgaggat ccggaggatt ttgacttcat ttacaagtat   1920
tccccttatc ataacattcc atcaggagat gtagtcttgc cagctatgct tttctttact   1980
gctgcgtatg atgaccgagt ttctcctctg cactcattca aacatgttgc tgccttacag   2040
tataacttcc ccaatggtcc aaacccggtt ttgatgcgta ttgatctaaa cactggacat   2100
ttcgccggca agagtacaca gaaaatgctc gaagaaaccg ccgacgagta cagttttatc   2160
gggaaatcca tgggactagt tatgtgcgct cagaacgaac acgcgtcaaa gcaatggtcc   2220
tgtgtcgtga cctga                                                    2235
```

<210> SEQ ID NO 112
<211> LENGTH: 417
<212> TYPE: PRT
<213> ORGANISM: Lentinula edodes

<400> SEQUENCE: 112

-continued

```
Met Glu Thr Pro Thr Leu Asn Lys Ser Gly Ser Leu Thr Ile Val Gly
1               5                   10                  15

Thr Gly Ile Glu Ser Ile Gly Gln Met Thr Leu Gln Thr Leu Ser Tyr
            20                  25                  30

Ile Glu Ala Ala Asp Lys Val Phe Tyr Cys Val Ile Asp Pro Ala Thr
        35                  40                  45

Glu Ala Phe Ile Leu Thr Lys Asn Lys Asp Cys Val Asp Leu Tyr Gln
    50                  55                  60

Tyr Tyr Asp Asn Gly Lys Ser Arg Met Asp Thr Tyr Thr Gln Met Ser
65                  70                  75                  80

Glu Val Met Leu Arg Glu Val Arg Lys Gly Leu Asp Val Val Gly Val
                85                  90                  95

Phe Tyr Gly His Pro Gly Val Phe Val Asn Pro Ser Leu Arg Ala Leu
            100                 105                 110

Ala Ile Ala Lys Ser Glu Gly Phe Lys Ala Arg Met Leu Pro Gly Val
        115                 120                 125

Ser Ala Glu Asp Cys Leu Tyr Ala Asp Leu Cys Ile Asp Pro Ser Asn
    130                 135                 140

Pro Gly Cys Leu Thr Tyr Glu Ala Ser Asp Phe Leu Ile Arg Glu Arg
145                 150                 155                 160

Pro Thr Asn Ile Tyr Ser His Phe Ile Leu Phe Gln Val Gly Cys Val
                165                 170                 175

Gly Ile Ala Asp Phe Asn Phe Thr Gly Phe Glu Asn Ser Lys Phe Gly
            180                 185                 190

Ile Leu Val Asp Arg Leu Glu Lys Glu Tyr Gly Ala Glu His Pro Val
        195                 200                 205

Val His Tyr Ile Ala Ala Met Leu Pro His Glu Asp Pro Val Thr Asp
    210                 215                 220

Gln Trp Thr Ile Gly Gln Leu Arg Glu Pro Glu Phe Tyr Lys Arg Val
225                 230                 235                 240

Gly Gly Val Ser Thr Phe Tyr Ile Pro Pro Lys Glu Arg Lys Glu Ile
                245                 250                 255

Asn Val Asp Ile Ile Arg Glu Leu Lys Phe Leu Pro Glu Gly Lys Val
            260                 265                 270

Pro Asp Thr Arg Thr Gln Ile Tyr Pro Pro Asn Gln Trp Glu Pro Glu
        275                 280                 285

Val Pro Thr Val Pro Ala Tyr Gly Ser Asn Glu His Ala Ala Ile Ala
    290                 295                 300

Gln Leu Asp Thr His Thr Pro Pro Glu Gln Tyr Gln Pro Leu Ala Thr
305                 310                 315                 320

Ser Lys Ala Met Thr Asp Val Met Thr Lys Leu Ala Leu Asp Pro Lys
                325                 330                 335

Ala Leu Ala Glu Tyr Lys Ala Asp His Arg Ala Phe Ala Gln Ser Val
            340                 345                 350

Pro Asp Leu Thr Ala Asn Glu Arg Thr Ala Leu Glu Ile Gly Asp Ser
        355                 360                 365

Trp Ala Phe Arg Cys Ala Met Lys Glu Met Pro Ile Ser Leu Leu Asp
    370                 375                 380

Asn Ala Lys Gln Ser Met Glu Glu Ala Ser Glu Gln Gly Phe Pro Trp
385                 390                 395                 400

Ile Ile Val Val Gly Val Val Gly Val Val Gly Ser Val Val Ser Ser
                405                 410                 415

Ala
```

<210> SEQ ID NO 113
<211> LENGTH: 127
<212> TYPE: PRT
<213> ORGANISM: Lentinula edodes

<400> SEQUENCE: 113

Met Thr Asp Thr Thr Lys Ile Lys Thr Val Arg Lys Phe His Asp Leu
1               5                   10                  15

Leu Asn Glu Gly Lys Leu Asp Glu Ala His Glu Leu Leu Ala Glu Asp
            20                  25                  30

Leu Ser Ala His Thr Thr Ala His Ile Ala Ala Gly Ala Pro Pro Met
        35                  40                  45

Ser Lys Ala Glu Val Leu Glu Ser His Gln Gly Ile His Gln Glu Leu
    50                  55                  60

Glu Ala Lys Thr Thr Ile Thr Asp Ala Lys Glu Val Asp Gly Asn Val
65                  70                  75                  80

Ile Val Val Gly Lys Ser Thr Phe Asn His Asp Thr Ile Lys Glu Val
                85                  90                  95

Pro Phe Lys Ala Thr Tyr Glu Phe Ile Gly Asn Gln Ile Gly Lys Val
            100                 105                 110

His Phe Glu Thr Asp Pro Asn His Lys Val Lys Ser Phe Ser Leu
        115                 120                 125

<210> SEQ ID NO 114
<211> LENGTH: 411
<212> TYPE: PRT
<213> ORGANISM: Lentinula edodes

<400> SEQUENCE: 114

Met Leu Val Leu Pro Leu Asp Ile Ala Glu Ala Ile Ile Arg Glu Leu
1               5                   10                  15

Leu Ala Arg Lys Asp Lys Ala Thr Val Lys Ser Leu Ser Leu Val Arg
            20                  25                  30

Ser Ser Phe Thr Pro Ile Cys Gln Arg Tyr Leu Leu Ser Asn Ile Ile
        35                  40                  45

Ile Ser Cys Ser Lys Ala Glu Gly Asn Arg Arg Tyr Gln Arg Ser Ser
    50                  55                  60

Asp Ala Thr Leu Lys Leu Leu Arg Ser Ser Pro His Leu Val Ser Ser
65                  70                  75                  80

Ile Arg Ser Leu Ser Ile Leu Asp Ser Gly Phe Ser Trp Thr Gln Leu
                85                  90                  95

Asp Pro Ala Leu Val Asp Ile Leu Asn Ser Leu Thr Asp Leu Thr Cys
            100                 105                 110

Phe Ile Trp Lys Ala Ala Ser Asn Ser Ser Arg Pro Thr Tyr Trp Arg
        115                 120                 125

Glu Leu Pro Gln Pro Leu Gln Asp Ser Ile Arg Ala Thr Ile Arg Arg
    130                 135                 140

Pro Ser Val Thr Ser Leu Phe Leu His Phe Ala Asp Leu Thr Asp Leu
145                 150                 155                 160

Leu Asn Ala Arg Ile Ile Ile Ser Pro Ser Leu Thr Tyr Leu Asn Leu
                165                 170                 175

Arg Gly Thr Gly Phe Ser Lys Ile Ala Leu Glu Leu Thr Arg Pro Ser
            180                 185                 190

Ile Ile Pro Phe Gly Glu Met Pro Ser Arg Leu Phe Val Thr Ala Cys
        195                 200                 205

Lys Leu Glu Trp Ile Glu Asp Glu Lys Met Cys Phe Gly Trp Ile Thr
    210                 215                 220

Ala Ile Leu Pro Asn Leu Ser Leu Glu Arg Leu Gln Lys Leu Ala Val
225                 230                 235                 240

Phe Arg Ser Ser Leu Gln Ser Lys Leu Pro Glu Leu Pro Trp Gly Ala
                245                 250                 255

Leu Leu Tyr His Gln Ser Val Gln Ser Asn Leu Glu Glu Leu Trp Phe
            260                 265                 270

Asp Met Ile Ser Thr Asn Gly Pro Pro Val Asp Thr Met Ser Leu Asp
        275                 280                 285

Arg Leu Pro Ser Leu Lys Arg Leu Gly Leu Ser Met Gly Leu Ser Arg
    290                 295                 300

Val Phe Asp Ala Asn Trp Asp Leu Val Leu Gly Leu Ser Arg Phe Phe
305                 310                 315                 320

Glu Asn Thr Asn Ala Ala Gly Ile Thr His Leu Ile Leu Cys Phe Ser
                325                 330                 335

Phe Ser Ser Thr Ser Leu Val Leu Asp Pro Leu Lys Val Pro Trp Gly
            340                 345                 350

Ser Leu Asp Ala Ala Val Ala Ala Ile Pro Thr Leu Arg Trp Val Gly
        355                 360                 365

Val Gln Phe Val Asp Cys Arg Arg Glu Pro Thr Gly Ile Ile Pro Pro
    370                 375                 380

Lys Thr Lys Ile Met Leu Pro Met Leu Thr Glu Arg Gly Ile Leu His
385                 390                 395                 400

Trp Ser Thr Ser Arg Val Glu Phe Pro Gln Ile
                405                 410

<210> SEQ ID NO 115
<211> LENGTH: 744
<212> TYPE: PRT
<213> ORGANISM: Lentinula edodes

<400> SEQUENCE: 115

Met Ser Val Pro Gln Trp Asp Pro Tyr Pro Pro Val Ser Arg Asp Glu
1               5                   10                  15

Thr Ser Ala Ile Thr Tyr Gln Ser Lys Leu Cys Gly Ser Val Thr Val
            20                  25                  30

Arg Asp Pro Tyr Ser Ala Leu Glu Val Pro Phe Asp Asp Ser Glu Glu
        35                  40                  45

Thr Lys Ala Phe Val His Ala Gln Arg Lys Phe Ala Arg Thr Tyr Leu
    50                  55                  60

Asp Glu Ile Pro Asp Arg Glu Thr Trp Leu Gln Thr Leu Lys Glu Ser
65                  70                  75                  80

Trp Asn Tyr Arg Arg Phe Thr Val Pro Lys Arg Glu Ser Asp Gly Tyr
                85                  90                  95

Thr Tyr Phe Glu Tyr Asn Asp Gly Leu Gln Ser Gln Met Ser Leu Arg
            100                 105                 110

Arg Val Lys Val Ser Glu Glu Asp Thr Ile Leu Thr Glu Ser Gly Pro
        115                 120                 125

Gly Gly Glu Leu Phe Phe Asp Pro Asn Leu Leu Ser Leu Asp Gly Asn
    130                 135                 140

Ala Ala Leu Thr Gly Ser Met Met Ser Pro Cys Gly Lys Tyr Trp Ala
145                 150                 155                 160

Tyr Gly Val Ser Glu His Gly Ser Asp Trp Met Thr Thr Tyr Val Arg

-continued

```
                165                 170                 175

Lys Thr Ser Ser Pro His Met Pro Ser Gln Glu Lys Gly Lys Asp Pro
            180                 185                 190

Gly Arg Met Asp Asp Val Ile Arg Tyr Ser Arg Phe Phe Ile Val Tyr
        195                 200                 205

Trp Ser Ser Asp Ser Lys Gly Phe Phe Tyr Ser Arg Tyr Pro Pro Glu
    210                 215                 220

Asp Asp Glu Gly Lys Gly Asn Thr Pro Ala Gln Asn Cys Met Val Tyr
225                 230                 235                 240

Tyr His Arg Leu Gly Glu Lys Gln Glu Lys Asp Thr Leu Val Tyr Glu
                245                 250                 255

Asp Pro Glu His Pro Phe Trp Leu Trp Ala Leu Gln Leu Ser Pro Ser
            260                 265                 270

Gly Arg Tyr Ala Leu Leu Thr Ala Ser Arg Asp Ala Ser His Thr Gln
        275                 280                 285

Leu Ala Lys Ile Ala Asp Ile Gly Thr Ser Asp Ile Gln Asn Gly Ile
    290                 295                 300

Gln Trp Leu Thr Ile His Asp Gln Trp Gln Ala Arg Phe Val Ile Ile
305                 310                 315                 320

Gly Asp Asp Asp Ser Thr Ile Tyr Phe Met Thr Asn Leu Glu Ala Lys
                325                 330                 335

Asn Tyr Leu Val Ala Thr Leu Asp Ile Arg His Ser Glu Ala Gly Val
            340                 345                 350

Lys Thr Leu Val Ala Glu Asn Pro Asp Ala Leu Leu Ile Ser Ala Ser
        355                 360                 365

Ile Leu Ser Thr Asp Lys Leu Val Leu Val Tyr Leu His Asn Ala Arg
    370                 375                 380

His Glu Ile His Val His Asp Leu Asn Thr Gly Lys Gln Ile Arg Gln
385                 390                 395                 400

Ile Phe Asp Asn Leu Ile Gly Gln Phe Ser Leu Ser Gly Arg Arg Asp
                405                 410                 415

Asp Asn Asp Met Phe Val Phe His Ser Gly Phe Thr Ser Pro Gly Thr
            420                 425                 430

Ile Tyr Arg Phe Arg Leu Asn Glu Asp Ser Asn Lys Gly Thr Leu Phe
        435                 440                 445

Arg Ala Val Gln Val Pro Gly Leu Asn Leu Ser Asp Phe Thr Thr Glu
    450                 455                 460

Ser Val Phe Tyr Pro Ser Lys Asp Gly Thr Pro Ile His Met Phe Ile
465                 470                 475                 480

Thr Arg Leu Lys Asp Thr Pro Val Asp Gly Thr Ala Pro Val Tyr Ile
                485                 490                 495

Tyr Gly Tyr Gly Gly Phe Ala Leu Ala Met Leu Pro Thr Phe Ser Val
            500                 505                 510

Ser Thr Leu Leu Phe Cys Lys Ile Tyr Arg Ala Met Tyr Val Val Pro
        515                 520                 525

Asn Ile Arg Gly Gly Ser Glu Phe Gly Glu Ser Trp His Arg Glu Gly
    530                 535                 540

Met Leu Asp Lys Lys Gln Asn Val Phe Asp Asp Phe Asn Ala Ala Thr
545                 550                 555                 560

Lys Trp Leu Val Ala Asn Lys Tyr Ala Asn Lys Tyr Asn Val Ala Ile
                565                 570                 575

Arg Gly Gly Ser Asn Gly Gly Val Leu Thr Thr Ala Cys Ala Asn Gln
            580                 585                 590
```

-continued

| | | | | | | | | | | | | | | | |
|---|---|---|---|---|---|---|---|---|---|---|---|---|---|---|---|
| Ala | Pro | Glu | Leu | Tyr | Arg | Cys | Val | Ile | Thr | Ile | Gly | Gly | Ile | Ile | Asp |
| | | 595 | | | | | 600 | | | | | 605 | | | |
| Met | Leu | Arg | Phe | Pro | Lys | Phe | Thr | Phe | Gly | Ala | Leu | Trp | Arg | Ser | Glu |
| | 610 | | | | | 615 | | | | | 620 | | | | |
| Tyr | Gly | Asp | Pro | Glu | Asp | Pro | Glu | Asp | Phe | Asp | Phe | Ile | Tyr | Lys | Tyr |
| 625 | | | | | 630 | | | | | 635 | | | | | 640 |
| Ser | Pro | Tyr | His | Asn | Ile | Pro | Ser | Gly | Asp | Val | Val | Leu | Pro | Ala | Met |
| | | | | 645 | | | | | 650 | | | | | 655 | |
| Leu | Phe | Phe | Thr | Ala | Ala | Tyr | Asp | Asp | Arg | Val | Ser | Pro | Leu | His | Ser |
| | | | 660 | | | | | 665 | | | | | 670 | | |
| Phe | Lys | His | Val | Ala | Ala | Leu | Gln | Tyr | Asn | Phe | Pro | Asn | Gly | Pro | Asn |
| | | 675 | | | | | 680 | | | | | 685 | | | |
| Pro | Val | Leu | Met | Arg | Ile | Asp | Leu | Asn | Thr | Gly | His | Phe | Ala | Gly | Lys |
| | 690 | | | | | 695 | | | | | 700 | | | | |
| Ser | Thr | Gln | Lys | Met | Leu | Glu | Glu | Thr | Ala | Asp | Glu | Tyr | Ser | Phe | Ile |
| 705 | | | | | 710 | | | | | 715 | | | | | 720 |
| Gly | Lys | Ser | Met | Gly | Leu | Val | Met | Cys | Ala | Gln | Asn | Glu | His | Ala | Ser |
| | | | | 725 | | | | | 730 | | | | | 735 | |
| Lys | Gln | Trp | Ser | Cys | Val | Val | Thr | | | | | | | | |
| | | | 740 | | | | | | | | | | | | |